(12) United States Patent
N'Zemba et al.

(10) Patent No.: US 6,528,655 B1
(45) Date of Patent: Mar. 4, 2003

(54) AROMATIC DERIVATIVES WITH HIV INTEGRASE INHIBITORY PROPERTIES

(75) Inventors: Blaise Magloire N'Zemba, Toronto (CA); Gilles Sauvé, Laval (CA); Guy Sévigny, Montréal (CA); Jocelyn Yelle, Laval (CA)

(73) Assignee: Pharmacor, Inc., Laval (CA)

( * ) Notice: Subject to any disclaimer, the term of this patent is extended or adjusted under 35 U.S.C. 154(b) by 0 days.

(21) Appl. No.: 09/963,329

(22) Filed: Sep. 26, 2001

(30) Foreign Application Priority Data

Sep. 27, 2000 (CA) ............................................. 2321348

(51) Int. Cl.[7] .................... C07D 233/90; C07D 229/00; C07D 239/00; A61K 31/415
(52) U.S. Cl. .................... 548/338.1; 562/448; 562/451; 562/455; 564/153; 564/157; 564/158; 514/19; 514/20; 514/400; 514/419; 514/423
(58) Field of Search ............................ 562/448, 451, 562/455; 564/153, 157, 158; 514/19, 20, 400, 419, 423; 548/338.1

(56) References Cited

U.S. PATENT DOCUMENTS 6,362,165 B1 * 3/2002 Sauve

FOREIGN PATENT DOCUMENTS

| FR | 2761687 | 10/1998 |
|---|---|---|
| WO | WO 9948371 | 9/1999 |
| WO | WO 0024392 | 5/2000 |
| WO | WO 0059867 | 10/2000 |

OTHER PUBLICATIONS

Lasky, L. A. et al., Cell (1987) vol. 50, pp. 975–985.
Haseltine, W. A., Faseb J. (1991) vol. 5, pp. 2349–2360.
Goff S. P., J. Acq. Imm. Defic. Syndr. (1990) vol. 3, pp. 817–831.
Bukrinsky, M. I., Proc. Natn. Acad. Sci. USA (1992) vol. 89, pp. 6580–6584.
Gallay, P., et al., Cell (1995) vol. 80, pp. 379–388.
Sakai, H., J. Virol. (1993) vol. 67, pp. 1169–1174.
Wang et al. J. Org. Chem. (1977) vol. 49, pp. 1286.
Burke, Jr. T. R. et al., J. Med. Chem. (1995) vol. 38, pp. 4171–4178.

* cited by examiner

*Primary Examiner*—D. Margaret Seaman
(74) *Attorney, Agent, or Firm*—Ronlad S. Kosie; Robert Brouillette; Gaétan Prince

(57) ABSTRACT

A compound of formula I'

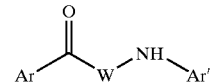

and pharmaceutically acceptable derivatives thereof including, for example, where applicable or appropriate pharmaceutically acceptable salts thereof. Ar and Ar' are aromatic or aryl type groups. The compounds have HIV integrase inhibitory properties. Ar, Ar' and W may be as defined in the specification.

26 Claims, No Drawings

AROMATIC DERIVATIVES WITH HIV INTEGRASE INHIBITORY PROPERTIES

TECHNICAL FIELD OF THE INVENTION

The present invention relates to hydroxylated aromatic and heteroaromatic derivatives which have HIV integrase inhibitory properties that have been characterized by specific structural and physicochemical features. This inhibitory property may be advantageously used, for example, to provide medicinals (e.g. compositions) with antiviral properties against HIV viruses, including the HIV-1 and HIV-2 viruses, i.e. the hydroxyphenyl derivatives including pharmaceutical compositions thereof may be used to inhibit the activity of HIV integrase.

BACKGROUND OF THE INVENTION

The HIV (human immunodeficiency virus) retrovirus is the causative agent for AIDS (acquired immunodeficiency syndrome). Thus the HIV-1 retrovirus primarily uses the CD4 receptor (a 58 kDa transmembrane protein) to gain entry into cells, through high-affinity interactions between the viral envelope glycoprotein (gp 120) and a specific region of the CD4 molecule found in CD4 (+) T-helper lymphocytes and certain other cells (Lasky L. A. et al., Cell vol. 50, p. 975–985 (1987)). HIV infection is characterized by a period immediately following infection called "asymptomatic" which is devoid of clinical manifestations in the patient. Progressive HIV-induced destruction of the immune system then leads to increased susceptibility to opportunistic infections, which eventually produces a syndrome called AIDS-related complex (ARC) characterized by symptoms such as persistent generalized lymphadenopathy, fever, weight loss, followed itself by full blown AIDS. After entry of the retrovirus into a cell, viral RNA is converted into DNA, which is then integrated into the host cell DNA. The reverse transcriptase encoded by the virus genome catalyzes the first of these reactions (Haseltine W. A. FASEB J. vol 5, p. 2349–2360 (1991)). At least three functions have been attributed to the reverse transcriptase: RNA-dependent DNA polymerase activity which catalyzes the synthesis of the minus strand DNA from viral RNA, ribonuclease H (RNase H) activity which cleaves the RNA template from RNA-DNA hybrids and DNA-dependent DNA polymerase activity which catalyzes the synthesis of a second DNA strand from the minus strand DNA template (Goff S. P. J. Acq. Imm. Defic. Syndr. Vol 3, p. 817–831 (1990)). At the end of reverse transcription, the viral genome now in the form of DNA (called provirus) is integrated into host genomic DNA and serves as a template for viral gene expression by the host transcription system, which leads eventually to virus replication (Roth et al., 1989). The preintegration complex consists of integrase, reverse transcriptase, p17 and proviral DNA (Bukrinsky M. I., Proc. Natn. Acad. Sci. USA vol. 89 p. 6580–6584 (1992)). The phosphorylated p17 protein plays a key role in targeting the preintegration complex into the nucleus of the host cell (Gallay et al., 1995).

The primary RNA transcripts made from the provirus are synthesized by the host cell RNA polymerase II which is modulated by two virus-encoded proteins called tat and rev. The viral proteins are formed as polyproteins.

Post-translational modifications of viral polyproteins include processing and glycosylation of Env (envelope) proteins, and myristylation of the N-terminal residue of the p17 protein in the Gag and Gag-Pol polyproteins. The viral protease is involved in processing polyproteins Gag and Gag-Pol into mature proteins, an essential step for virus infectivity. A number of synthetic antiviral agents have been designed to block various stages in the replication cycle of HIV. These agents include compounds which interfere with viral binding to CD4 (+) T-lymphocytes (for example, soluble CD4), compounds which block viral reverse transcriptase (for example, didanosine and zidovudine (AZT)), budding of virion from the cell (interferon), or the viral protease (for example Ritonavir and Indinavir). Some of these agents proved ineffective in clinical tests. Others, targeting primarily early stages of viral replication, have no effect on the production of infectious virions in chronically infected cells. Furthermore, administration of many of these agents in effective therapeutic doses has led to cell-toxicity and unwanted side effects, such as anemia, neurotoxicity and bone marrow suppression. Anti-protease compounds in their present form are typically large and complex molecules of peptidic nature that tend to exhibit poor bioavailability and are not generally consistent with oral administration. These compounds often exhibit side effects such as nausea, diarrhea, liver abnormalities and kidney stones. None of the known antiviral agents target the HIV integrase.

Accordingly, the need exists for compounds that can effectively inhibit the action of this viral enzyme and that can be used for treating HIV infections.

The terms HIV integrase and integrase as used herein are used interchangeably and refer to the integrase enzyme encoded by the human immunodeficiency virus type 1 or 2. In particular this term includes the human immunodeficiency virus type 1 integrase.

SUMMARY OF THE INVENTION

Thus, the present invention relates to a compound of formula I'

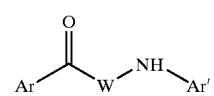

and pharmaceutically acceptable derivatives thereof including, for example, where applicable or appropriate pharmaceutically acceptable salts thereof. Ar may, for example, be $R_1$ which is referred to below; Ar' may, for example, be $R_2$ which is also referred to below.

A compound in accordance with the present invention may, for example, take the form of a compound of formula II', III' or IV' below:

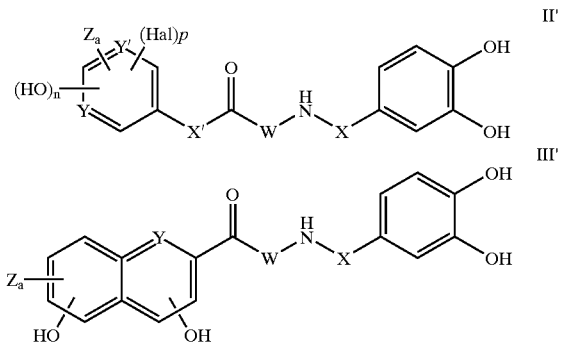

-continued

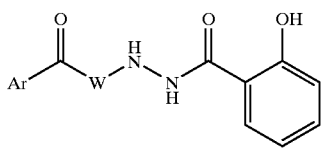

IV'

In accordance with the present invention, n may be 1, 2 or 3; Hal may represent a halogen atom (e.g. Cl, Br, F or I); p may be 0, 1 or 2; X and X' may each independently represent a single bond, a saturated straight or branched hydrocarbon group of 1 to 4 carbon atoms, or a straight or branched hydrocarbon group of 2 to 4 carbon atoms comprising a carbon to carbon double bond; and W may represent an amino acid residue or fragment (in particular alpha-amino acid residues) such as for example a residue based on tyrosine, DOPA, hydroxyproline, serine, threonine, histidine, valine, phenylalanine, lysine, alanine, glycine, glutamic acid, aspartic acid, arginine, asparagine, glutamine, leucine, lysine, isoleucine, proline, tryptophan, methionine, cysteine, cystine, thyroxine, meta-tyrosine, sarcosine, other alpha-methyl amino acids such as alpha-methyl DOPA, as well as other 3-substituted tyrosines, and the like.

$Z_a$ may, for example, be a substituent selected from H, $NO_2$, $NH_2$, alkyloxy, cycloalkyloxy, aryloxy (e.g. benzyloxy), SH, thioalkyl, thioaryl, NHCO-alkyl, NHCO-aryl, etc. $Z_a$ may, for example, be referred to hereinafter interchangeably with respect to particular radicals, groups or moieties, etc. as $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, ect.

In accordance with the present invention an alkyl radical, group or moiety may signifiy an unsubstituted straight-chained (or branched alkyl group) with 1 to 8 carbon atoms; a cycloalkyloxy radical group or moiety may comprise 3 to 8 carbon atoms; an aryl radical, group or moiety may signify a phenyl (or benzyl) group which may be substituted by one or more (e.g. one to three), same or different, substituents such as for example OH, $OCH_3$, SH, $SCH_3$, $NO_2$, $NH_2$, F, Cl, and Br, etc.

Y and Y' may, for example, each independently be C or N.

Ar and Ar' may, for example, each independently represent an aromatic radical, group or moiety which is incorporated into a compound of formula I' by using an appropriate amine, benzoyl hydrazide or carboxylic acid selected, for example, from the following commercially available or synthetic molecules; dopamine, benzylamine, 2,5-dimethoxyaniline, 3-hydroxy-4-methoxyaniline, thiazole-2-amine, 2-(2'-thiophenyl)ethylamine, benzoyl hydrazide, salicylic hydrazide, caffeic acid, dihydrocaffeic acid, 3,4-dihydroxybenzoic acid, 3,5-dihydroxynaphthalene-2-carboxylic acid, 4,8-dihydroxyquinoline-2-carboxylic acid, 2,4-dihydroxypyrimidine-5-carboxylic acid, 2,5-dimethoxycinnamoic acid, 3,4-di-(4-fluorobenzyloxy) benzoic acid, 3,4-di-(4-fluorobenzyloxy)caffeic acid, 5-fluoro-2-hydroxybenzoic acid, 5-fluoroindole-2-carboxylic acid, 2-fluoro-6-hydroxybenzoic acid, 3-hydroxy-4-nitrobenzoic acid, 4-hydroxy-3-nitrobenzoic acid, indole-2-carboxylic acid, N-(4-fluorobenzyl)indole-2-carboxylic acid, N-(4-fluorobenzyl)indole-2-carboxylic acid, 3-nitrocinnamoic acid, 4-nitrocinnamoic acid, pyrrole-2-carboxylic acid, trans-3-indole acrylic acid, 2,4,6-trihydroxybenzoic acid, 3,4,5-trihydroxybenzoic acid, 2-thiophene acetic acid, and the like.

W may, for example, be $W_1$ which is referred to below. W may, for example, be derived from natural or unnatural alpha-amino acids. The term unnatural alpha-amino acid refers to alpha—amino acids which do not occur in nature but which can be derived from naturally occurring alpha—amino acids or other chemical reagents by methods known to those skilled in the art.

W may, for example, represent a group of formula

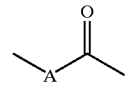

wherein A represents a group of formula

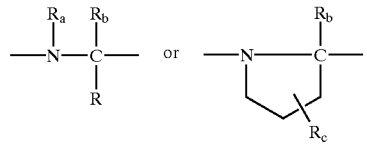

$R_a$ (also referred to herein as $R_3$) may represent H or $-CH_3$; $R_b$ (also referred to herein as $R_4$) may represents H or $-CH_3$; $R_c$ (also referred to herein as $R_6$) may represent H or OH; and R (also referred to herein as $R_5$) may be selected from the group consisting of H, $CH_3-$, $(CH_3)_2CH-$, $(CH_3)_2CHCH_2-$, $CH_3CH_2CH(CH_3)-$, $C_6H_5CH_2-$, $CH_3SCH_2CH_2-$, $HO_2CCH_2-$, $H_2NC(O)CH_2-$, $HO_2CCH_2CH_2-$, $H_2NC(O)CH_2CH_2-$, $H_2NCH_2CH_2CH_2-$, $H_2NCH_2CH_2CH_2CH_2-$, $H_2NCH_2CH_2CH_2CH_2CH_2-$, $HOCH_2-$, $CH_3CH(OH)-$, $HSCH_2-$

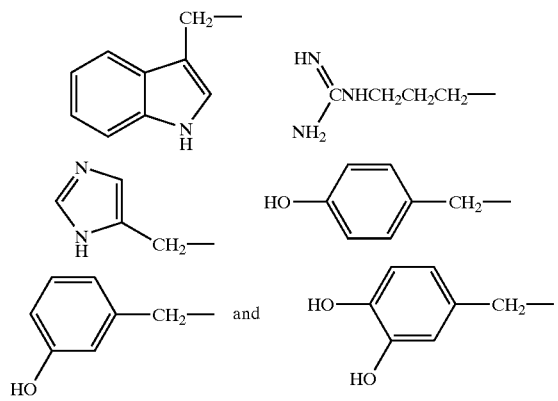

This invention also envisions the presence of a substituent on the side chain of an amino acid residue which bears a functional group such as an alcohol, a phenol, a thiol, a carboxylic acid, an amide, an imidazole, an indole, a pyrrolidine or a guanidine function. For example, the substituents on such functions (e.g. sometimes referred to herein as R' or $R_{20}$) may be selected appropriately from Boc, Fmoc, Bzl, Z, tBu, cHx, Dnp, Trt, Mtt, etc., chosen according to the amino acid used.

Therefore, the present invention in particular provides derivatives wherein R (or $R_5$) may be selected from the group consisting of $R'O_2CCH_2-$, $R'HNC(O)CH_2-$, $R'O_2CCH_2CH_2-$, $R'HNC(O)CH_2CH_2-$, $R'HNCH_2CH_2CH_2-$, $R'HNCH_2CH_2CH_2CH_2-$, $R'HNCH_2CH_2CH_2CH_2CH_2-$, $R'OCH_2-$, $CH_3CH(OR')-$, $R'SCH_2-$

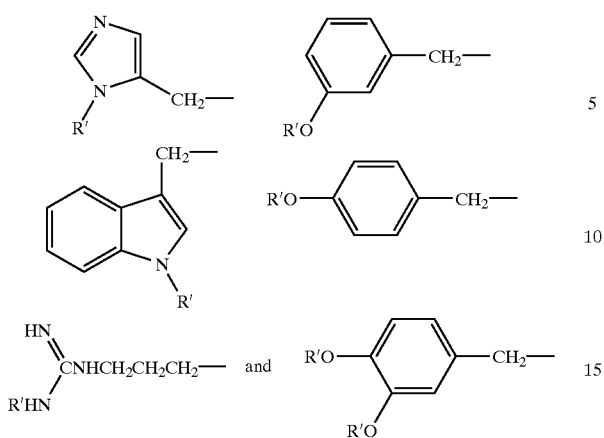

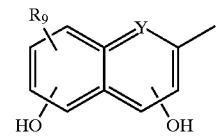   IV

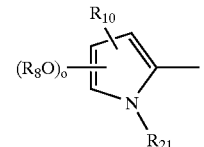   V

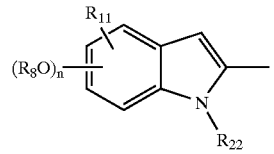   VI

The present invention more particularly provides a compound of formula

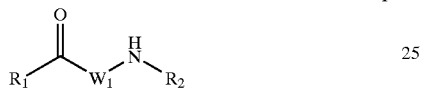   I and pharmaceutically acceptable derivatives thereof including where applicable or appropriate pharmaceutically acceptable salts thereof, e.g. where applicable pharmaceutically acceptable salts, e.g. when a compound of formula I comprises a carboxylic acid group pharmaceutically acceptable salts thereof and when a compound of formula I comprises an amino group pharmaceutically acceptable ammonium salts thereof, Wherein $W_1$ represents a group of formula

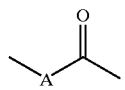

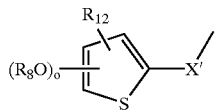   VIa

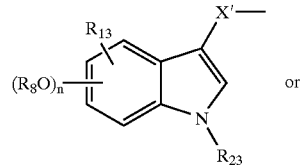   VII

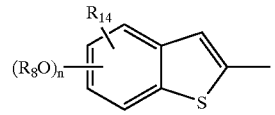   VIIa

A represents a group of formula

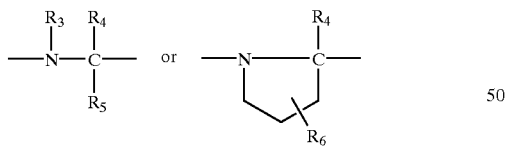

$R_1$ represents a group of formula

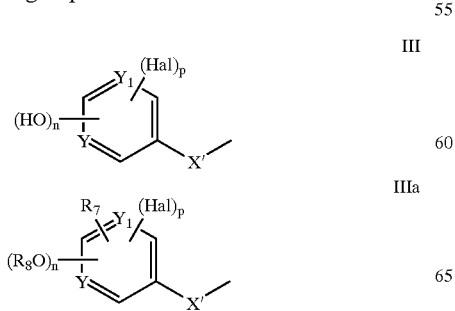

III

IIIa $R_2$ represents a group of formula

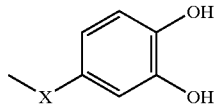   VIII

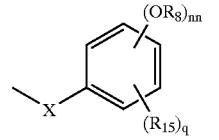   VIIIa

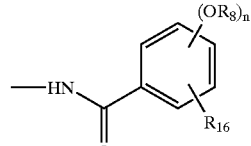   IX

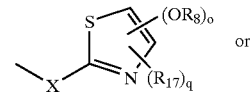   X

-continued

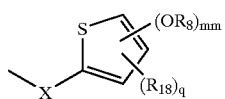

XI $R_3$ represents H or —$CH_3$, $R_4$ represents H or —$CH_3$, $R_6$ represents H or OH, $R_8$ is hydrogen, unsubstituted benzyl, 4-fluorobenzyl or a substituted benzyl of formula $R_{19}C_6H_4CH_2$—

$R_5$ is selected from the group consisting of $R_d$ and $R_e$, provided that when $R_1$ is a group of formula III and $R_2$ is a group of formula VIII, $R_5$ is $R_e$, $R_d$ being selected from the group consisting of H, $C_1$ to $C_8$ alkyl (straight or branched), $HO_2C$—($C_1$ to $C_8$)alkyl (straight or branched)—, $C_6H_5CH_2$—, $CH_3SCH_2CH_2$—, $H_2NC(O)$—($C_1$ to $C_8$)alkyl (straight or branched)—, $HO(C_1$ to $C_8)$alkyl (straight or branched)—, $HSCH_2$—, $H_2N$—($C_1$ to $C_8$)alkyl (straight or branched), (e.g. such as $CH_3$—, $(CH_3)_2CH$—, $(CH_3)_2CHCH_2$—, $C_6H_5CH_2$—, $CH_3CH_2CH(CH_3)$—, $CH_3SCH_2CH_2$—, $HO_2CCH_2$—, $H_2NC(O)CH_2$—, $HO_2CCH_2CH_2$—, $H_2NC(O)CH_2CH_2CH_2$—, $H_2NCH_2CH_2CH_2CH_2$—, $H_2NCH_2CH_2CH_2CH_2CH_2$—, $HOCH_2$—, $CH_3CH(OH)$—, $HSCH_2$—)

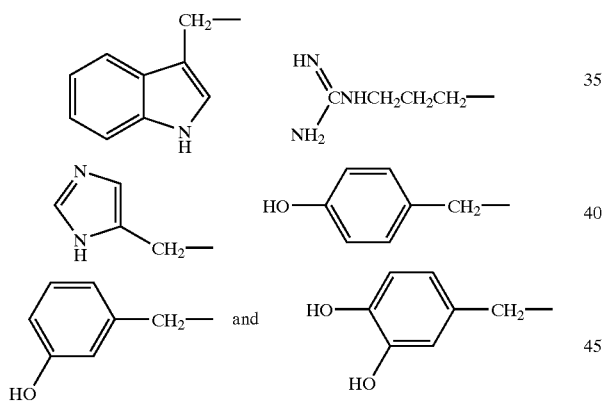

$R_e$ being selected from the group consisting of $R_{20}O_2C$—($C_1$ to $C_8$)alkyl (straight or branched)—, $R_{20}HNC(O)$—($C_1$ to $C_8$)alkyl (straight or branched)—, $R_{20}HN$—($C_1$ to $C_8$)alkyl (straight or branched), $R_{20}O$—($C_1$ to $C_8$)alkyl (straight or branched)—, $R_{20}SCH_2$— (e.g. such as, $R_{20}O_2CCH_2$—, $R_{20}HNC(O)CH_2$—, $R_{20}O_2CCH_2CH_2$—, $R_{20}HNC(O)CH_2CH_2$—, $R_{20}HNCH_2CH_2CH_2$—, $R_{20}HNCH_2CH_2CH_2CH_2$—, $R_{20}HNCH_2CH_2CH_2CH_2CH_2$—, $R_{20}OCH_2$—, $CH_3CH(OR_{20})$—, $R_{20}SCH_2$—),

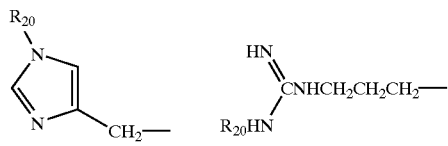

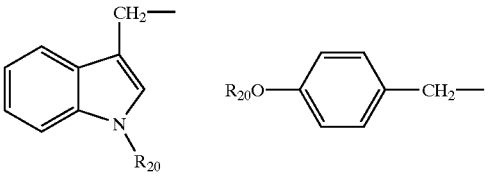

$R_{20}$ is a predetermined protecting group substitutent (i.e. chosen according to the substituent to be protected)

$R_7$ and $R_{15}$, are each independently selected from the group consisting of Hal, —$NO_2$, —$NH_2$, alkyl-O—, cycloalkyl-O—, aryl-O—, benzyloxy, —SH, alkyl-S—, aryl-S—, alkyl-CONH—, aryl-CONH, wherein alkyl signifies an unsubstituted straight or branched alkyl group with 1 to 8 carbon atoms, cycloalkyl signifies an unsubstituted radical with 3 to 8 carbon atoms and aryl signifies an unsubstituted phenyl group, an unsubstituted benzyl group or a phenyl or benzyl group substituted by one or more (i.e. 1 to 3) of the same or different substituents selected from the group consisting of —OH, —$OCH_3$, —SH, —$SCH_3$, —$NO_2$, —$NH_2$, —F, —Cl, and —Br, $R_9$, $R_{10}$, $R_{11}$, $R_{12}$, $R_{13}$, $R_{14}$, $R_{16}$, $R_{17}$, $R_{18}$, and $R_{19}$, are each independently selected from the consisting of H, Hal, —$NO_2$, —$NH_2$, alkyl-O—, cycloalkyl-O—, aryl-O—, benzyloxy, —SH, alkyl-S—, aryl-S—, alkyl-CONH—, aryl-CONH, wherein alkyl signifies an unsubstituted straight or branched alkyl group with 1 to 8 carbon atoms, cycloalkyl signifies an unsubstituted radical with 3 to 8 carbon atoms and aryl signifies an unsubstituted phenyl group, an unsubstituted benzyl group or a phenyl or benzyl group substituted by one or more (i.e. 1 to 3) of the same or different substituents selected from the group consisting of —OH, —$OCH_3$, —SH, —$SCH_3$, —$NO_2$, —$NH_2$, —F, —Cl, and —Br, $R_{21}$, $R_{22}$ and $R_{23}$ are each independently selected from the group consisting of H, alkyl, benzyl, wherein alkyl signifies an unsubstituted straight or branched alkyl group with 1 to 8 carbon atoms, unsubstituted benzyl group or benzyl group substituted by one or more (i.e. 1 to 3) of the same or different substituents selected from the group consisting of —OH, —$OCH_3$, —SH, —$SCH_3$, —$NO_2$, —$NH_2$, —F, —Cl, and —Br, Hal represents a halogen atom (F, Cl, Br, and I), X and X' each independently represents a single bond, a saturated straight or branched hydrocarbon group of 1 to 4 carbon atoms (e.g. alkyl) or a straight or branched hydrocarbon group of 2 to 4 carbon atoms comprising a carbon to carbon double bond;

Y and $Y_1$ each independently represents an atom selected from the group consisting of C, or N, n is 1, 2 or 3, nn is 0, 1, 2 or 3, mm is 0 or 1, p is 0, 1 or 2, o is 0 or 1 q is 0 or 1, provided that for the group of formula III when Y and $Y_1$ are each N, n is 1 or 2 and p is 0 or 1 and provided that when $R_1$ is a group of formula III and $R_2$ is a group of formula VIIIa, q cannot be 0 for the group of formula VIIIa.

It is to be understood herein that n and p are to be selected in relation to each other as well as in relation to the possible presence any other group(s) (e.g. $R_7$) that may be present therewith (e.g. if n is 2 and $R_7$ is H, p is 0, if both Y and $Y_1$ are N; if n is 1 and $R_7$ is H, p may be 1, if both Y and $Y_1$ are C); similarly for o, nn, mm and q. Furthermore, in accordance with the present invention, for the groups of formula III when Y and $Y_1$ are each N, n may be 1 or 2 and p may be 0 or 1.

In accordance with the present invention, $R_{20}$ may be any suitable (known) predertermined protecting group substitutent, e.g. mono- or poly substituted benzyl protective groups, mono- or poly substituted benzyloxycarbonyl protective groups, mono- or poly substituted trityl protective groups, etc. . . . ; see T. W. Greene and P. G. M. Wuts, "Protective Groups in Organic Synthesis" $3^{rd}$ Ed. John Wiley and Sons (1999). $R_{20}$ may, for example, be a predertermined protecting group substitutent selected from the group consisting of Boc (tert-butoxycarbonyl), Fmoc (9-fluorenylmethoxycarbonyl), Bzl (benzyl), Z (benzyloxycarbonyl), tBu (tert-butyl), cHx (cyclohexyl), Dnp (2,4-dinitrophenyl), Trt (trityl), Mtt (methyltrityl), p-Br-benzyl, p-Cl-benzyl, 2,6-dichlorobenzyl, 2,6-fluorobenzyl, p-cyanobenzyl, p-phenylbenzyl, 4-methoxybenzyl, 3,4-dimethoxybenzyl, o-nitrobenzyl, p-nitrobenzyl, 4-methylbenzyl, trifluoromethylbenzyl, p-acylamino-benzyl (e.g. the acyl moiety thereof may contain 1 to 8 carbon atoms in addition to the carbon atom of the carbonyl group—for example alkyl (straight or branched— saturated or unsaturated), cycloalkyl, etc.) p-azidobenzyl, 4-azido-3-chlorobenzyl, p-(methylsulfinyl)benzyl, 4,4'-dimethoxybenzhydryl, 2-bromobenzyloxycarbonyl, 2-chlorobenzyloxycarbonyl, straight or branched $C_1$–$C_8$-alkyl, $C_3$–$C_8$-cycloalkyl, xanthyl, 4-methoxytrityl, di-(4-methoxy)trityl, and tri-(4-methoxy)trityl.

The present invention also contemplates a compound of formula I or I' as defined herein wherein said compound is optically active and where applicable pharmaceutically acceptable salts, amides and esters thereof.

The present invention further provides a pharmaceutical composition (e.g a composition for inhibiting the activity of HIV integrase) comprising a pharmaceutically acceptable carrier and a pharmaceutically effective amount of at least one compound of formula I or I' as defined herein.

The present more particularly provides an hydroxyphenyl compound of formula Ia

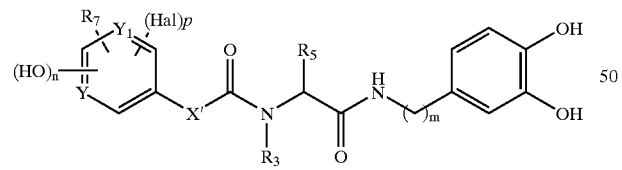

Ia and where applicable pharmaceutically acceptable salts thereof wherein n, p, Hal, X', Y, $Y_1$, $R_3$, $R_5$ and $R_7$ are as defined herein and m is 1 or 2, and provided that, when Y and $Y_1$ are each N, n is 1 or 2 and p is 0 or 1. In accordance with the present invention, for a hydroxyphenyl compound of formula Ia as defined above Y and $Y_1$ may each be C, p may be 0, and $R_7$ may be $NO_2$— or $NH_2$—; X' may be selected from the group consisting of a single bond, —CH=CH—, —$CH_2$— and —$CH_2CH_2$—; $R_3$ may be H; etc.

The present invention further provides an hydroxyphenyl compound of formula Ib

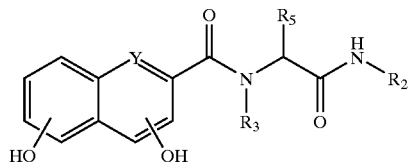

Ib wherein $R_2$ represents a group of formula VIIIa

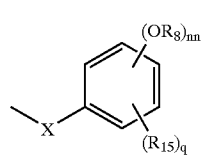

VIIIa and wherein nn is 1, 2 or 3, and Y, X, $R_8$ and $R_{15}$ are as defined herein.

In accordance with the present invention, for an hydroxyphenyl compound of formula Ib as defined above $R_2$ may represent a group of formula

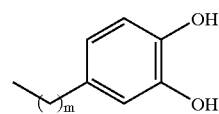

wherein m is 1 or 2; for a compound of formula Ia $R_3$ may be H.

The present invention further provides a hydrazide compound of formula Ic

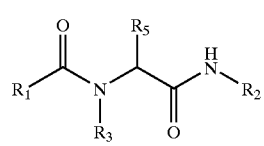

Ic wherein $R_2$ represents a group of formula IX

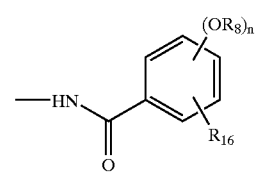

IX and wherein n, $R_1$, $R_3$, $R_5$, $R_8$ and $R_{16}$ are as defined herein. In accordance with the present invention, for a hydrazide compound of formula Ic as defined above, $R_2$ may represent a group of formula

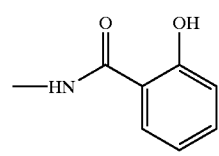

In accordance with the present invention for a hydrazide compound of formula Ic as defined above, $R_1$ may be a group of formula III as defined herein, p may be 0, n may be 1 or 2, Y may be C and $Y_1$ may be C; $R_1$ may be a group of formula IV as defined herein and may be H; $R_1$ may be a group of formula VIa as defined herein, $R_{12}$ may be H, and o may be 0.

The present invention also provides a compound of formula Id

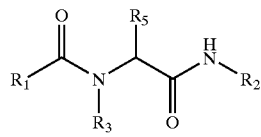

Id wherein $R_2$ represents a group of formula VIIIa

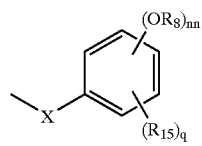

VIIIa wherein nn is 1, 2 or 3, q is 1, and $R_1$, $R_3$, $R_5$, $R_8$ and $R_{15}$ are as defined herein. In accordance with the present invention for a compound of formula Id as defined above $R_2$ may represent a group of formula

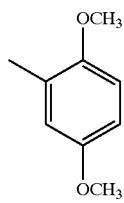

$R_1$ may be a group of formula III, IIIa, V, or VI as defined herein, n may be 1 or 2, p may be 0 or 1, Hal may be F; for a compound of formula Id as defined herein $R_2$ may, for example, alternatively represent a group of formula

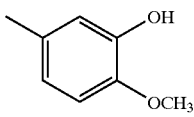

wherein $R_1$ may be a group of formula III, IIIa, V, or VI as defined herein, n may be 1 or 2, p may be 0 or 1, Hal may be F.

The present invention additionally provides a thiazole-2-amine compound of formula Ie

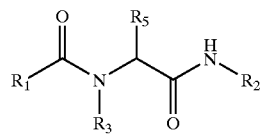

Ie wherein $R_2$ represents a group of formula X

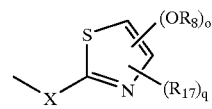

X wherein o, q, $R_1$, $R_3$, $R_5$, $R_8$, and $R_{17}$ are as defined herein. In accordance with the present invention for a thiazole-2-amine compound of formula Ie as defined above $R_2$ may represent a group of formula

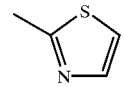

$R_1$ may be a group of formula III, IIIa, V, or VI as defined herein, n may be 1 or 2, p may be 0 or 1, Hal may be F.

The present invention furthermore provides a thiophene compound of formula If

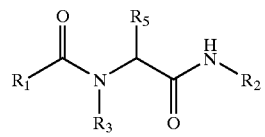

If wherein $R_2$ represents a group of formula XI

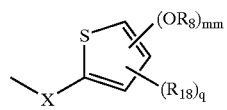

XI and wherein mm, q, $R_1$, $R_3$, $R_5$, $R_8$, and $R_{18}$ are as defined herein. In accordance with the present invention for a thiophene compound of formula If as defined above wherein $R_2$ may represent a group of formula

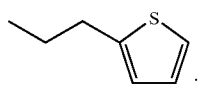

$R_1$ may be a group of formula III, IIIa, V, or VI as defined herein, n may be 1 or 2, p may be 0 or 1, Hal may be F.

In accordance with the present invention there is further provided an hydroxyphenyl compound of formula Ig

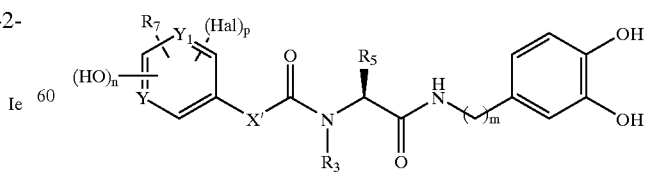

Ig and where applicable pharmaceutically acceptable salts thereof, wherein n is 1, 2 or 3, p, Hal, X', Y, $Y_1$, $R_3$, $R_5$ and $R_7$ are as defined herein, m is 1 or 2 and provided that, when Y and $Y_1$ are each N, n is 1 or 2 and p is 0 or 1. In accordance with the I; present invention for an hydroxyphenyl compound of formula Ig as defined above wherein Y and $Y_1$ may each be C, p may be 0, $R_7$ may be $NO_2$— or $NH_2$—; X' may be selected from the group consisting of a single bond, —CH=CH—, —CH_2— and —CH_2CH_2—; $R_3$ may be H.

The present invention also provides an hydroxyaryl compound of formula II

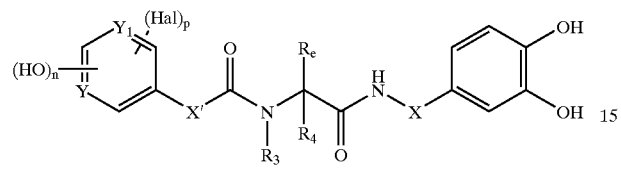

II and pharmaceutically acceptable derivatives thereof including where applicable or appropriate pharmaceutically acceptable salts thereof, wherein n is 1, 2 or 3, p is 0, 1 or 2, Hal, X, X', Y, $Y_1$, $R_3$, $R_e$ and $R_4$ are as defined herein; for the compound of formula II $R_{20}$ may be a predetermined protecting group substitutent selected from the group consisting of Boc (tert-butoxycarbonyl), Fmoc (9-fluorenylmethoxycarbonyl), Bzl (benzyl), Z (benzyloxycarbonyl), tBu (tert-butyl), cHx (cyclohexyl), Dnp (2,4-dinitrophenyl), Trt (trityl), Mtt (methyltrityl). X' may for 5 example be a single bond, —CH=CH—, —CH_2— or —CH_2CH_2—. The compound of formula II may have an optical structure similar to that shown above for the compound of formula Ig.

As mentioned, the present invention include pharmaceutically acceptable derivatives of the compound of formula I or I' (e.g. II', III', etc.). As used herein the expression "pharmaceutically acceptable derivative" is to be understood as referring to any pharmaceutically acceptable salt, amide, ester, or salt of such ester, of a compound of this invention.

The present invention provides, where appropriate, salts (e.g. derived from appropriate bases or acids) which include but are not limited to alkali metal (e.g., sodium, potassium, cesium, etc.) salts, alkaline earth metal (e.g., magnesium) salts, and ammonium salts such as acid addition salts of amines (e.g. ammonium chloride salts) as well as quaternary ammonium salts of for example N—(R")_4^+ type wherein R" is an organic residue.

The pharmaceutically acceptable salts of the compounds of this invention include those derived from pharmaceutically acceptable inorganic and organic acids and bases. Examples of such acid salts include: acetate adipate, alginate aspartate benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

This invention also envisions the quaternization of any basic nitrogen containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodide; and arylalkyl halides including benzyl and phenethyl bromides. Water or oil-soluble or dispersible products may be obtained by such quaternization.

In any event, it is also to be understood that for the present invention the expression "pharmaceutically acceptable derivative" is to be understood as referring to any other compound having a structure such that, upon administration to a recipient, it is capable of providing (directly or indirectly) a compound of this invention or an antivirally active metabolite or residue thereof. Thus the compounds of this invention may be modified by appending appropriate functionalities to enhance selective biological properties. Such modifications are known in the art and include those which increase biological penetration into a given biological system (e.g., blood, lymphatic system, central nervous system), increase oral bioavailability, increase solubility to allow administration by injection, alter metabolism and alter rate of excretion.

The present invention in particular provides a dopamine or benzylamine derivative selected from the group consisting of a compound of formula IA

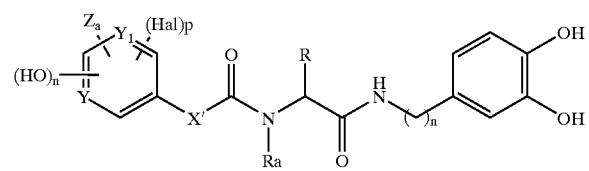

IA n = 1: dihydroxybenzylamine
n = 2: dopamine and where applicable pharmaceutically acceptable salts thereof wherein n, p, Hal, X', Y, $Y_1$, $Z_a$, Ra and R are as defined herein.

The present invention in particular provides a dopamine or benzylamine derivative selected from the group consisting of a compound of formula IIA

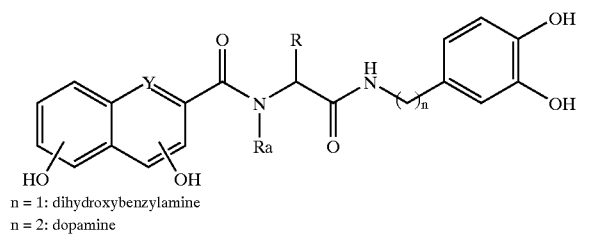

IIA n = 1: dihydroxybenzylamine
n = 2: dopamine wherein n, Y, Ra and R are as defined above.

The present invention in particular provides a salicylic hydrazide derivative selected from the group consisting of a compound of formula IIIA

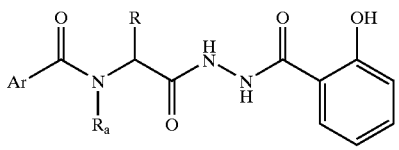

IIIA wherein Ar, $R_a$ and R are as defined above.

The present invention in particular provides a 2,5-dimethoxyaniline derivative selected from the group consisting of a compound of formula IVA

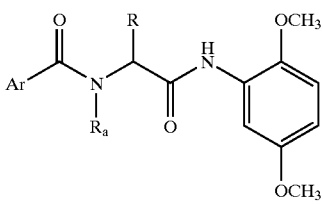

IVA wherein Ar, $R_a$ and R are as defined above.

The present invention in particular provides a thiazole-2-amine derivative selected from the group consisting of a compound of formula IVAA

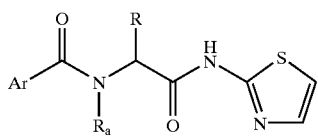

IVAA wherein Ar, $R_a$ and R are as defined above.

The present invention in particular provides a 2-(2'-thiophene)ethylamine derivative selected from the group consisting of a compound of formula IVAAA

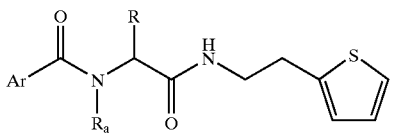

IVAAA wherein Ar, $R_a$ and R are as defined above.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

The amino acid residues may, for example, in any event, be of L, D or DL form, preferably of L form; thus for example the amino acid residue (i.e. W) may be a L-α-amino residue, a D-α-amino residue, or a DL-α-amino residue.

Accordingly, the present invention further provides a dopamine or benzylamine derivative selected from the group consisting of a compound of formula IB

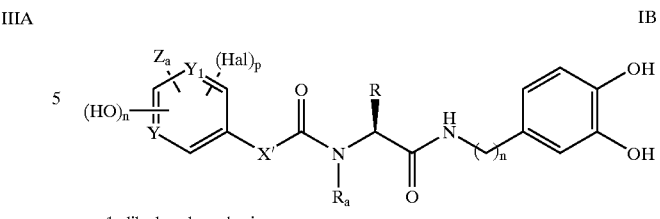

IB n = 1: dihydroxybenzylamine
n = 2: dopamine and where applicable pharmaceutically acceptable salts, thereof, wherein n is 1, 2 or 3, p, Hal, X', Y, $Y_1$, $Z_a$, Ra and R are as defined above.

In the same way or fashion, optically active compounds are envisioned for other compound structures of the present invention, e.g. for derivatives possessing formula IIA, IIIA, IVA, IVAA and IVAAA.

The compounds of the present invention including where applicable their pharmaceutically acceptable derivatives have an affinity for integrase, in particular, HIV integrase. Therefore, these compounds are useful as inhibitors of such integrase, i.e. they are in particular useful as HIV integrase inhibitors. These compounds can be used alone or in combination with other therapeutic or prophylactic agents, such as antivirals, antibiotics, immunomodulators or vaccines, for the treatment or prophylaxis of viral infection.

According to the present invention, the compounds of this invention are capable of inhibiting HIV viral replication in human CD4+ T-cells, by inhibiting the ability of HIV integrase to integrate the double stranded DNA into host genomic DNA for further virus replication by the host cell machinery (Sakai H., J. Virol. Vol. 67 p. 1169–1174 (1993)). These novel compounds can thus serve to reduce the production of infectious virions from acutely infected cells, and can inhibit the initial or further infection of host cells. Accordingly, these compounds are useful as therapeutic and prophylactic agents to treat or prevent infection by HIV-1 and related viruses, which may result in asymptomatic HIV-1 infection, AIDS-related complex (ARC), acquired immunodeficiency syndrome (AIDS), AIDS-related dementia, or similar diseases of the immune system.

Thus the present invention also provides a pharmaceutical composition comprising a pharmaceutically acceptable carrier and a pharmaceutically effective amount of at least one hydroxyphenyl derivative as defined above. The pharmaceutical compositions may be used to inhibit integrase, including HIV integrase, thus providing protection against HIV infection.

The expression "pharmaceutically effective amount" is to be understood herein as referring to an amount effective in treating HIV infection in a patient. The term prophylactically effective amount refers to an amount effective in preventing HIV infection in a patient. As used herein, the term patient refers to a mammal, including a human. The expressions "pharmaceutically acceptable carrier" (or adjuvant) and "physiologically acceptable vehicle" are to be understood as referring to a non-toxic carrier or adjuvant that may be administered to a patient, together with a compound of this invention, and which does not destroy the pharmacological activity thereof. These factors will be discussed in more detail below.

The compounds of this invention may be readily prepared using conventional techniques from commercially available and cheap starting materials. The relative ease of synthesis of the products described in this invention represents a marked advantage for the large scale preparation of these compounds. In general, the derivatives of the present invention may be readily obtained from amino acids through sequences recognized by those knowledgeable in the art as straightforward, requiring readily available reagents and easy techniques. Using standard techniques, amino acids may be transformed to the desired HIV integrase inhibitors according to approaches as shown in Scheme 1, Scheme 2, Scheme 3, Scheme 4, and Scheme 5 which are discussed below. Scheme 6 shows the preparation of two non commercial aromatic acids derived from pyrrole-2-carboxylic acid and indole-2-carboxylic acid which are used in the preparation of HIV integrase inhibitors.

Scheme 1 illustrates a generic example for the preparation of a derivative in accordance with the present invention:

Note:

a) For scheme 1, PG and PG' may be any suitable (known) independently removable protecting group for respectively protecting the amine functional group and the amino acid side chain functional group, when necessary. PG may, for example, be Boc i.e. tert-butoxycarbonyl or Fmoc i.e. 9-fluorenylmethoxycarbonyl and PG' may, for example, be tert-Butyl, Boc, Fmoc, Z i.e. benzyloxycarbonyl, cHx i.e. cyclohexyl, Dnp i.e. dinitrophenyl, Trt i.e. trityl, Mtt i.e. methyltrityl or Bzl, i.e. a functional group of the following formula

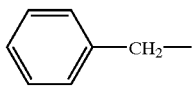

b) For scheme 1, R represents an amino acid side chain as defined above c) Ar and Ar' represent an aromatic pharmacophore linked to the amino acid using the corresponding acid (Ar—$CO_2H$), the corresponding benzoyl hydrazide (Ar'—$CONHNH_2$) or an aromatic amine (Ar'—$NH_2$), and the like.

The definition of PG, PG', R, Ar and Ar' is also presented on scheme 1 (vide infra).

Scheme 1:
General example showing sequencial addition of Ar'—$NH_2$ followed by Ar—$CO_2H$.

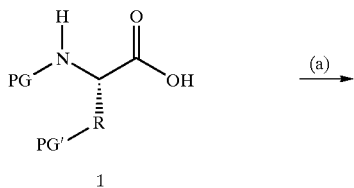

Commercially available or synthesized by standard methodology from an amino acid.
R = amino acid side chain.

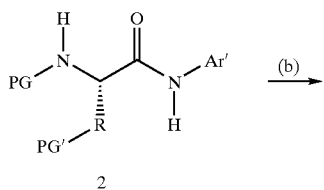

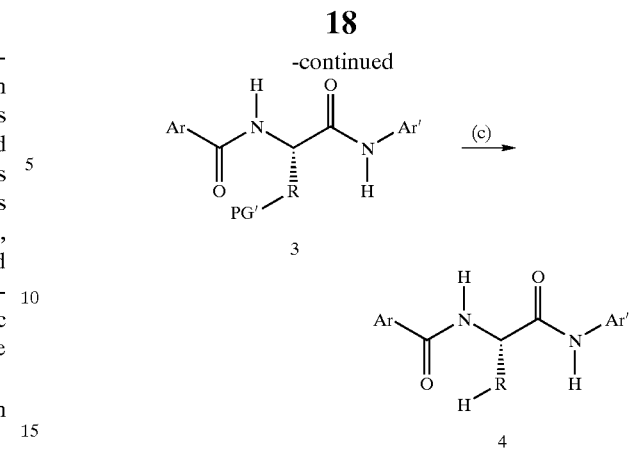

Reagents: a) Coupling reaction with Ar'—$NH_2$; b) 1) Deprotection; 2) Coupling reaction with Ar—$CO_2H$; c) Deprotection.

PG or PG': Protective groups, same or different selected from Boc, Fmoc, Bzl, Z. tBu, cHx, Dnp, Trt, Mtt chosen according to the amino add used. NB: PG' is not necessary for some amino acids.

Ar'—$NH_2$ for derivatives type I, II and IV: Selected from benzylamine, dopamine, 2,5-dimethoxyaniline, 3-hydroxy4-methoxyaniline, thiazole-2-amine, 2-(2'-thiophenyl) ethylamine, and the like Ar'—$CONHNH_2$ for derivatives type III: Selected from benzoyl hydrazide, salicylic hydrazide and the like Ar—$CO_2H$ for derivatives type I, II, III and IV: Selected from caffeic acid, dihydrocaffeic acid, 3,4-dihydroxybenzoic acid, 3,5-dihydroxynaphthalene-2-carboxylic acid, 4,8-dihydroxyquinoline-2-carboxylic acid, 2,4-dihydroxypyrimidine-5-carboxylic add, 2,5-dimethoxycinnamoic acid, 3,4-di-(4-fluorobenzyloxy)benzoic acid, 3,4-di-4-fluorobenzyloxy)caffeic acid, 5-fluoro-2-hydroxybenzoic acid, 5-fluoroindole-2-carboxylic acid, 2-fluoro-6-hydroxybenzoic acid, 3-hydroxy-4-nitrobenzoic acid, 4-hydroxy-3-nitrobenzoic acid, indole-2-acid, N-(4-fluorobenzyl)indole-2-carboxylic acid, N-(4-fluorobenzyl)pyrrole-2-carboxylic acid, 3-nitrocinnamoic acid, 4-nitrocinnamoic acid, pyrrole-2-carboxylic acid, trans-3-indole acrylic acid, 2,4,6-trihydroxybenzoic acid, 3,4,5-trihydroxybenzoic acid, 2-thiophene acetic acid, and the like In accordance with Scheme 1, illustrated above, different pharmacophores may be attached to the amino acid via the C-terminal with the subsequent coupling of Ar—$CO_2H$ taking place at a later stage after the removal of the amino blocking group. Thus, compound 1 (e.g. a Boc amino acid or other N-protected amino acid) is coupled with an aromatic amine (Ar'—$NH_2$) using EDC and HOBt as coupling reagents in DMF to obtain compound 2. Then, compound 2 is treated to remove the protecting or blocking group PG to obtain the free amine; for example, the removal of a Boc group may be performed by stirring compound 2 in a mixture of TFA and methylene chloride at room temperature for a short period of time. The resulting free amine may then be coupled with the appropriate aromatic acid (Ar—$CO_2H$) using the EDC/HOBt coupling conditions in DMF to obtain compound 3. If needed, compound 4 is obtained by deprotection of the protecting group PG' present on the side chain of the amino acid using standard reaction conditions (T. W. Greene and P. G. M. Wuts, Protective groups in organic synthesis, Wiley-Interscience, $3^{rd}$ Ed., 1999).

Scheme 2 illustrates an alternate method for the preparation of a derivative in accordance with the present invention:

Note:

a) For scheme 2, PG and PG', as mentioned above, may be any suitable (known) independently removable protecting group for protecting the amine functional group and the amino acid side chain functional group, when necessary. PG and PG' are defined as above for scheme 1. PG" may be any suitable independently removable protecting group for protecting the carboxylic acid end of an amino acid. PG" may, for example, be Bzl or tert-Butyl b) For scheme 2, R, Ar—CO$_2$H, Ar'—NH$_2$ and Ar'—CONHNH$_2$ are defined as above for scheme 1

The second approach illustrated in scheme 2 below proceeds by linking different pharmacophores to the amino acid via the N-terminal first. Thus, compound 1 is treated so as to protect the carboxylic acid functional group by means of a suitable protecting group PG"; for example compound 1 may be a Boc-amino acid which is benzylated with benzyl bromide to yield compound 5 in the form of a benzyl ester using cesium carbonate in DMF according to the method of S.-S. Wang et al. (J. Org. Chem. vol 49 p. 1286 (1977)). Secondly, the amino protecting group PG is removed to provide a free amino functional group; for example the removal of the Boc group from compound 5 may be carried out by stirring in a mixture of TFA and methylene chloride (1:1 (v/v)). The resulting free amino group is coupled with an Ar—CO$_2$H with EDC and HOBt in DMF providing the desired coupled product compound 6. The latter is treated to remove the protecting group PG" to yield a free carboxylic acid group; for example the benzyl protecting group PG" may be removed by hydrogenolysis using 10% Pd/C as catalyst. Finally the free carboxylic acid intermediate is coupled with an aromatic amine (Ar'—NH$_2$) to provide the desired derivative, namely compound 3. If needed, compound 4 is obtained by deprotection of the protecting group PG' present on the side chain of the amino acid using standard reaction conditions.

Scheme 2:
General example showing sequencial addition of Ar—CO$_2$H followed by Ar'—NH$_2$.

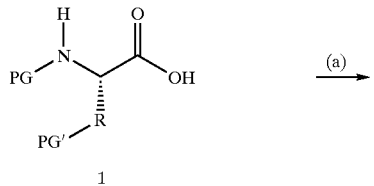

1

Commercially available or synthesized by standard methodology.
R = amino acid side chain.

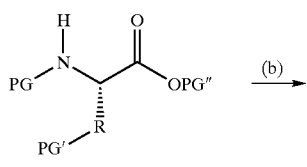

5

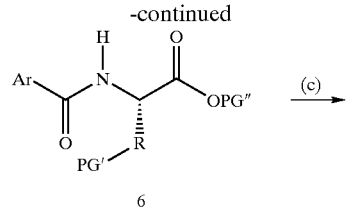

6

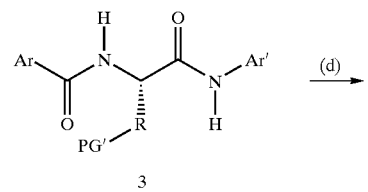

3

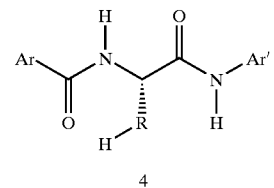

4

Reagents: a) Protection; b) 1) Deprotection; 2) Coupling reaction with Ar—CO$_2$H; c) 1) Deprotection; 2) Coupling reaction with Ar'—NH$_2$; d) Deprotection.

PG, PG' or PG": Protective groups, same or different such as Boc, Fmoc, Bzl, Z, tBu, cHx, Dnp, Trt, Mtt chosen according to the amino acid used. NB: PG' is not necessary for some amino acid.

Ar—CO$_2$H, Ar'—NH$_2$, Ar—CONHNH$_2$: See description in scheme 1.

Scheme 3 illustrates a method for the preparation of a benzylated derivative in accordance with the present invention:

Note:

a) For scheme 3, R is an amino acid side chain without functional group or bearing a functional group which does not need to be protected. R may, for example, be H, CH$_3$—, (CH$_3$)$_2$CH—, (CH$_3$)$_2$CHCH$_2$—, CH$_3$CH$_2$CH(CH$_3$)—, C$_6$H$_5$CH$_2$—, CH$_3$SCH$_2$CH$_2$— b) For scheme 3, Ar—CO$_2$H and Ar'—NH$_2$ are defined as above for scheme 1

Scheme 3:
General example to synthesize benzylated derivatives

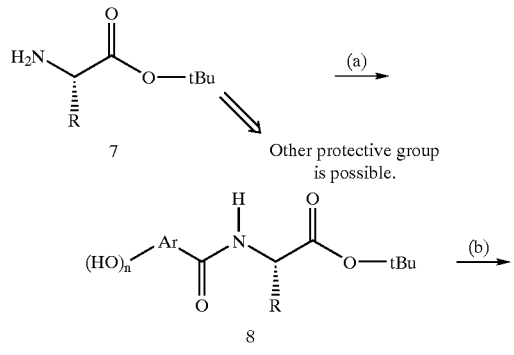

n = 1, 2 or 3

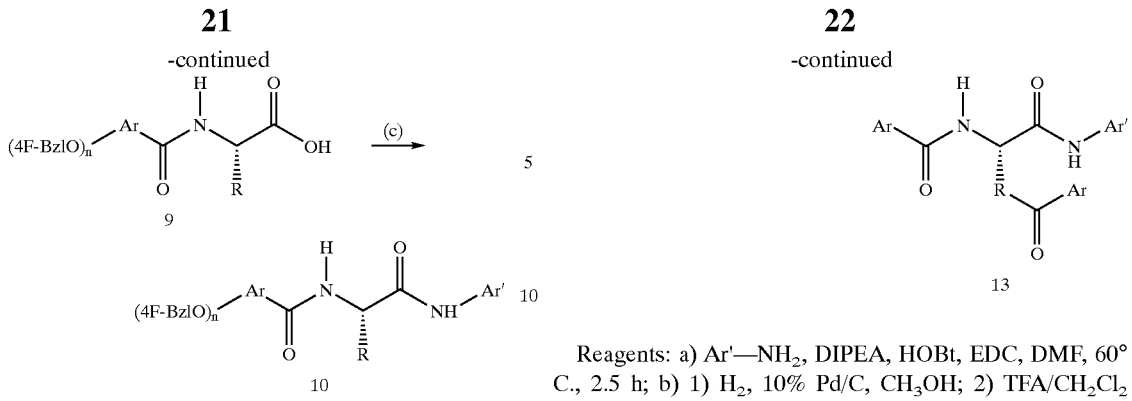

Reagents: a) (HO)ₙAr—CO₂H, HOBt, EDC, DMF, 60° C., 4 h; b) 1) K₂CO₃, 4-F-PhCH₂Br, acetone, 23° C., 16 h; 2) TFA/CH₂Cl₂ (1:1), 23° C., 4 h; c) Ar'—NH₂, DIPEA, HOBt, DMF, 23° C., 2.5 h.

In scheme 3 illustrated above the starting amino acid tert-butyl ester (compound 7) is obtained commercially or synthesized by standard means. Thus, compound 7 is coupled with (HO)ₙAr—CO₂H using EDC and HOBt as coupling reagents in DMF to obtain compound 8. The resulting material is benzylated with 4-fluorobenzylbromide (or other benzyl halide) and potassium carbonate in acetone to yield the acid (compound 9) after deprotection of the tert-butyl protective group. The tert-butyl ester is deprotected in a mixture of TFA/CH₂Cl₂ (1:1) for 4 h. The final material is coupled with an aromatic amine (Ar'—NH₂) (or benzoyl hydrazide) using EDC and HOBt as coupling reagents in DMF to yield compound 10.

Scheme 4 illustrates in a generic fashion a method for the preparation of derivative containing the same moiety at Nα and Nω of an amino acid in accordance with the present invention (see example 11 for a more specific example):

Note:

a) For scheme 4, R represents a nitrogen containing amino acid side chain. R may, for example, be H₂NCH₂CH₂CH₂CH₂—, H₂NCH₂CH₂CH₂—, H₂NCH₂CH₂CH₂CH₂CH₂— b) For scheme 4, two protective groups were used; Boc for the Nα amino group and Z for the Nω amino group.

Scheme 4:
General example with nitrogen containing
amino acid such as Lys, Orn and HomoLys.

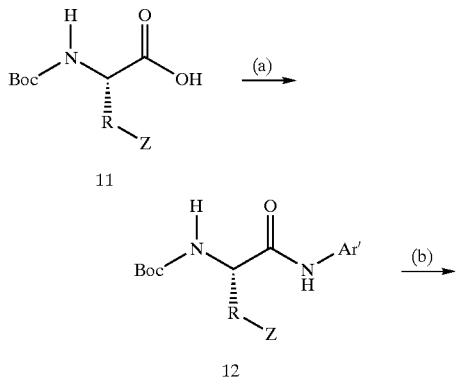

Reagents: a) Ar'—NH₂, DIPEA, HOBt, EDC, DMF, 60° C., 2.5 h; b) 1) H₂, 10% Pd/C, CH₃OH; 2) TFA/CH₂Cl₂ (1:1), 23° C., 2.5 h; 3) ArCO₂H, HOBt, EDC, DIPEA, DMF, 60° C., 4 h.

In scheme 4, commercially available Nα-tert-butoxycarbonyl-Nω-benzyloxycarbonyl amino acid is coupled with an aromatic amine (or benzoyl hydrazide) using HOBt, EDC, DIPEA, as coupling reagents in DMF to yield compound 12. Hydrogenolysis of the Z protective group using 10% Pd/C in methanol followed by deprotection of the Boc group by stirring in a mixture of TFA/CH₂Cl₂ (1:1 (v/v)) gave the free Nα,Nω-diamine. The two amino groups were coupled with ArCO₂H using HOBt, EDC, DIPEA as coupling reagents in DMF to give the desired Nα,Nω-disubstituted product 13.

Scheme 5 illustrates the potential preparation of an anti-integrase derivative using a solid phase methodology in accordance with the present invention (see example 29). Any suitable solid phase substrate could be used in such preparation (K. Burgess, Solid phase organic synthesis, Wiley-Interscience, 2000).

This process allows the introduction of pharmacophores to the amino acid via the N-terminal function. This process is illustrated or examplified with an histidine derivative. Thus, on scheme 5, Nα-(9-fluorenylmethoxycarbonyl)-Nτ-trityl-L-histidine 15 is bound to a polystyrene 2-chlorotrityl resin 14 in a DMF suspension for a period of 16 h. The resulting component 16 contained 0.6 mmol of histidine derivative/500 mg of resin. At this stage, after removal of the Fmoc protective group, the resin can be treated with a variety of aromatic acids (Ar—CO₂H) to give component 17. Cleavage of the resin leads to histidine derivative 18 which can be further transformed into HIV integrase inhibitors upon addition of aromatic amine (Ar'—NH₂) (or benzoyl hydrazide) on the free C-terminal end of the molecule as described earlier.

Scheme 5:
Synthesis using solid phase chemistry.

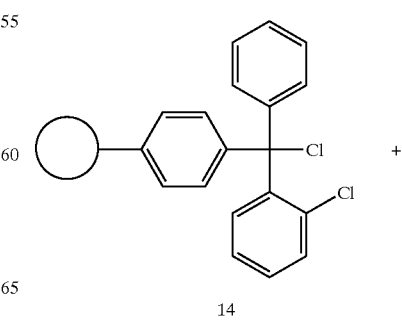

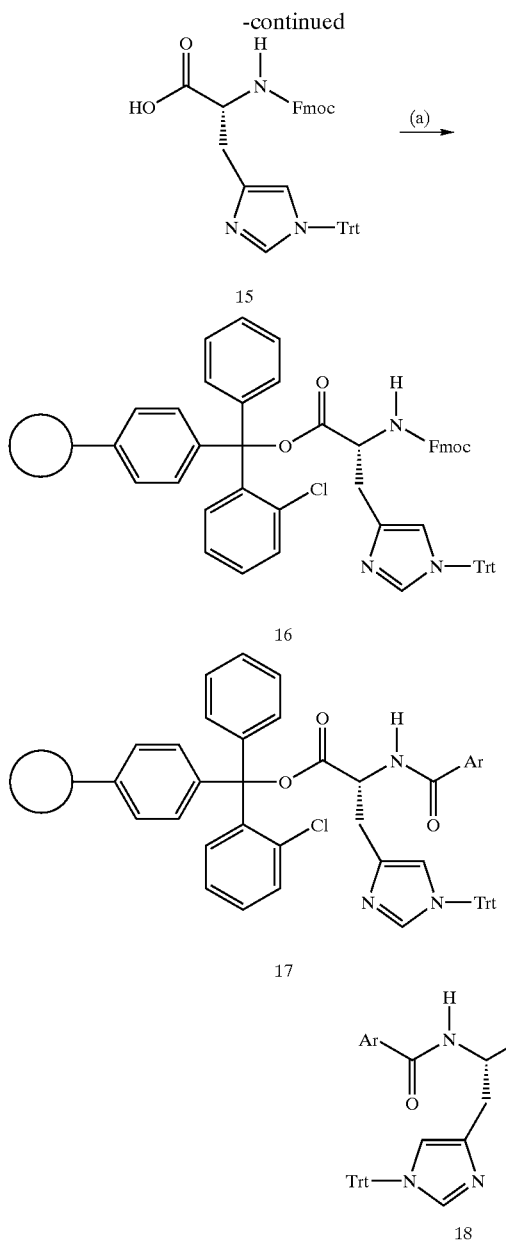

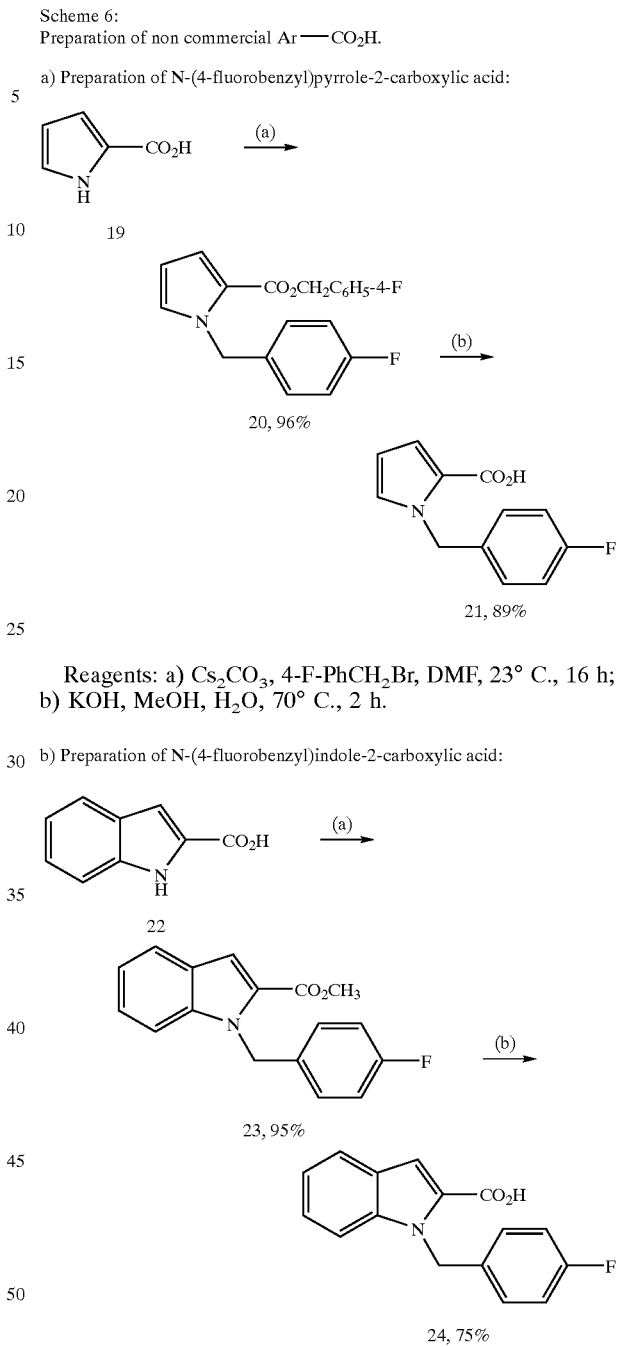

Reagents: a) Cs$_2$CO$_3$, 4-F-PhCH$_2$Br, DMF, 23° C., 16 h; b) KOH, MeOH, H$_2$O, 70° C., 2 h.

b) Preparation of N-(4-fluorobenzyl)indole-2-carboxylic acid:

Reagents: a) Histidine derivative, DIPEA, DMF, 23° C., 16 h; b) 1) 30% piperidine, DMF, 23° C., 1 h; 2) Ar—NH$_2$, HOBt, EDC, DMF, 60° C., 4 h; c) AcOH/Trifluoroethane/CH$_2$Cl$_2$ (1:1:8), 23° C., 2 h.

Scheme 6 illustrates the preparation of non commercially available aromatic acids used for the synthesis of several HIV integrase inhibitors in accordance with the present invention (see example 89 and 93 below for a more specific description of a process for making such derivatives):

For scheme 6 a) pyrrole-2-carboxylic acid 19 is benzylated using cesium carbonate and 4-fluorobenzyl bromide in DMF at room temperature for 3 h to give 96% of compound 20. Saponification of 20 with KOH in methanol at 70° C. for 2 h gave N-(4-fluorobenzyl)pyrrole-2-carboxylic acid 21 (89%).

Reagents: a) 1) MeOH, H$_2$SO$_4$; 2) NaH, 4-F-PhCH$_2$Br, DMF, 23° C., 16 h; b) KOH, MeOH, H$_2$O, 70° C., 2 h.

For scheme 6 b) indole-2-carboxylic acid 22 is treated in methanol in the presence of sulfuric acid to give the methyl ester intermediate which is immediately benzylated by treatment with sodium hydride and 4-fluorobenzyl bromide in DMF to give N-(4-fluorobenzyl)indole-2-methyl carboxylate 23. Saponification of 23 with KOH in methanol at 70° C. for 2 h gave N-(4-fluorobenzyl)indole-2-carboxylic acid 24 (75%). carboxylate 23. Saponification of 23 with KOH in methanol at 70° C. for 2 h gave N-(4-fluorobenzyl)indole-2-carboxylic acid 24 (75%).

The compounds listed in Table 1 to 4 (appearing after the examples) were prepared by following Scheme 1, 2, 3, 4 or 5. Each of the "example numbers" designating each of the compounds listed in these tables, correspond to the respective example number presented in the experimental section (see examples below). The activities of the listed compounds are also listed in the same tables, i.e. demonstrating their potential usefulness. A list of these tables follows:

Table 1: Describes HIV integrase inhibitors formula II'. Compounds no. 1 to 54

Table 2: Describes HIV integrase inhibitors formula III'Compounds no. 55 to 72

Table 3: Describes HIV integrase inhibitors formula IV'. Compounds no. 73 to 81

Table 4: Describes HIV integrase inhibitors formula I'. Compounds no. 82 to 113

As can be appreciated by the skilled artisan, the above synthetic schemes are not intended to comprise a comprehensive list of all means by which the compounds described and claimed in this application may be synthesized. Further methods will be evident to those of ordinary skill in the art.

For the purpose of Table 1 to 4, the HIV-1 integrase inhibition assay was carried out following a known procedure (Burke, Jr. T. R. et al., J. Med. Chem. 38, 4171–4178 (1995)). A suitable radiolabeled duplex substrate corresponding to the U5 end of the HIV LTR was used.

The novel compounds of the present invention are excellent ligands for integrase, particularly HIV-1, and most likely HIV-2 and HTLV-1 integrase. Accordingly, these compounds are capable of targeting and inhibiting an early stage event in the replication, i.e. the integration of viral DNA into the human genome, thus preventing the replication of the virus.

In addition to their use in the prophylaxis or treatment of HIV infection, the compounds according to this invention may also be used as inhibitory or interruptive agents for other viruses which depend on integrases, similar to HIV integrases, for obligatory events in their life cycle. Such compounds inhibit the viral replication cycle by inhibiting integrase. Because integrase is essential for the production of mature virions, inhibition of that process effectively blocks the spread of virus by inhibiting the production and reproduction of infectious virions, particularly from acutely infected cells. The compounds of this invention advantageously inhibit enzymatic activity of integrase and inhibit the ability of integrase to catalyze the integration of the virus into the genome of human cells.

The compounds of this invention may be employed in a conventional manner for the treatment or prevention of infection by HIV and other viruses which depend on integrases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection. Also, a compound of this invention may be combined with pharmaceutically acceptable adjuvants conventionally employed in vaccines and administered in prophylactically effective amounts to protect individuals over an extended period of time against viral infections, such as HIV infection. As such, the novel integrase inhibitors of this invention can be administered as agents for treating or preventing viral infections, including HIV infection, in a mammal. The compounds of this invention may be administered to a healthy or HIV-infected patient either as a single agent or in combination with other antiviral agents which interfere with the replication cycle of HIV. By administering the compounds of this invention with other antiviral agents which target different events in the viral replication cycle, the therapeutic effect of these compounds is potentiated. For instance, the co-administered antiviral agent can be one which targets early events in the life cycle of the virus, such as cell entry, reverse transcription and viral DNA integration into cellular DNA. Antiviral agents targeting such early life cycle events include, didanosine (ddI), zalcitabine (ddC), stavudine (d4T), zidovudine (AZT), polysulfated polysaccharides, sT4 (soluble CD4)—which blocks attachment or adsorption of the virus to host cells—and other compounds which block binding of virus to CD4 receptors on CD4-bearing T-lymphocytes. Other retroviral reverse transcriptase inhibitors, such as derivatives of AZT, may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformiate, eflornithine, ribavirin, acyclovir, alpha interferon and trimenotrexate. Additionally, non-ribonucleoside inhibitors of reverse transcriptase, such as TIBO, nevirapine or delavirdine, may be used to potentiate the effect of the compounds of this invention, as may viral uncoating inhibitors, inhibitors of trans-activating proteins such as tat or rev, or inhibitors of the viral protease. These compounds may also be co-administered with other inhibitors of HIV integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. Preferred combination therapies include the administration of a compound of this invention with AZT, 3TC, ddI, ddC, d4T, combivir, ziagen, sustiva, nevirapine and delavirdine.

Alternatively, the compounds of this invention may also be co-administered with other HIV protease inhibitors such as saquinavir (from Roche), indinavir (from Merck), nelfinavir (from Agouron), ritonavir (from Abbott) and amprenavir (from Glaxo) to increase the effect of therapy or prophylaxis against various viral mutants or members of other HIV quasi species.

We prefer administering the compounds of this invention as single agents or in combination with retroviral reverse transcriptase inhibitors, such as derivatives of AZT or HIV aspartyl protease inhibitors. We believe that the co-administration of the compounds of this invention with retro viral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbante, tumor necrosis factor, naltrexone and rEPO); antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an integrase inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar integrases for obligatory events in their life cycle. These viruses include, but are not limited to, other diseases caused by retroviruses, such as simian immunodeficiency viruses, HTLV-I and HTLV-II.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solutions. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral administration carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical compositions can be formulated with a suitable lotion or cream containing the active compound suspended or dissolved in a carrier. Suitable carriers include, but are not limited to mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 75% active compound (w/w). Preferably, such preparations contain from about 20% to about 50% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease, at least in principle. Patients may, however, require intermittent treatment on a long-term basis, upon any recurrence of disease symptoms, especially for AIDS.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to integrases, particularly HIV integrase. As commercial reagent, the compounds of this invention, and their derivatives, may be used to block integration of a target DNA molecule by integrase, or may be derivatized to bind to a stable resin as a tethered substrate for affinity chromatography applications. These and other uses which characterize commercial integrase inhibitors will be evident to those of ordinary skill in the art.

DETAILED DESCRIPTION OF THE INVENTION

In the description herein, the following abbreviations are used:

| Abbreviation | Meaning |
|---|---|
| AcOH | Acetic acid |
| ARC | AIDS-related complex |
| AIDS | Acquired Immunodeficiency Syndrome |
| AZT | 3-Azido-3-deoxythymine (Zidovudine) |
| Boc | tert-Butoxycarbonyl |
| BOP | 1-Benzotriazolyloxy-tris-dimethylamino-phosphonium hexafluorophosphate |
| BSA | Bovine serum albumin |
| t-Bu | tert-Butyl |
| Bz | Benzoyl |
| Bzl | Benzyl |
| Caffeoyl | 3,4-dihydroxycinnamoyl |
| Cinnamoyl | 3-phenylacryloyl |
| DABCYL | 4-[[4'-(dimethylamino)phenyl]azo]benzoic acid |
| DEAD | Diethyl azodicarboxylate |
| DIEA | N,N-Diisopropylethylamine |
| DMF | Dimethylformamide |
| DNA | Deoxyribonucleic acid |
| DTT | Dithiothreitol |
| EDANS | 5-[(2'-aminoethyl)amino]naphthalene sulfonic acid |
| EDC | 1-Ethyl-3-(3-dimethlaminopropyl)carbodiimide hydrochloride |
| EDTA | Ethylenediaminetetraacetic acid |
| EtOAc | Ethyl acetate |
| EtOH | Ethyl alcohol |
| Fmoc | 9-Fluorenylmethoxycarbonyl |
| g | gram |
| HPLC | High pressure liquid chromatography |
| HOBt | 1-hydroxybenzotriazole hydrate |
| HIV-1, -2 | Human immunodeficiency virus type 1, type 2 |

-continued

| Abbreviation | Meaning |
|---|---|
| HTLV-I, -II | Human T-cell lymphotropic virus type I, type II |
| IL-2 | Interleukin-2 |
| M | Molar |
| MeOH | Methyl alcohol |
| mg | Milligram |
| MP | Melting Point |
| min | Minute |
| mL | Milliliter |
| mmol | Millimol |
| nM | Nanomolar |
| rEPO | Recombinant erythropoietin |
| RNA | Ribonucleic acid |
| 3TC | 2',3'-Dideoxy-3-thiacytidine |
| TFA | Trifluoroacetic acid |
| THF | Tetrahydrofuran |
| Trityl | Triphenylmethyl |
| Z | Benzyloxycarbonyl |

Also, in alphabetical order, the following standard abbreviations were used for the description of the amino acids found in tables 1 to 4.

| Abbreviation | Meaning |
|---|---|
| Asn | DL, D- or L-asparagine |
| Asp | DL, D- or L-aspartic acid |
| Cys | DL, D- or L-cysteine |
| Glu | DL, D- or L-glutamic acid |
| Gln | DL, D- or L-glutamine |
| Gly | glycine |
| His | DL, D- or L-histidine |
| Lys | DL, D- or L-lysine |
| Orn | DL, D- or L-ornithine |
| Phe | DL, D- or L-phenylalanine |
| Ser | DL, D- or L-serine |
| Thr | DL, D- or L-threonine |
| Trp | DL, D- or L-tryptophan |
| Tyr | DL, D- or L-tyrosine |

Combinations of substituents and variables envisioned by this invention are only those that result in the formation of stable compounds.

The term stable, as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

EXAMPLES

In order that this invention be more fully understood, the following examples are set forth. These examples are for the purpose of illustration only and are not to be construed as limiting the scope of the invention in any way.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and a positive nitrogen pressure to allow proper rate of elution. Detection of the compounds was carried out by exposing eluted plates (analytical or preparative) to UV light and/or treating analytical plates with a 2% solution of p-anisaldehyde in ethanol containing 3% sulfuric acid and 1% acetic acid followed by heating.

Unless otherwise indicated, all starting materials were purchased from a commercial source such as Aldrich Co. or Sigma Co.

Nuclear magnetic resonance (NMR) spectra were recorded on a Bruker AMX 500 equipped with a reversed or QNP probe. Samples were dissolved in deuterochloroform ($CDCl_3$), deuteroacetone (acetone-$d_6$) or deuterodimethylsulfoxide (DMSO-$d_6$) for data acquisition using tetramethylsilane as internal standard. Chemical shifts are expressed in parts per million (ppm), the coupling constants (J) are expressed in hertz (Hz) whereas multiplicities are denoted as s for singlet, d for doublet, dd for doublet of doublets, t for triplet, q for quartet, m for multiplet, and br s for broad singlet.

GENERAL PROCEDURES

A. Preparation of N-(tert-Butoxycarbonyl)amino Acids

To a solution of amino acid (1 eq.) in water and dioxane were added at room temperature triethylamine (1.3–1.5 eq.) and Boc-ON (1.1 eq.) or di-tert-butyl-dicarbonate (2 eq.). The mixture was stirred at room temperature under argon for 3 to 5 h. The solution was diluted with water and extracted by ether at least six times. The aqueous layer was acidified to pH ~2.5 with cold 1N HCl to yield an oily layer. The mixture was extracted three times with methylene chloride. The combined organic extracts were washed with brine and dried over magnesium sulfate. After filtration, the filtrate was evaporated using a bath set at 30° C. The residue was found to be of sufficient purity for the next reaction step.

B. Benzylation of N-Boc Amino Acid

Two different solvent systems were used to achieve benzylation of acids or hydroxyl groups.

a) Dimethylformamide Method

To a N-Boc amino acid (1 eq.) in dimethylformamide (DMF) were added cesium carbonate (1.4–2.0 eq.) and benzyl bromide (1.1–1.5 eq.). The reaction mixture was stirred at room temperature overnight under argon. The mixture was diluted with water and the organic layer was extracted with ethyl acetate. The combined organic phases were washed with brine and dried over magnesium sulfate. The solids were filtered off and solvent was evaporated under vacuum yielding a residue that was purified by silica gel chromatography using 20% ethyl acetate in hexane.

b) Acetone Method

To a N-Boc amino acid (1 eq.) in acetone were added potassium carbonate (1.4–2.0 eq.) and benzylbromide (1.1–1.5 eq.). The reaction mixture was stirred at room temperature for a period of 3–5 h under argon. Work-up and purification as carried out in the previous procedure B (a) afforded the desired product.

C. Removal of the N-tert-Butoxycarbonyl (Boc) or the N-Trityl Groups

A solution of N-tert-butoxycarbonyl amino acid (or N-trityl) (1 eq.) in a 1:1 mixture of trifluoroacetic acid (TFA) (10 eq.) and methylene chloride ($CH_2Cl_2$) was stirred at room temperature for 15–30 min. The solvent and excess acid were removed under vacuum to yield the desired product that was used without further purification.

D. Coupling Reaction of Hydroxylated Benzoic Acid (or Other Aromatic Acid) with the NH Part of an Amino Acid To a mixture of hydroxylated benzoic acid (1.5 eq.), hydroxybenzotriazole hydrate (HOBt) (1.6 eq.), and 1-(3-dimethylaminopropyl)-3-ethylcarbodiimide (EDC) (1.6 eq.) in DMF was added a solution of product from procedure C (1 eq.) and triethylamine or diisopropylethylamine (1 eq.) in DMF. The mixture was stirred at room temperature under argon for either 6 h or overnight, monitoring the reaction by TLC. The reaction mixture was quenched by water and extracted three times with ethyl acetate. The organic phases were combined and washed with brine. After drying over magnesium sulfate, the solution was filtered and the solvent was evaporated under vacuum. The residue was purified by silica gel chromatography, eluting as indicated in each procedure.

E. Cleavage of Benzyl Esters or Benzyl Ethers

The benzyl ester or benzyl ether of an amino acid derivative dissolved in methanol was hydrogenated over 10% Pd/C (less than 10% by weight of the weight of the amino acid benzyl ester or ether) under 1 atmosphere of $H_2$ for 1–2 h. The catalyst was filtered off and the filtrate was evaporated under vacuum to yield the desired product.

F. Coupling Reaction of Dopamine (or Other Amine) with the COOH of a Substituted Amino Acid To a solution of substituted carboxylic acid (1 eq.) prepared as in procedure E, HOBt (1.5 eq.) and EDC (1.5 eq.) in DMF at 0° C. was added a solution of dopamine hydrochloride (2 eq.) and triethylamine or diisopropylethylamine (2 eq.) in DMF. The mixture was stirred under argon for 0.5 h and the mixture was allowed to reach room temperature and stirred overnight. The resulting mixture was diluted with water and extracted three times with ethyl acetate. The organic phases were combined and washed with brine. After drying over magnesium sulfate, the solution was filtered and the solvent was evaporated under vacuum. The residue was purified by silica gel chromatography, using eluting agent as indicated in each procedure.

G. Removal of the N-9-Fluorenylmethoxycarbonyl (Fmoc) Group

A solution of N-(9-fluorenylmethoxycarbonyl) amino acid (1 eq.) in 30% diethylamine in acetonitrile was stirred 15 min at room temperature. The solvent was removed under vacuum to yield the desired product that was used without further purification.

Specific Examples for the Preparation of Derivatives of General Formula II'

Example 1

Preparation of N-[Nα-(3,4-Dihydroxybenzoyl)-Oγ-cyclohexyl-L-aspartyl]dopamine (Compound No. 1)

Step A. Preparation of Nα-(tert-Butoxycarbonyl)-Oγ-cyclohexyl-L-aspartic Acid Benzyl Ester The title compound was prepared from Nα-(tert-butoxycarbonyl)-Oγ-cyclohexyl-L-aspartic acid (1.0 g, 3.2 mmol) by following the general procedure B (b). The crude material was purified by flash chromatography using pure hexane and then 15% EtOAc/hexane. The product was isolated as a white solid (1.2 g, 98% yield).

$^1$H NMR (DMSO-$d_6$): 1.2–1.4 (m, 15H), 1.6–1.7 (m, 4H), 2.6–2.8 (ABX, J=9.8, 14.0, 2H), 4.5 (d, J=6.8, 1H), 4.6 (s, 1H), 5.0 (s, 2H), 7.3 (s, 6H).

Step B. Preparation of Nα-(3,4-Dihydroxybenzoyl)-Oγ-cyclohexyl-L-aspartic Acid Benzyl Ester Nα-(tert-butoxycarbonyl)-Oγ-cyclohexyl-L-aspartic acid benzyl ester (456 mg, 1.0 mmol) was deprotected according to the indications of general procedure C. The free α-amino group was coupled with 3,4-dihydroxybenzoic acid (347 mg, 2.3 mmol) according to general procedure D. The crude product was purified by flash chromatography using 20% EtOAc/$CH_2Cl_2$ to yield the desired product (260 mg, 52%).

$^1$H NMR (DMSO-$d_6$): 1.2–1.4 (m, 6H), 1.6–1.7 (m, 4H), 2.5–2.7 (ABX, J=8.6, 13.0, 2H), 4.4 (s, 1H), 4.6 (s, 1H), 5.0 (s, 2H), 6.9 (d, J=7.9, 1H), 7.2–7.3 (m, 8H), 7.5 and 8.0 (2×s, 2×OH).

Step C. Preparation of N-[Nα-(3,4-Dihydroxybenzoyl)-Oγ-cyclohexyl-L-aspartyl]dopamine The title compound was prepared from the product obtained in step B of this example (259 mg, 0.59 mmol) according to the indications of general procedures E and F. The crude material was purified by flash chromatography using EtOAc to yield 140 mg (49%) of the final product as white crystals.

$^1$H NMR (DMSO-d$_6$): 1.2–1.5 (m, 6H), 1.6–1.7 (m, 4H), 2.6 (t, J=7.2, 2H), 2.6–2.8 (ABX, J=7.8, 15.0, 2H), 3.4 (q, J=6.5, 2H), 4.7 (m, 1H), 4.9 (q, J=7.0, 1H), 6.5–7.8 (m, 8H), 7.9 and 8.0 (2×s, 2×OH), 8.5 (br s, 2×OH).

Example 2

Preparation of N-[Nα-(3-Amino-4-hydroxybenzoyl)-Nτ-trityl-D-histidinyl]dopamine (Compound No. 2)

Step A. Preparation of N-[Nα-(9-Fluorenylmethoxycarbonyl)-Nτ-trityl-D-histidinyl]dopamine The title compound was prepared from Nα-(9-fluorenylmethoxycarbonyl)-Nτ-trityl-D-histidine (3.0 g, 4.8 mmol) by following the general procedure F using dopamine hydrochloride (1.4 g, 7.3 mmol). The mixture was stirred at room temperature for 2 h. The crude material was purified by flash chromatography using a solvent gradient from 30% to 80% EtOAc/CH$_2$Cl$_2$ containing 1% AcOH. The product was isolated as a white solid (1.98 g, 54% yield).

$^1$H NMR (DMSO-d$_6$): 2.5 (s, 2H), 2.7–2.9 (m, 2H), 3.2 (s, 2H), 4.2 (m, 4H), 6.4 (s, 1H), 6.6–7.7 (m, 28H), 8.0 (s, 1H), 8.6–8.8 (br s, 2×OH).

Step B. Preparation of N-[Nα-(4-Hydroxy-3-nitrobenzoyl)-Nτ-trityl-D-histidinyl]dopamine N-[Nα-(9-fluorenylmethoxycarbonyl)-Nτ-trityl-D-histidinyl]dopamine (734 mg, 0.97 mmol) was deprotected according to the indications of general procedure G. The product thus obtained was then coupled with 4-hydroxy-3-nitrobenzoic acid (267 mg, 1.46 mmol) according to the indications of general procedure D. The reaction mixture was heated at 60° C. for 4 h. The crude product was purified by flash chromatography using initially 30% then 50% EtOAc/CH$_2$Cl$_2$/1% AcOH and 99% EtOAc/1% AcOH to yield the desired product (230 mg, 34%) as a yellow solid.

$^1$H NMR (DMSO-d$_6$): 2.5 (d, J=3.4, 2H), 2.8–3.0 (m, 2H), 3.2 (m, 2H), 4.6 (m, 1H), 6.3–7.3 (m, 23H), 7.9 (d, J=4.3, 1H), 8.0 (s, 1H), 8.4–9.0 (br s, 3×OH).

Step C. Preparation of N-[Nα-(3-Amino-4-hydroxybenzoyl)-Nτ-trityl-D-histidinyl]dopamine The title compound was prepared from the product obtained in step B of this example (148 mg, 0.2 mmol) according to the indications of general procedure E. The crude material was filtered to yield 80 mg (56%) of the final product as white crystals.

$^1$H NMR (DMSO-d$_6$): 2.5 (q, J=3.6, 2H), 2.9 (d, J=3.0, 2H), 3.2 (s, 2H), 4.6 (m, 1H), 5.6 (s, 2H), 6.3–7.3 (m, 25H), 7,8 (s, 1H), 8.2 (s, 1H), 9.0 (br s, 3×OH).

Example 3

Preparation of Nα,Nε-di-(3,4-Dihydroxybenzoyl)-L-lysine (Compound No. 3)

Step A. Preparation of Nα,Nε-di-(tert-Butoxycarbonyl)-L-lysine Benzyl Ester

Lysine (4.0 g, 27 mmol) was transformed into Nα,Nε-di-(tert-butoxycarbonyl)-L-lysine benzyl ester using the general procedures A and B (b). The crude material was purified by flash chromatography eluting with 10% EtOAc/hexane. The title compound was obtained as a white solid (7.6 g, 64%).

$^1$H NMR (acetone-d$_6$): 1.4–1.6 (m, 22H), 1.8–1.9 (m, 2H), 3.2 (d, J=2.8, 2H), 4.2 (d, J=1.4, 1H), 5.2 (m, 2H), 5.9 (s, 1H), 6.2 (d, J=3.3, 1H), 7.2–7.6 (m, 5H).

Step B. Preparation of Nα,Nε-di-(3,4-Dihydroxybenzoyl)-L-lysine Benzyl Ester

The title compound was prepared from the product obtained in step A of this example (1.4 g, 3.3 mmol) according to the indications of general procedures C and D. The desired product was purified by flash chromatography using successively 30%, 50% and 90% EtOAc/CH$_2$Cl$_2$/1% AcOH as the eluent to give 444 mg, 26% of a yellow solid.

$^1$H NMR (DMSO-d$_6$): 1.4–1.8 (m, 4H), 3.4 (m, 4H), 4.6 (q, J=3.0, 1H), 5.2 (m, 2H), 6.7–7.5 (m, 11H), 7.6 (d, J=4.0, 1H), 7.7 (d, J=7.0, 1H), 9.0–10.0 (br s, 4×OH).

Step C. Preparation of Nα,Nε-di-(3,4-Dihydroxybenzoyl)-L-lysine

The product obtained in step B of this example (444 mg, 0.9 mmol) was hydrogenolysed on 10% Pd/C as described in general procedure E. Flash chromatography of the crude material using 99% EtOAc/1% AcOH and 5% MeOH/EtOAc/1% AcOH gave 253 mg (69%) of yellow crystals.

$^1$H NMR (DMSO-d$_6$): 1.4–1.8 (m, 4H), 3.4 (m, 4H), 4.6 (q, J=3.0, 1H), 6.7–7.5 (d, J=4.0, 1H), 7.7 (d, J=7.0, 1H), 9.0–10.0 (br s, 4×OH), 12.0 (br s, OH).

Example 4

Preparation of N-[Nα-(2,4-Dihydroxypyrimidinyl-5-carbonyl)-L-tyrosyl]dopamine (Compound No. 4)

Step A. Preparation of N-[Nα-(tert-Butoxycarbonyl)-L-tyrosyl]dopamine

Nα-(tert-butoxycarbonyl)-L-tyrosyl (1.0 g, 3.6 mmol) was coupled with dopamine hydrochloride (1.0 g, 5.4 mmol) according to the indications of general procedure F. The crude material was purified by flash chromatography eluting with initially 15% then 30% EtOAc/CH$_2$Cl$_2$/1% AcOH and 10% MeOH/CH$_2$Cl$_2$/1% AcOH. N-[Nα-(tert-butoxycarbonyl)-L-tyrosyl]dopamine was obtained in 89% yield (1.3 g) as a white solid.

$^1$H NMR (acetone-d$_6$): 1.3 (s, 9H), 2.6 (s, 2H), 2.8 (m, 2H), 3.3 (m, 2H), 4.2 (d, J=2.9, 1H), 5.9 (d, J=3.5, 1H), 6.4–7.0 (m, 7H), 7.3 (s, 1H), 8.2 (br s, 3×OH).

Step B. Preparation of N-[Nα-(2,4-Dihydroxypyrimidinyl-5-carbonyl)-L-tyrosyl]dopamine The title compound was prepared from the product obtained in step A of this example (494 mg, 1.2 mmol) according to the indications of general procedures C and D. The crude material was purified by flash chromatography using 30% EtOAc/CH$_2$Cl$_2$ and 10% MeOH/CH$_2$Cl$_2$ as the eluent. The final product was obtained as yellow crystals (108 mg, 20%). LC-MS: 455 (M++H); >95% pure Example 5

Preparation of N-(Nα,Nε-Dicaffeoyl-L-lysyl)dopamine (Compound No. 5)

Step A. Preparation of N-[Nα,Nε-di-(tert-Butoxycarbonyl)-L-lysyl]dopamine

The title compound was prepared from Nα,Nε-di-(tert-butoxycarbonyl)-L-lysine (951 mg, 2.8 mmol) according to general procedure F. The crude material was purified by flash chromatography using 30% EtOAc/CH$_2$Cl$_2$ containing 1% AcOH. The product was obtained as white crystals (1.0 g, 82%).

$^1$H NMR (acetone-d$_6$): 1.2–1.8 (m, 24H), 2.6 (t, J=3.4, 2H), 3.1, q, J=3.0, 2H), 3.2–3.6 (m, 2H), 4.0 (s, 1H), 6.0 (s, 1H), 6.5–6.8 (m, 4H), 7.2 (s, 1H), 7.6 and 7.8 (2×s, 2×OH).

Step B. Preparation of N-(Nα,Nε-Dicaffeoyl-L-lysyl)dopamine

N-(Nα,Nε-dicaffeoyl-L-lysyl)dopamine was prepared from the product obtained in step A of this example according to the general procedures C and D. The crude material was purified by flash chromatography eluting with initially 50% then 70% EtOAc/CH$_2$Cl$_2$ containing 1% AcOH and 5% MeOH/EtOAc containing 1% AcOH. The final product was obtained as yellow crystals (534 mg, 35%).

$^1$H NMR (DMSO-d$_6$): 1.2–1.8 (m, 6H), 2.5 (s, 2H), 3.2 (m, 4H), 4.2 (s, 1H), 6.3–7.3 (m, 13H), 8.0 (m, 3H), 9.6 (br s, 6H).

Example 6

Preparation of Nα,Nε-Dicaffeoyl-L-lysine Benzyl Ester (Compound No. 6)

The title compound was prepared from Nα,Nε-di-(tert-butoxycarbonyl)-L-lysine benzyl ester (3.0 g, 7.0 mmol, example 3, step A) according to the indications of general procedures C and D. The desired product was obtained as a yellow powder (1.23 g, 32%) after purification by flash chromatography using successively 30%, 50% and 99% EtOAc/CH$_2$Cl$_2$/1% AcOH as the eluent.

$^1$H NMR (DMSO-d$_6$): 1.4–1.9 (m, 6H), 3.2 (s, 2H), 4.5 (s, 1H), 5.2 (s, 2H), 6.3–7.8 (m, 15H), 8.0 (s, 1H), 8.4 (s, 1H), 9.5 (br s, 4×OH).

Example 7

Preparation of N-(Nα-Caffeoyl-Nγ-trityl-L-asparagyl)dopamine (Compound No. 7)

Step A. Preparation of N-[Nα-(9-Fluorenylmethoxycarbonyl)-Nγ-trityl-L-asparagyl]dopamine The title compound was prepared from Nα-(9-fluorenylmethoxycarbonyl)-Nγ-trityl-L-asparagine (2.0 g, 3.4 mmol) following the indications of general procedure F with dopamine hydrochloride (954 mg, 5 mmol). The crude material was purified by flash chromatography with a solvent gradient from 15% to 60% EtOAc/CH$_2$Cl$_2$ to give 2.3 g (95%) of the desired product as white crystals.

$^1$H NMR (DMSO-d$_6$): 2.5 (s, 2H), 2.6 (m, 2H), 3.2 (m, 2H), 4.2–4.5 (m, 3H), 6.3–7.5 (m, 29H), 7.6 (d, J=4.0, 1H), 7.7 (d, J=3.6, 1H), 7.9 (t, J=3.8, 1H), 8.6–8.8 (2×s, 2×OH).

Step B. Preparation of N-(Nα-Caffeoyl-Nγ-trityl-L-asparagyl)dopamine

N-[Nα-(9-fluorenylmethoxycarbonyl)-Nγ-trityl-L-asparagyl]dopamine (1.0 g, 1.5 mmol) was deprotected according to the indications of general procedure G. The intermediate was coupled with caffeic acid (348 mg, 2.2 mmol) following general procedure D. The crude material was purified by flash chromatography using a solvent gradient from 30% to 70% EtOAc/CHCl$_3$ containing 1% AcOH. The final product was obtained as yellow powder (400 mg, 44%).

$^1$H NMR (DMSO-d$_6$): 2.5 (s, 2H), 2.6 (d, J=2.9, 2H), 3.2 (s, 2H), 4.6 (d, J=2.5, 1H), 6.4–7.4 (m, 23H), 7.9 (s, 1H), 8.3 (d, J=3.8, 1H), 8.5 (s, 1H), 9.2 (br s, 4×OH).

Example 8

Preparation of N-[Nα-(3,4-Dihydroxybenzoyl)-Nγ-trityl-L-asparagyl]dopamine (Compound No. 8)

The title compound was prepared from N-[Nα-(9-fluorenylmethoxycarbonyl)-Nγ-trityl-L-asparagyl]dopamine (1.3 g, 1.7 mmol, example 7, step A) as described for example 7 (step B) using 3,4-dihydroxybenzoic acid (402 mg, 2.6 mmol) instead of caffeic acid. The crude material was purified by flash chromatography using a solvent gradient from 30% to 60% EtOAc/CH$_2$Cl$_2$ containing 1% AcOH. The title compound was obtained as white crystals (579 mg, 52%).

$^1$H NMR (DMSO-d$_6$): 2.4–2.9 (m, 4H), 3.2 (m, 2H), 4.7 (s, 1H), 6.4–7.3 (m, 21H), 7.8 (s, 1H), 8.3 (d, J=2.6, 1H), 8.5 (s, 1H), 9.0 (br s, 4×OH).

Example 9

Preparation of N-[Nα-(3,4-Dihydroxybenzoyl)-O-benzyl-L-threonyl]dopamine (Compound No. 9)

Step A. Preparation of N-[Nα-(tert-Butoxycarbonyl)-O-benzyl-L-threonyl]dopamine

The title compound was prepared from Nα-(tert-butoxycarbonyl)-O-benzyl-L-threonine (2.0 g, 6.5 mmol) following the indications of general procedure F using dopamine hydrochloride (2.4 g, 9.7 mmol). The crude material was purified by flash chromatography eluting with 30% EtOAc/CHCl$_3$ to give 2.8 g (98%) of the desired product as white crystals.

$^1$H NMR (DMSO-d$_6$): 1.4 (s, 12H), 2.6 (t, J=6.5, 2H), 3.4 (d, J=5.7, 2H), 4.5 (s, 1H), 5.1 (s, 2H), 5.7 (d, J=7.0, 1H), 6.5–7.4 (m, 10H), 8.0 (s, 2×OH).

Step B. Preparation of N-[Nα-(3,4-Dihydroxybenzoyl)-O-benzyl-L-threonyl]dopamine The product obtained in step A of this example (817 mg, 1.8 mmol) was deprotected according to the indications of general procedure C. The resulting intermediate was coupled with 3,4-dihydroxybenzoic acid (430 mg, 2.8 mmol) following the indications of general procedure D. The crude material was purified by flash chromatography using 30% EtOAc/CHCl$_3$ and 5% MeOH/CHCl$_3$ as the eluent. The final product was obtained as white crystals (271 mg, 31%).

$^1$H NMR (DMSO-d$_6$): 1.2 (d, J=3.0, 3H), 2.5 (t, J=3.9, 2H), 3.2 (m, 2H), 4.0 (t, J=2.7, 1H), 4.5 (m, 3H), 6.4–7.4 (m, 13H), 7.6 (d, J=4.4, 1H), 8.2 (s, 1H), 8.6–9.5 (4×s, 4×OH).

Example 10

Preparation of N-(Nα-Caffeoyl-O-benzyl-L-threonyl)dopamine (Compound No. 10)

The title compound was prepared from N-[Nα-(tert-butoxycarbonyl)-O-benzyl-L-threonyl]dopamine (1.0 g, 2.3 mmol, example 9, step A) as described for example 9 (step B) using caffeic acid (620 mg, 3.4 mmol) instead of 3,4-dihydroxybenzoic acid. The crude material was purified by flash chromatography using 30% EtOAc/CHCl$_3$ and 5% MeOH/CHCl$_3$ as the eluent. The title compound was obtained as yellow crystals (717 mg, 62%).

$^1$H NMR (DMSO-d$_6$): 1.2 (d, J=5.7, 3H), 2.5 (t, J=8.9, 2H), 3.2 (d, J=6.4, 2H), 3.9 (d, J=4.8, 1H), 4.5 (m, 3H), 6.4–7.4 (m, 13H), 8.0 (m, 2H), 8.6–9.4 (4×s, 4×OH).

Example 11

Preparation of N-(Nα,Nδ-Dicaffeoyl-L-ornithyl)dopamine (Compound No. 11)

Step A. Preparation of N-(Nα-tert-Butoxycarbonyl-Nδ-benzyloxycarbonyl-L-ornithyl)dopamine The title compound was prepared from Nα-tert-butoxycarbonyl-Nδ-benzyloxycarbonyl-L-ornithine (1.5 g, 4.0 mmol) following the indication of general procedure F using dopamine hydrochloride (1.2 g, 6.0 mmol). The final product was obtained as white crystals (1.5 g, 74%) after purification by flash chromatography with initially 30% then 50% EtOAc/CH$_2$C$_2$ as the eluent.

¹H NMR (DMSO-d₆): 1.3–1.7 (m, 13H), 2.5 (s, 2H), 2.9 (d, J=2.7, 2H), 3.2 (m, 2H), 3.8 (d, J=2.0, 1H), 5.0 (s, 2H), 6.3–7.4 (m, 8H), 6.7 (d, J=4.0, 1H), 7.2 (s, 1H), 7.8 (s, 1H), 8.6–8.8 (2×s, 2×OH).

Step B. Preparation of N-(Nα,Nδ-Dicaffeoyl-L-ornithyl) dopamine

N-(Nα-caffeoyl-Nδ-benzyloxycarbonyl-L-ornithyl) dopamine (1.3 g, 2.6 mmol) was completely deprotected following the indications of general procedures E and C. The free amino groups thus obtained were coupled with caffeic acid (1.2 g, 6.4 mmol) following the general procedure G. The crude material was purified by flash chromatography using a solvent gradient from 50% to 90% EtOAc/CH₂Cl₂/1% AcOH and 5% MeOH/EtOAc/1% AcOH. The desired product was obtained as yellow crystals (300 mg, 25%).

LC-MS: 592 (M⁺+H); >90% pure.

Example 12

Preparation of N-(Nα-Caffeoyl-S-trityl-L-cysteinyl) dopamine (Compound No. 12)

Step A. Preparation of N-(Nα-tert-Butoxycarbonyl-S-trityl-L-cysteinyl)dopamine

Commercially available Nα-tert-butoxycarbonyl-S-trityl-L-cysteine (3.0 g, 6.5 mmol) was coupled with dopamine hydrochloride (1.8 g, 9.7 mmol) as described in general procedure F. The crude material was purified by flash chromatography using a solvent gradient from 10% to 30% EtOAc/CH₂Cl₂. The product was obtained as white crystals (3.0 g, 80%).

¹H NMR (DMSO-d₆): 1.3 (s, 9H), 2.3–2.6 (m, 4H), 3.2 (m, 2H), 3.9 (d, J=3.0, 1H), 6.3–7.4 (m, 19H), 7.8 (s, 1H), 8.6 and 8.7 (2×s, 2×OH).

Step B. Preparation of N-(Nα-Caffeoyl-S-trityl-L-cysteinyl) dopamine

The product obtained in step A of this example (1.2 g, 2.0 mmol) was deprotected according to the indications of general procedure C. The crude intermediate was coupled with caffeic acid (441 mg, 2.5 mmol) according to procedure D. The crude product was purified by flash chromatography using a solvent gradient from 10% to 30% EtOAc/CH₂Cl₂ containing 1% AcOH to give 426 mg (50%) of a yellow powder.

¹H NMR (DMSO-d₆): 2.3–2.4 (m, 2H), 2.5 (d, J=6.0, 2H), 3.1–3.2 (m, 2H), 4.5 (m, 1H), 6.4–7.4 (m, 23H), 8.0 (s, 1H), 8.2 (s, 1H), 8.6–9.4 (4×s, 4×OH).

Example 13

Preparation of N-(Nα-Caffeoyl-Nτ-trityl-L-histidinyl)dopamine (Compound No. 13)

Step A. Preparation of N-[Nα-(9-Fluorenylmethoxycarbonyl)-Nτ-trityl-L-histidinyl] dopamine Commercially available Nα-(9-fluorenylmethoxycarbonyl)-Nτ-trityl-L-histidine (3.5 g, 5.6 mmol) was coupled with dopamine hydrochloride (1.6 g, 8.5 mmol) as described in general procedure F. The crude material was purified by flash chromatography using a solvent gradient from 20% to 80% EtOAc/CH₂Cl₂ containing 1% AcOH. The product was obtained as white crystals (2.2 g, 52%).

¹H NMR (DMSO-d₆): 2.5 (s, 2H), 2.7–2.9 (m, 2H), 3.2 (s, 2H), 4.2 (m, 4H), 6.6–7.7 (m, 28H), 8.0 (s, 1H), 8.6–8.8 (br s, 2×OH).

Step B. Preparation of N-(Nα-Caffeoyl-Nτ-trityl-L-histidinyl)dopamine

The product obtained in step A of this example (555 mg, 0.75 mmol) was deprotected according to the indications of general procedure G. The crude intermediate was coupled with caffeic acid (203 mg, 1.1 mmol) according to procedure D. The crude product was purified by flash chromatography using a solvent gradient from 10% to 99% EtOAc/CH₂Cl₂ containing 1% AcOH and 5% MeOH/EtOAc/CH₂Cl₂ to give 152 mg (30%) of a yellow powder.

¹H NMR (DMSO-d₆): 2.5 (t, J=3.8, 2H), 2.7–2.9 (m, 2H), 3.2 (q, J=3.5, 2H), 4.6 (q, J=3.0, 1H), 6.4–7.4 (m, 25H), 8.0 (t, J=3.4, 1H), 8.2 (d, J=4.0, 1H), 9.5 (br s, 4×OH).

Example 14

Preparation of N-[Nα-(3,4-Dihydroxybenzoyl)-Nτ-trityl-L-histidinyl]dopamine (Compound No. 14)

The title compound was prepared from N-[Nα-(9-fluorenylmethoxycarbonyl)-Nτ-trityl-L-histidinyl] dopamine (371 mg, 0.5 mmol, example 13, step A) as described for example 13 (step B) using 3,4-dihydroxybenzoic acid (114 mg, 0.7 mmol) instead of caffeic acid. The crude material was purified by flash chromatography using a solvent gradient from 50% to 99% EtOAc/CH₂Cl₂/1% AcOH and 5% MeOH/CHCl₃/1% AcOH. The title compound was obtained as a maroon powder (131 mg, 40%).

¹H NMR (DMSO-d₆): 2.5 (t, J=3.9, 2H), 2.9 (m, 2H), 3.2 (m, 2H), 4.6 (m, 1H), 6.4–7.7 (m, 23H), 8.0 (s, 1H), 8.2 (d, J=3.8, 1H), 9.2 (br s, 4×OH).

Example 15

Preparation of N-[Nα-(4-Hydroxy-3-nitrobenzoyl)-L-3,4-dihydroxyphenylalanyl]dopamine (Compound No. 15)

Step A. N-[Nα-(tert-Butoxycarbonyl)-L-3,4-dihydroxyphenylalanyl]dopamine

The title compound was prepared from L-3,4-dihydroxyphenylalanine (DOPA, 5.4 g, 27.6 mmol) as described in general procedures A and F. In general example A, di-tert-butyl-dicarbonate was used to give the desired Nα-(tert-butoxycarbonyl)-L-3,4-dihydroxyphenylalanine intermediate in 79% yield. The latter (858 mg, 2.9 mmol) was coupled with dopamine hydrochloride (820 mg, 4.3 mmol) following the indications of general procedure F. Purification by flash chromatography using 30% EtOAc/CH₂Cl₂ and 5% MeOH/CH₂Cl₂ gave 998 mg (80%) of the desired compound.

¹H NMR (acetone-d₆): 1.3 (s, 9H), 2.5 (d, J=3.3, 2H), 2.7–3.0 (2q, J=2.9, 3.6, 2H), 3.4 (m, 2H), 4H)(d, J=3.0 3.4, 1H), 6.5–6.8 (m, 6H), 7.2 (s, 1H), 8.2 (br s, 4×OH).

Step B. Preparation of N-[Nα-(4-Hydroxy-3-nitrobenzoyl)-L-3,4-dihydroxyphenylalanyl]dopamine The title compound was prepared by cleaving the Boc protective group (general procedure C) of the product prepared in step A of this example (958 mg, 2.2 mmol) and coupling it with 4-hydroxy-3-nitrobenzoic acid as described in general procedure D. Purification by HPLC using a solvent gradient from 100% water/0% acetonitrile to 100% acetonitrile containing 0.1% TFA, yielded the desired product as a yellow solid (441 mg, 40%).

LC-MS: 498 (M⁺+H); >90% pure.

Example 16

Preparation of N-[Nα-(3,4-Dihydroxybenzoyl)-Nτ-trityl-D-histidinyl]dopamine (Compound No. 16)

Step A. Preparation of N-[Nα-(9-Fluorenylmethoxycarbonyl)-Nτ-trityl-D-histidinyl] dopamine Commercially available Nα-(9-fluorenylmethoxycarbonyl)-Nτ-trityl-D-histidine (3.0 g, 4.8 mmol) was coupled with dopamine hydrochloride (1.4 g, 7.3 mmol) as described in general procedure F. The crude material was purified by flash chromatography eluting with initially 50% then 99% EtOAc/CH$_2$Cl$_2$/1% AcOH and 5% MeOH/EtOAc/1% AcOH. The product was obtained as white crystals (1.98 g, 54%).

$^1$H NMR (DMSO-d$_6$): 2.5 (s, 2H), 2.7–2.9 (m, 2H), 3.2 (s, 2H), 4.2 (m, 4H), 6.4 (s, 1H), 6.6–7.7 (m, 28H), 8.0 (s, 1H), 8.6–8.8 (br s, 2×OH).

Step B. Preparation of N-[Nα-(3,4-Dihydroxybenzoyl)-Nτ-trityl-D-histidinyl]dopamine The product obtained in step A of this example (654 mg, 0.8 mmol) was deprotected according to the indications of general procedure G. The crude intermediate was coupled with 3,4-dihydroxybenzoic acid (198 mg, 1.3 mmol) according to procedure D. The crude product was purified by flash chromatography using a solvent gradient from 50% to 99% EtOAc/CH$_2$Cl$_2$/1% AcOH and 5% MeOH/EtOAc/1% AcOH to give 40 mg (7%) of a maroon powder.

$^1$H NMR (DMSO-d$_6$): 2.5 (t, J=3.9, 2H), 2.9 (m, 2H), 3.2 (m, 2H), 4.6 (m, 1H), 6.4–7.7 (m, 23H), 8.0 (s, 1H), 8.2 (d, J=3.8, 1H), 9.2 (br s, 4×OH).

Example 17

Preparation of N-[Nα-(4-Hydroxy-3-nitrobenzoyl)-Nτ-trityl-L-histidinyl]dopamine (Compound No. 17)

The title compound was prepared from N-[Nα-(9-fluorenylmethoxycarbonyl)-Nτ-trityl-L-histidinyl]dopamine (763 mg, 1.0 mmol, example 13, step A) as described for example 13 (step B) using 4-hydroxy-3-nitrobenzoic acid (280 mg, 1.5 mmol) instead of caffeic acid. The crude material was purified by flash chromatography using 50% EtOAc/CH$_2$Cl$_2$/1% AcOH and 100% EtOAc as the eluent. The title compound was obtained as a yellow powder (245 mg, 35%).

$^1$H NMR (DMSO-d$_6$): 2.5 (d, J=3.4, 2H), 2.8–3.0 (m, 2H), 3.2 (m, 2H), 4.6 (m, 1H), 6.3–7.3 (m, 23H), 7.9 (d, J=4.3, 1H), 8.0 (s, 1H), 8.4–9.0 (br s, 3×OH).

Example 18

Preparation of N-[Nα-(4-Hydroxy-3-nitrobenzoyl)-Nτ-trityl-D-histidinyl]dopamine (Compound No. 18)

The title compound was prepared from N-[Nα-(9-fluorenylmethoxycarbonyl)-Nτ-trityl-D-histidinyl]dopamine (734 mg, 0.97 mmol, example 16, step A) as described for example 16 (step B) using 4-hydroxy-3-nitrobenzoic acid (267 mg, 1.5 mmol) instead of 3,4-dihydroxybenzoic acid. The crude material was purified by flash chromatography using initially 30% then 50% EtOAc/CH$_2$Cl$_2$/1% AcOH and 100% EtOAc as the eluent. The title compound was obtained as a yellow powder (230 mg, 34%).

$^1$H NMR (DMSO-d$_6$): 2.4 (t, J=6.9, 2H), 2.9 (m, 2H), 3.2 (m, 2H), 4.6 (m, 1H), 6.4–8.7 (m, 23H), 7.9 (d, J=8.7, 1H), 8.0 (s, 1H), 8.8 (br s, 3×OH).

Example 19

Preparation of N-[Nα-Caffeoyl-Nτ-(2,4-dinitrophenyl)-L-histidinyl]dopamine (Compound No. 19)

Step A. Preparation of N-[Nα-tert-Butoxycarbonyl-Nτ-(2,4-dinitrophenyl)-L-histidinyl]dopamine Commercially available Nα-tert-butoxycarbonyl-Nτ-(2,4-dinitrophenyl)-L-histidine (3.0 g, 6.2 mmol) was coupled with dopamine hydrochloride (1.8 g, 9.3 mmol) as described in general procedure F. The crude material was purified by flash chromatography using a solvent gradient from 30% to 80% EtOAc/CH$_2$Cl$_2$/1% AcOH and 2.5% MeOH/EtOAc/1% AcOH. The product was obtained as white crystals (2.0 g, 56%).

$^1$H NMR (DMSO-d$_6$): 1.3 (s, 9H), 2.5 (d, J=4.4, 2H), 2.7–2.9 (m, 2H), 3.1–3.3 (m, 2H), 4.2 (d, J=2.5, 1H), 6.3–7.6 (m, 8H), 7.9 (d, J=4.0, 1H), 8.0 (s, 1H), 8.7 and 9.0 (2×s, 2×OH).

Step B. Preparation of N-[Nα-Caffeoyl-Nτ-(2,4-dinitrophenyl)-L-histidinyl]dopamine The product obtained in step A of this example (317 mg, 0.6 mmol) was deprotected according to the indications of general procedure C. The crude intermediate was coupled with caffeic acid (154 mg, 0.9 mmol) according to procedure D. The crude product was purified by flash chromatography using a solvent gradient from 50% to 99% EtOAc/CH$_2$Cl$_2$/1% AcOH and 5% MeOH/EtOAc/1% AcOH to give 120 mg (34%) as yellow crystals.

$^1$H NMR (DMSO-d$_6$): 2.5 (s, 2H), 2.8–3.0 (m, 2H), 3.2 (m, 2H), 4.6 (m, 1H), 6.4–8.2 (m, 13H), 8.6 (d, J=4.5, 1H), 8.9 (s, 1H), 10.0 (br s, 4×OH).

Example 20

Preparation of Nα-(4-Amino-3-hydroxybenzoyl)-L-3,4-dihydroxyphenylalanine (Compound No. 20)

Step A. Preparation of Nα-tert-Butoxycarbonyl-L-3,4-dibenzyloxyphenylalanine Benzyl Ester The title compound was prepared from Nα-(tert-butoxycarbonyl)-L-3,4-dihydroxyphenylalanine (2.0 g, 6.7 mmol, example 15, intermediate of step A) by following the general procedure B (b). The crude material was purified by flash chromatography using successively 10%, 35% and 45% EtOAc/CH$_2$Cl$_2$/1% AcOH. The product was isolated as a yellow solid (3.0 g, 79% yield).

$^1$H NMR (DMSO-d$_6$): 1.4 (s, 9H), 3.0 (d, J=4.9, 2H), 4.0 (s, 1H), 4.9 (s, 1H), 5.0–5.1 (m, 6H), 6.5–7.4 (m, 18H).

Step B. Preparation of Nα-(3-Hydroxy-4-nitrobenzoyl)-L-3,4-dibenzyloxyphenylalanine Benzyl Ester (Compound No. 30)

The product obtained in step A of this example (2.5 g, 4.4 mmol) was deprotected according to the indications of general procedure C. The crude intermediate was coupled with 3-hydroxy-4-nitrobenzoic acid (976 mg, 5.3 mmol) according to procedure D. The crude product was purified by flash chromatography eluting successively with 20% and 25% EtOAc/hexane to give 1.0 g (40%) as yellow crystals.

$^1$H NMR (DMSO-d$_6$): 3.0 (m, 2H), 4.7 (m, 1H), 5.0–5.2 (m, 6H), 6.5–7.6 (m, 21H), 8.0 (d, J=7.6, 1H), 11.3 (s, OH).

Step C. Preparation of Nα-(4-Amino-3-hydroxybenzoyl)-L-3,4-dihydroxyphenylalanine The title product was obtained from Nα-(3-hydroxy-4-nitrobenzoyl)-L-3,4-dibenzyloxyphenylalanine benzyl ester (300 mg, 0.5 mmol) prepared in step B of this example by following the indications of general procedure E. The crude material was purified by flash chromatography eluting initially with 50% then 80% EtOAc/CH$_2$Cl$_2$/1% AcOH and 5% MeOH/EtOAc/1% AcOH to yield 129 mg, 82% of the desired product as a yellow powder.

LC-MS: 333 (M$^+$+H); >90% pure.

Example 21

Preparation of N-[Nα-(3,4-Dihydroxybenzoyl)-Nτ-(2,4-dinitrophenyl)-L-histidinyl]dopamine (Compound No. 21)

N-[Nα-tert-butoxycarbonyl-Nτ-(2,4-dinitrophenyl)-L-histidinyl]dopamine obtained in step A of example 19 (1.2 g, 2.2 mmol) was deprotected according to the indications of general procedure C. The crude intermediate was coupled with 3,4-dihydroxybenzoic acid (499 mg, 3.2 mmol) according to procedure D. The crude product was purified by flash chromatography eluting with 50% EtOAc/CH$_2$Cl$_2$/1% AcOH and 5% MeOH/EtOAc/1% AcOH to give 473 mg (37%) as a yellow powder.

$^1$H NMR (DMSO-d$_6$): 2.5 (s, 2H), 3.0 (d, J=5.9, 2H), 3.2 (m, 2H), 4.7 (m, 1H), 6.4–8.2 (m, 11H), 8.6 (d, J=9.3, 1H), 8.9 (s, 1H), 10.0 (br s, 4×OH).

Example 22

Preparation of N-[Nα-(9-Fluorenylmethoxycarbonyl)-Nτ-trityl-L-histidinyl]-3,4-dihydroxybenzylamine (Compound No. 22)

The title compound was prepared from commercially available Nα-(9-fluorenylmethoxycarbonyl)-Nτ-trityl-L-histidine (3.5 g, 5.7 mmol) by following general procedure F using 3,4-dihydroxybenzylamine hydrobromide (1.9 g, 8.5 mmol). The mixture was stirred at room temperature for 2 h. The crude material was purified by flash chromatography using a solvent gradient from 20% to 90% EtOAc/CH$_2$Cl$_2$ containing 1% AcOH. The product was isolated as a white powder (2.3 g, 54% yield).

$^1$H NMR (DMSO-d$_6$): 2.6–2.7 (m, 2H), 2.9 (m, 2H), 3.5 (m, 1H), 4.1 (d, J=2.4, 2H), 4.2 (s, 1H), 6.3–7.9 (m, 30H), 8.1 and 8.2 (2×s, 2×OH).

Example 23

Preparation of N-[Nα-(3,4-Dihydroxybenzoyl)-Nτ-(2,4-dinitrophenyl)-L-histidinyl]-3,4-dihydroxybenzylamine (Compound No. 23)

Step A. Preparation of N-[Nα-tert-Butoxycarbonyl-Nτ-(2,4-dinitrophenyl)-L-histidinyl]-3,4-dihydroxybenzylamine (Compound No. 24)

Commercially available Nα-tert-butoxycarbonyl-Nτ-(2,4-dinitrophenyl)-L-histidine (3.0 g, 6.0 mmol) was coupled with 3,4-dihydroxybenzylamine hydrobromide (2.0 g, 9.4 mmol) as described in general procedure F. The crude material was purified by flash chromatography using a solvent gradient from 15% to 90% EtOAc/CH$_2$Cl$_2$/1% AcOH and another solvent gradient from 2.5% to 5% MeOH/EtOAc/1% AcOH. The product was obtained as yellow powder (1.4 g, 40%).

$^1$H NMR (DMSO-d$_6$): 1.4 (s, 9H), 2.7–2.9 (m, 2H), 4.0–4.4 (m, 3H), 6.4–7.7 (m, 8H), 7.8 (d, J=4.3, 1H), 7.9UJ=4.3, 1H), 7.9 (s, 1H), 8.2×OH).

Step B. Preparation of N-[Nα-(3,4-Dihydroxybenzoyl)-Nτ-(2,4-dinitrophenyl)-L-histidinyl]-3,4-dihydroxybenzylamine The product obtained in step A of this example (780 mg, 1.4 mmol) was deprotected according to the indications of general procedure C. The crude intermediate was coupled with 3,4-dihydroxybenzoic acid (332 mg, 2.2 mmol) according to procedure D. The crude product was purified by flash chromatography using a solvent gradient from 50% to 99% EtOAc/CH$_2$Cl$_2$/1% AcOH and 5% MeOH/EtOAc/1% AcOH to give 250 mg (30%) as yellow crystals.

$^1$H NMR (DMSO-d$_6$): 3.0 (s, 2H), 4.2 (s, 2H), 4.7 (d, J=3.0, 1H), 6.4–8.3 (m, 11H), 8.6 (d, J=4.4, 1H), 8.9 (s, 1H), 9.5 (br s, 4×OH).

Example 24

Preparation of N-[Nα-tert-Butoxycarbonyl-Nτ-(2,4-dinitrophenyl)-L-histidinyl]-3,4-dihydroxybenzylamine (Compound No. 24)

The preparation of this compound was described above in example 23, step A.

Example 25

Preparation of N-[Nα-(3,4-Dihydroxybenzoyl)-Nτ-trityl-L-histidinyl]-3,4-dihydroxybenzylamine (Compound No. 25)

The title compound was prepared from N-[Nα-(9-fluorenylmethoxycarbonyl)-Nτ-trityl-L-histidinyl]-3,4-dihydroxybenzylamine (example 22, 1.0 g, 1.4 mmol) was deprotected according to the indications of general procedure G. The product thus obtained was then coupled with 3,4-dihydroxybenzoic acid (312 mg, 2.0 mmol) according to the indications of general procedure D. The reaction mixture was heated at 60° C. for 4 h. The crude product was purified by flash chromatography using 50% EtOAc/CH$_2$Cl$_2$/1% AcOH and 5% MeOH/EtOAc/1% AcOH to give the desired product (200 mg, 23%) as yellow crystals.

$^1$H NMR (DMSO-d$_6$): 3.0 (d, J=2.8, 2H), 4.1 (d, J=4.9, 2H), 4.7 (m, 1H), 6.4–7.4 (m, 23H), 8.1 (d, J=7.9, 1H), 8.2 (s, 1H), 9.6 (br s, 4×OH).

Example 26

Preparation of N-[Nα-(4-Hydroxy-3-nitrobenzoyl)-Nδ-methyltrityl-L-glutaminyl]-3,4-dihydroxybenzylamine (Compound No. 26)

Step A. Preparation of N-[Nα-(9-Fluorenylmethoxycarbonyl)-Nδ-methyltrityl-L-glutaminyl]-3,4-dihydroxybenzylamine Commercially available Nα-(9-fluorenylmethoxycarbonyl)-Nδ-methyltrityl-L-glutamine (3.0 g, 4.8 mmol) was coupled with 3,4-dihydroxybenzylamine hydrobromide (1.58 g, 7.2 mmol) as described in general procedure F. The crude material was purified by flash chromatography eluting successively with 15%, 30% and 50% EtOAc/CH$_2$Cl$_2$ containing 1% AcOH. The product was obtained as white powder (3.0 g, 84%).

$^1$H NMR (DMSO-d$_6$): 1.6–1.9 (m, 2H), 2.2 (s, 3H), 2.3 (m, 2H), 4.0 (m, 2H), 4.1 (d, J=4.3, 2H), 4.3 (m, 2H), 6.5–7.8 (m, 25 H), 7.9 (d, J=7.5, 2H), 8.1 (s, 1H), 8.8 (br s, 2×OH).

Step B. Preparation of N-[Nα-(4-Hydroxy-3-nitrobenzoyl)-Nδ-methyltrityl-L-glutaminyl]-3,4-dihydroxybenzylamine The product obtained in step A of this example (401 mg, 0.54 mmol) was deprotected according to the indications of general procedure G. The product thus obtained was then coupled with 4-hydroxy-3-nitrobenzoic acid (147 mg, 0.8 mmol) according to the indications of general procedure D. The reaction mixture was heated at 60° C. for 4 h. The crude product was purified by flash chromatography using successively 10%, 30% and 60% EtOAc/CH$_2$Cl$_2$/1% AcOH to give the desired product (80 mg, 22%) as yellow crystals.

$^1$H NMR (DMSO-d$_6$): 1.8–2.0 (m, 2H), 2.2 (s, 3H), 2.4 (q, J=7.9. 2H), 4.1 (d, J=5.0, 2H), 4.4 (m, 1H), 6.5–8.6 (m, 21H), 8.0 (d, J=9.3, 1H), 8.3 (t, J=5.8, 1H), 8.7 and 8.8 (2×s, 2×OH), 11.7 (br s, OH).

Example 27

Preparation of N-(Nα-Dihydrocaffeoyl-Nτ-trityl-L-histidinyl)dopamine (Compound No. 27)

The title compound was prepared from N-[Nα-(9-fluorenylmethoxycarbonyl)-Nτ-trityl-L-histidinyl] dopamine (456 mg, 0.6 mmol, example 13, step A) as described for example 13 (step B) using dihydrocaffeic acid (165 mg, 0.9 mmol) instead of caffeic acid. The crude material was purified by flash chromatography using 50% EtOAc/CH$_2$Cl$_2$/1% AcOH and 5% MeOH/CHCl$_3$/1% AcOH as the eluent. The title compound was obtained as white crystals (151 mg, 36%).

¹H NMR (DMSO-d₆): 2.1–2.3 (m, 2H), 2.4–2.5 (m, 4H), 2.6–2.8 (m, 2H), 3.1 (d, J=3.0, 2H), 4.4 (q, J=2.8, 1H), 6.4–7.5 (m, 23H), 7.7 (t, J=2.5, 1H), 7.9 (d, J=3.9, 1H), 8.8 (br s, 4×OH).

Example 28

Preparation of N-(Nα-Dihydrocaffeoyl-Nτ-methyltrityl-L-histidinyl)dopamine (Compound No. 28)

Step A. Preparation of N-[Nα-(9-Fluorenylmethoxycarbonyl)-Nτ-methyltrityl-L-histidinyl]dopamine Commercially available Nα-(9-fluorenylmethoxycarbonyl)-Nδ-methyltrityl-L-histidine (1.84 g, 2.9 mmol) was coupled with dopamine hydrochloride (827 mg, 4.36 mmol) as described in general procedure F. The crude material was purified by flash chromatography using a solvent gradient from 30% to 90% EtOAc/CH₂Cl₂/1% AcOH and 5% MeOH/EtOAc/1% AcOH. The product was obtained as white powder (1.23 g, 55%).

¹H NMR (DMSO-d₆): 2.2 (s, 3H), 2.35 (s, 2H), 2.7–2.9 (m, 2H), 3.2 (m, 2H), 4.2 (m, 4H), 6.4 (s, 1H), 6.6–7.8 (m, 27H), 8.0 (s, 1H), 8.5–8.9 (br s, 2×OH).

Step B. Preparation of N-(Nα-Dihydrocaffeoyl-Nτ-methyltrityl-L-histidinyl)dopamine The product obtained in step A of this example (534 mg, 0.7 mmol) was deprotected according to the indications of general procedure G. The product thus obtained was then coupled with dihydrocaffeic acid (189 mg, 1.0 mmol) according to the indications of general procedure D. The reaction mixture was heated at 60° C. for 4 h. The crude product was purified by flash chromatography using a solvent gradient from 30% to 90% EtOAc/CH₂Cl₂/1% AcOH and 5% MeOH/EtOAc/1% AcOH to give the desired product (100 mg, 20%) as yellow crystals.

¹H NMR (DMSO-d₆): 2.0–2.3 (m, 5H), 2.4–2.5 (m, 4H), 2.6–2.8 (m, 2H), 3.1 (d, J=6.0, 3H), 4.4 (q, J=3.0, 1H), 6.4–7.5 (m, 22H), 8.6 (d, J=8.0, 1H), 8.9 (s, 1H), 10.0 (br s, 4×OH).

Example 29

Nα-(3,4-Dihydroxybenzoyl)-Nτ-trityl-L-histidine (Compound No. 29)

Step A. Loading of the Resin

Commercially available Nα-(9-fluorenylmethoxycarbonyl)-Nτ-trityl-L-histidine was bound to a polystyrene 2-chlorotrityl resin by stirring in a DMF suspension for a period of 16 h at 23° C. under an inert atmosphere of argon. Afterwards, the resin is filtered before being washed in the following manner; 3 times with 20 mL DMF, 3 times with 20 mL methanol, 1 time with 20 mL DMF, 2 times with 20 mL methanol and finally, 3 times with 20 mL ether. The resulting resin was dried under vacuum.

Step B. Removal of the Fmoc Protective Group and Coupling of 3,4-Dihydroxybenzoic Acid The resin prepared in step A of this example (500 mg, containing 0.6 mmol of the histidine derivative) was stirred for 1 h at 23° C. under an inert atmosphere of argon in the presence of a 30% piperidine/DMF solution. The resulting histidine component is filtered and washed 3 times with 20 mL DMF, 2 times with 20 mL methanol and 2 times with 20 mL ether. The resulting histidine-bound resin with a free Nα amino group is then coupled to 3,4-dihydroxybenzoic acid (282 mg, 1.8 mmol) in the presence of HOBt (247 mg, 1.8 mmol) and EDC (350 mg, 1.8 mmol) in DMF at 60° C. for 4 h. Afterwards, the resin is filtered before being washed and dried in the same manner as described in step A of this example.

Step C. Release of the Histidine Derivative: Nα-(3,4-Dihydroxybenzoyl)-Nτ-trityl-L-histidine The final product is obtained by treatment of the intermediate of step B with a solution of AcOH/Trifluoroethanol/CH₂Cl₂ (1/1/8 (v/v)) at room temperature for 2 h. The resin is filtered and the final product is obtained by evaporation of the solvents. Purification by HPLC using a solvent gradient from 100% water/0% acetonitrile to 100% acetonitrile containing 0.1% TFA yielded 260 mg (40%) of the final product.

LC-MS: 534 (M⁺+H); >95% pure.

Example 30

Nα-(3-Hydroxy-4-nitrobenzoyl)-L-3,4-dibenzyloxyphenylalanine Benzyl Ester (Compound No. 30)

The preparation of this compound was already described in example 20 step B (vide supra).

Example 31

Preparation of N-(Nα-Caffeoyl-Nτ-trityl-L-histidinyl)-3,4-dihydroxybenzylamine (Compound No. 31)

The title compound was prepared from N-[Nα-(9-fluorenylmethoxycarbonyl)-Nτ-trityl-L-histidinyl]-3,4-dihydroxybenzylamine (555 mg, 0.7 mmol, example 22) was deprotected according to the indications of general procedure G. The product thus obtained was then coupled with caffeic acid (203 mg, 1.0 mmol) according to the indications of general procedure D. The reaction mixture was heated at 60° C. for 4 h. The crude product was purified by flash chromatography using a solvent gradient from 40% to 90% EtOAc/CH₂Cl₂/1% AcOH and 5% MeOH/EtOAc/1% AcOH to give the desired product (152 mg, 30%) as yellow crystals.

¹H NMR (DMSO-d₆): 2.7–3.0 (m, 2H), 4.1 (m, 2H), 4.6 (s, 1H), 6.4–7.4 (m, 25H), 8.0 (d, J=4.0, 1H), 8.4 (s, 1H), 9.5 (br s, 4×OH).

Example 32

Preparation of N-[Nα-(3,4-Dihydroxybenzoyl)-Nδ-methyltrityl-L-glutaminyl]-3,4-dihydroxybenzylamine (Compound No. 32)

The title compound was prepared from N-[Nα-(9-fluorenylmethoxycarbonyl)-Nδ-methyltrityl-L-glutaminyl]-3,4-dihydroxybenzylamine (576 mg, 0.8 mmol, example 26, step A) as described for example 26 (step B) using 3,4-dihydroxybenzoic acid (178 mg, 1.2 mmol) instead of 4-hydroxy-3-nitrobenzoic acid. The crude material was purified by flash chromatography using a solvent gradient from 30% to 60% EtOAc/CH₂Cl₂/1% AcOH. The title compound was obtained as white crystals (190 mg, 32%).

¹H NMR (DMSO-d₆): 1.8–2.0 (m, 2H), 2.2 (s, 3H), 2.4 (m, 2H), 4.2 (d, J=2.0, 2H), 4.4 (s, 1H), 6.5–7.3 (m, 20H), 8.0, 8.2 and 8.5 (3×s, 3H), 9.0 (br s, 4×OH).

Example 33

Preparation of N-(Nα-Caffeoyl-Nδ-methyltrityl-L-glutaminyl)-3,4-dihydroxybenzylamine (Compound No. 33)

The title compound was prepared from N-[Nα-(9-fluorenylmethoxycarbonyl)-Nδ-methyltrityl-L-glutaminyl]-

3,4-dihydroxybenzylamine (900 mg, 1.2 mmol, example 26, step A) as described for example 26 (step B) using caffeic acid (326 mg, 1.8 mmol) instead of 4-hydroxy-3-nitrobenzoic acid. The crude material was purified by flash chromatography using a solvent gradient from 30% to 70% EtOAc/CH$_2$Cl$_2$/1% AcOH. The title compound was obtained as a yellow powder (430 mg, 52%).

$^1$H NMR (DMSO-d$_6$): 1.8–2.0 (m, 2H), 2.2 (s, 3H), 2.3–2.4 (s, 2H), 4.0 (s, 2H), 4.3 (s, 1H), 6.2–7.0 (m, 22H), 7.6 (d, J=3.5, 1H), 7.8 (s, 1H), 8.2 (s, 1H), 8.5 (br s, 4×OH).

Example 34

Preparation of N-[Nα-(4-Hydroxy-3-nitrobenzoyl)-O-benzyl-L-seryl]dopamine (Compound No. 34)

Step A. Preparation of N-[Nα-(tert-Butoxycarbonyl)-O-benzyl-L-seryl]dopamine

The title compound was prepared from commercially available Nα-(tert-butoxycarbonyl)-O-benzyl-L-serine (2.0 g, 6.8 mmol) following the indications of general procedure F using dopamine hydrochloride (2.6 g, 10.0 mmol). The crude material was purified by flash chromatography eluting with 30% EtOAc/CH$_2$Cl$_2$ and 5% MeOH/CH$_2$Cl$_2$ to give 2.6 g (90%) of the desired product as yellow crystals.

LC-MS: 429 (M$^+$–H); >96% pure.

Step B. Preparation of N-[Nα-(4-Hydroxy-3-nitrobenzoyl)-O-benzyl-L-seryl]dopamine The product obtained in step A of this example (1.17 g, 2.7 mmol) was deprotected according to the indications of general procedure C. The resulting intermediate was coupled with 4-hydroxy-3-nitrobenzoic acid (747 mg, 4.0 mmol) following the indications of general procedure D. The crude material was purified by HPLC using a solvent gradient from 100% water/0% acetonitrile to 100% acetonitrile containing 0.1% TFA. The final product was obtained as yellow crystals (606 mg, 45%).

LC-MS: 496 (M$^+$+H); >90% pure.

Example 35

Preparation of N-(Nα-(3-Nitrocinnamoyl)-Nτ-trityl-L-histidinyl)dopamine (Compound No. 35)

The title compound was prepared from N-[Nα-(9-fluorenylmethoxycarbonyl)-Nτ-trityl-L-histidinyl]dopamine (594 mg, 0.8 mmol, example 13, step A) as described for example 13 (step B) using 3-nitrocinnamic acid (230 mg, 1.2 mmol) instead of caffeic acid. The crude material was purified by flash chromatography using successively 30%, 50% and 90% EtOAc/CH$_2$Cl$_2$/1% AcOH and 5% MeOH/EtOAc/1% AcOH as the eluent. The title compound was obtained as a yellow powder (200 mg, 36%).

$^1$H NMR (DMSO-d$_6$): 2.5 (t, J=8.0, 2H), 2.7–3.0 (ABX, J=13.8, 2H), 3.2 (d, J=5.6, 2H), 4.6 (d, J=5.0, 1H), 6.4–8.4 (M, 24H), 6.9 and 7.5 (2d, J=16.0, 2H), 8.0 (d, J=7.4, 1H), 8.1 (s, 1H), 8.8 (br s, 2×OH).

Example 36

Preparation of N-[Nα-(4-Hydroxy-3-nitrobenzoyl)-Nτ-methyltrityl-L-histidinyl]dopamine (Compound No. 36)

The title compound was prepared from N-[Nα-(9-fluorenylmethoxycarbonyl)-Nτ-methyltrityl-L-histidinyl]dopamine (1.1 g, 1.4 mmol, example 28, step A) as described for example 28 (step B) using 4-hydroxy-3-nitrobenzoic acid (394 mg, 2.0 mmol) instead of dihydro-caffeic acid. The crude material was purified by flash chromatography using a solvent gradient from 40% to 90% EtOAc/CH$_2$Cl$_2$/1% AcOH and 99% EtOAc/1% AcOH. The title compound was obtained as a yellow powder (176 mg, 19%).

$^1$H NMR (DMSO-d$_6$): 2.2 (s, 3H), 2.5 (s, 2H), 2.7–3.0 (m, 2H), 3.2–3.4 (m, 2H), 4.6 (s, 1H), 6.3–7.3 (m, 22H), 8.0 (m, 2H), 8.4–9.3 (br s, 3×OH).

Example 37

Preparation of N-[Nα-(2,4,6-Trihydroxybenzoyl)-Nε-benzyloxycarbonyl-L-lysyl]dopamine (Compound No. 37)

Step A. Preparation of N-[Nα-(tert-Butoxycarbonyl)-Nε-benzyloxycarbonyl-L-lysyl]dopamine The title compound was prepared from Nα-(tert-butoxycarbonyl)-Nε-benzyloxycarbonyl-L-lysine (1.5 g, 3.9 mmol) following the indications of general procedure F using dopamine hydrochloride (1.1 g, 5.9 mmol). The crude material was purified by flash chromatography eluting with 60% EtOAc/CH$_2$Cl$_2$ to give 1.7 g (87%) of the desired product as white crystals.

$^1$H NMR (DMSO-d$_6$): 1.4 (s, 9H), 2.5 (s, 2H), 3.0 (d, J=5.5, 2H), 3.1 (m, 2H), 3.8 (s, 1H), 5.0 (s, 2H), 6.3–7.4 (m 10H), 7.8 (s, 1H), 8.6 and 8.7 (2×s, 2×OH).

Step B. Preparation of N-[Nα-(2,4,6-Trihydroxybenzoyl)-Nε-benzyloxycarbonyl-L-lysyl]dopamine The product obtained in step A of this example (1.7 g, 3.3 mmol) was deprotected according to the indications of general procedure C. The resulting intermediate was coupled with gallic acid (1.0 g, 5.0 mmol) following the indications of general procedure D. The crude material was purified by flash chromatography using a solvent gradient from 20% to 60% EtOAc/CH$_2$Cl$_2$. The final product was obtained as white crystals (374 mg, 20%).

$^1$H NMR (DMSO-d$_6$): 1.2 (t, J=7.0, 2H), 1.4 (t, J=7.0, 2H), 1.5–1.6 (m, 2H), 2.5 (t, J=7.3, 2H), 2.94 (d, J=5.8, 2H), 2.98 (m, 2H), 4.4 (q, J=6.4, 1H), 4.9 (s, 2H), 5.7–7.4 (m, 12H), 8.2 (t, J=4.6, 1H), 9.0–12.6 (br s, 5×OH).

Example 38

Preparation of N-[Nα-(2-Fluoro-6-Hydroxybenzoyl)-S-trityl-L-cysteinyl]dopamine (Compound No. 38)

Commercially available Nα-(9-Fluorenylmethoxycarbonyl)-S-trityl-L-cysteine (1.7 g, 2.9 mmol) was coupled with dopamine hydrochloride (825 mg, 4.3 mmol) according to the indications of general procedure F. The crude N-[Nα-(9-fluorenylmethoxycarbonyl)-S-trityl-L-cysteinyl]dopamine (618 mg, 0.86 mmol) was deprotected according to the indications of general procedure G. The resulting intermediate was then coupled with 2-fluorosalicylic acid (202 mg, 1.3 mmol) according to the indications of general procedure D. The final product was purified by flash chromatography using 99% CH$_2$Cl$_2$/1% AcOH and successively 5% then 10% AcOEt/CH$_2$C$_2$/1% AcOH to yield the desired derivative (260 mg, 48%) as white crystals.

$^1$H NMR (DMSO-d$_6$): 2.4–2.6 (m, 2H), 3.1–3.3 (m, 2H), 3.4–3.5 (t, J=6.6, 2H), 4.5 (d, J=6.0, 1H), 6.4–7.5 (m, 21H), 8.0 (s, 1H), 8.4 (t, J=7.3, 1H), 8.7–11.8 (3×s, 3×OH).

Example 39

Preparation of N-[Nα-(3,4,5-Trihydroxybenzoyl)-Nτ-trityl-L-histidinyl]dopamine (Compound No. 39)

The title compound was prepared from N-[Nα-(9-fluorenylmethoxycarbonyl)-Nτ-trityl-L-histidinyl]

dopamine (1.07 g, 1.4 mmol, example 13, step A) as described for example 13 (step B) using gallic acid (362 mg, 2.1 mmol) instead of caffeic acid. The crude material was purified by flash chromatography using successively 35% then 50% EtOAc/CH$_2$Cl$_2$/1% AcOH followed by 99% EtOAc/1% AcOH and 5% MeOH/EtOAc/1% AcOH as the eluent. The title compound was obtained as a white powder (291 mg, 30%).

$^1$H NMR (DMSO-d$_6$): 2.4 (s, 2H), 2.9 (d, J=5.0, 2H), 3.1 (m, 2H), 4.5 (d, J=6.9, 1H), 6.4–7.3 (M, 22H), 7.9 (s, 1H), 8.1 (d, J=7.4, 1H), 9.0 (br s, 5×OH).

Example 40

Preparation of N-(Nα-Caffeoyl-Nτ-benzyl-L-histidinyl)dopamine (Compound No. 40)

Step A. Preparation of N-[Nα-(tert-Butoxycarbonyl)-Nτ-benzyl-L-histidinyl]dopamine The title compound was prepared from commercially available Nα-(tert-butoxycarbonyl)-Nτ-benzyl-L-histidine (2.0 g, 5.8 mmol) following the indications of general procedure F using dopamine hydrochloride (1.65 g, 8.7 mmol). The crude material was purified by flash chromatography eluting with 50% EtOAc/CH$_2$Cl$_2$ and 10% MeOH/EtOAc/1% AcOH to give 2.0 g (75%) of the desired product as white crystals.

$^1$H NMR (DMSO-d$_6$): 1.3 (s, 9H), 2.4 (d, J=3.3, 2H), 2.7 (m, 2H), 3.2 (m, 2H), 4.2 (d, J=2.2, 1H), 5.1 (s, 2H), 6.3–7.4 (m, 10H), 7.6 (s, 1H), 7.8 (s, 1H), 9.0 (br s, 2×OH).

Step B. Preparation of N-(Nα-Caffeoyl-Nτ-benzyl-L-histidinyl)dopamine

The product obtained in step A of this example (1.41 g, 2.94 mmol) was deprotected according to the indications of general procedure C. The resulting intermediate was coupled with caffeic acid (793 mg, 4.4 mmol) following the indications of general procedure D. The crude material was purified by flash chromatography using 100% EtOAc followed by 5% then 10% MeOH/EtOAc as the eluent. The final product was obtained as white crystals (159 mg, 10%).

$^1$H NMR (DMSO-d$_6$): 2.4 (s, 2H), 2.7–2.9 (m, 2H), 3.2 (m, 2H), 4.5 (d, J=2.8, 1H), 5.0 (s, 2H), 6.3–7.8 (m, 15H), 8.0 (d, J=2.7, 1H), 8.1 (d, J=4.0, 1H), 9.0 (br s, 4×OH).

Example 41

Preparation of N-(Nα-(4-Nitrocinnamoyl)-Nτ-trityl-L-histidinyl)dopamine (Compound No. 41)

The title compound was prepared from N-[Nα-(9-fluorenylmethoxycarbonyl)-Nτ-trityl-L-histidinyl] dopamine (450 mg, 0.6 mmol, example 13, step A) as described for example 13 (step B) using 4-nitrocinnamic acid (1'm 5Uacid (173 mg, ) instead of caffeic acid. The crude material was purified by flash chromatography using 50% EtOAc/CH$_2$Cl$_2$/1% AcOH, 100% EtOAc and 5% MeOH/EtOAc/1% AcOH as the eluent. The title compound was obtained as a yellow powder (105 mg, 25%).

LC-MS: 708 (M$^+$+H); >95% pure.

Example 42

Preparation of N-(Nα-Caffeoyl-O-tert-butyl-L-seryl) dopamine (Compound No. 42)

Step A. Preparation of N-[Nα-(9-Fluorenylmethoxycarbonyl)-O-tert-butyl-L-seryl]dopamine The title compound was prepared from commercially available Nα-(9-fluorenylmethoxycarbonyl)-O-tert-butyl-L-serine (3.0 g, 7.8 mmol) following the indications of general procedure F using dopamine hydrochloride (2.3 g, 12 mmol). The crude material was purified by flash chromatography using successively 15% then 40% EtOAc/CH$_2$Cl$_2$ to give 3.5 g (88%) of the desired product as white crystals.

$^1$H NMR (DMSO-d$_6$): 1.2 (s, 9H), 2.5 (d, J=7.0, 2H), 3.1–3.3 (m, 2H), 3.4–3.5 (m, 2H), 4.0 (m, 1H), 4.2–4.4 (m, 3H), 6.4–8.0 (m, 13H), 8.6 and 8.7 (2×s, 2×OH).

Step B. Preparation of N-(Nα-Caffeoyl-O-tert-butyl-L-seryl)dopamine

The product obtained in step A of this example (841 mg, 1.6 mmol) was deprotected according to the indications of general procedure G. The resulting intermediate was coupled with caffeic acid (440 mg, 2.4 mmol) following the indications of general procedure D. The crude material was purified by flash chromatography using successively 15%, 20% and 60% EtOAc/CH$_2$Cl$_2$/1% AcOH as the eluent. The final product was obtained as white crystals (350 mg, 47%).

$^1$H NMR (DMSO-d$_6$): 1.2 (s, 9H), 2.5 (s, 2H), 3.2 (m, 2H), 3.4 (s, 2H), 4.4 (d, J=5.0, 1H), 6.4–7.3 (M, 8H), 7.8 (m, 2H), 9.0 (br s, 4×OH).

Example 43

Preparation of N-[Nα-(3,4,5-Trihydroxybenzoyl)-O-tert-butyl-L-seryl]dopamine (Compound No. 43)

The title compound was prepared from N-[Nα-(9-fluorenylmethoxycarbonyl)-O-tert-butyl-L-seryl]dopamine (1.16 g, 2.24 mmol, example 42, step A) as described for example 42 (step B) using gallic acid (571 mg, 3.36 mmol) instead of caffeic acid. The crude material was purified by flash chromatography using successively 30%, 40% and 70% EtOAc/CH$_2$Cl$_2$/1% AcOH as the eluent. The title compound was obtained as a white powder (300 mg, 30%).

$^1$H NMR (DMSO-d$_6$): 1.1 (s, 9H), 2.5 (t, J=7.6, 2H), 3.2 (m, 2H), 3.5 (s, 2H), 4.4 (q, J=6.9, 1H), 6.4–7.1 (M, 5H), 7.6 (d, J=8.3, 1H), 7.9 (s, 1H), 8.8 (br s, 5×OH).

Example 44

Preparation of N-[Nα-(2,5-Dimethoxycinnamoyl)-O-tert-butyl-L-seryl]dopamine (Compound No. 44)

The title compound was prepared from N-[Nα-(9-fluorenylmethoxycarbonyl)-O-tert-butyl-L-seryl]dopamine (572 mg, 1.1 mmol, example 42, step A) as described for example 42 (step B) using 2,5-dimethoxycinnamic acid (345 mg, 1.7 mmol) instead of caffeic acid. The crude material was purified by flash chromatography using 10% EtOAc/CH$_2$Cl$_2$/1% AcOH and 50% EtOAc/CH$_2$Cl$_2$ as the eluent. The title compound was obtained as a yellow powder (300 mg, 56%).

$^1$H NMR (DMSO-d$_6$): 1.1 (s, 9H), 2.5 (s, 2H), 3.2 (m, 2H), 3.4 (s, 2H), 3.7 (s, 3H), 3.8 (s, 3H), 4.4 (d, J=4.7, 1H), 6.4–7.2 (M, 8H), 6.9 and 7.6 (2d, J=16.0, 2H), 8.6 and 8.7 (2×s, 2×OH).

Example 45

Preparation of N-[Nα-(3,4,5-Trihydroxybenzoyl)-L-seryl]dopamine (Compound No. 45)

The product of example 43, N-[Nα-(3,4,5-trihydroxybenzoyl)-O-tert-butyl-L-seryl]dopamine (100 mg, 0.22 mmol), was deprotected using the indications of general procedure C. The resulting crude material was purified by flash chromatography to yield 70 mg (80%) of the desired product as a white solid.

¹H NMR (DMSO-d₆): 2.5 (s, 2H), 3.2 (s, 2H), 3.6 (s, 2H), 4.3 (d, J=4.7, 1H), 6.4–7.1 (M, 5H), 7.7 (d, J=6.6, 1H), 7.9 (s, 1H), 9.6 (br s, 6×OH).

Example 46

Preparation of N-[Nα-(2,5-Dimethoxycinnamoyl)-L-seryl]dopamine (Compound No. 46)

The product of example 44, N-[Nα-(2,5-dimethoxycinnamoyl)-O-tert-butyl-L-seryl]dopamine (196 mg, 0.4 mmol), was deprotected using the indications of general procedure C. The resulting crude material was purified by flash chromatography to yield 120 mg, 69% of the desired product as a yellow solid.

¹H NMR (DMSO-d₆): 2.5 (t, 7.8, 2H), 3.2 (q, J=6.9, 2H), 3.6 (d, J=5.0, 2H), 3.7 (s, 3H), 3.8 (s, 3H), 4.3 (q, J=6.7, 1H), 5.0 (br s, 1H), 6.4–7.1 (M, 6H), 6.8 and 7.6 (2d, J=16.0, 2H), 7.9 (t, J=5.0, 1H), 8.2 (d, J=7.9, 1H), 9.5 (br s, 2×OH).

Example 47

Preparation of N-[Nα-(3,4-Dihydroxybenzoyl)-O-tert-butyl-L-seryl]dopamine (Compound No. 47)

The title compound was prepared from N-[Nα-(9-fluorenylmethoxycarbonyl)-O-tert-butyl-L-seryl]dopamine (672 mg, 1.3 mmol, example 42, step A) as described for example 42 (step B) using 2,4-dihydroxybenzoic acid (300 mg, 1.95 mmol) instead of caffeic acid. The crude material was purified by flash chromatography using successively 30% then 60% EtOAc/CH₂Cl₂/1% AcOH as the eluent. The title compound was obtained as a yellow powder (268 mg, 48%).

¹H NMR (DMSO-d₆): 1.1 (s, 9H), 2.5 (t, J=7.7, 2H), 3.2 (m, 2H), 3.5 (d, J=5.7, 2H), 4.4 (d, J=5.7, 2H), 4.4 (d, J=6.8, 1H), 6.4–7.3 (M, 6H), 7.8 (d, J=8.3, 1H), 7.9 (t, J=5.3, 1H), 8.5–9.5 (br s, 4×OH).

Example 48

Preparation of N-(Nα-Caffeoyl-Nδ-methyltrityl-L-glutaminyl)dopamine (Compound No. 48)

Step A. Preparation of N-[Nα-(9-Fluorenylmethoxycarbonyl)-Nδ-methyltrityl-L-glutaminyl]dopamine Commercially available Nα-(9-fluorenylmethoxycarbonyl)-Nδ-methyltrityl-L-glutamine (6.0 g, 10 9.6 mmol) was coupled with dopamine hydrochloride (2.7 g, 14.4 mmol) as described in general procedure F. The crude material was purified by flash chromatography eluting successively with 15%, 30% and 50% EtOAc/CH₂Cl₂. The product was obtained as yellow powder (5.8 g, 80%).

¹H NMR (DMSO-d₆): 1.6–1.9 (m, 2H), 2.2 (s, 3H), 2.3 (s, 2H), 2.5 (s, 2H), 3.2 (m, 2H), 3.9 (m, 1H), 4.3 (m, 3H), 6.4–7.8 (m, 25H), 7.9 (d, J=7.4, 2H), 8.4 (s, 1H), 8.6–8.7 (br s, 2×OH).

Step B. Preparation of N-(Nα-Caffeoyl-Nδ-methyltrityl-L-glutaminyl)dopamine

The product obtained in step A of this example (543 mg, 0.7 mmol) was deprotected according to the indications of general procedure G. The product thus obtained was then coupled with caffeic acid (200 mg, 1.0 mmol) according to the indications of general procedure D. The reaction mixture was heated at 60° C. for 4 h. The crude product was purified by flash chromatography using successively 30%, 50% and 80% EtOAc/CH₂Cl₂/1% AcOH to give the desired product (120 mg, 24%) as yellow crystals.

¹H NMR (DMSO-d₆): 1.6–1.8 (m, 2H), 2.2 (s, 3H), 2.3 (t, J=8.4, 2H), 2.5 (s, 2H), 3.1 (d, J=6.0, 2H), 4.3 (m, 1H), 6.4–7.3 (m, 22H), 7.9 (s, 1H), 8.0 (d, J=8.4, 1H), 8.5 (s, 1H), 8.7–9.5 (br s, 2×OH).

Example 49

Preparation of N-[Nα-(3,4-Dihydroxybenzoyl)-Nδ-methyltrityl-L-glutaminyl]dopamine (Compound No. 49)

This compound was prepared from N-[Nα-(9-fluorenylmethoxycarbonyl)-Nδ-methyltrityl-L-glutaminyl]dopamine (705 mg, 0.9 mmol, example 48, step A) as described for example 48 (step B) using 3,4-dihydroxybenzoic acid (215 mg, 1.4 mmol) instead of caffeic acid. The crude material was purified by flash chromatography using successively 40%, 50% and 60% EtOAc/CH₂Cl₂/1% AcOH as the eluent. The title compound was obtained as a white powder (100 mg, 16%).

¹H NMR (DMSO-d₆): 1.7–1.9 (m, 2H), 2.2 (s, 3H), 2.3 (s, 2H), 2.5 (s, 2H), 3.2 (d, J=5.6, 2H), 4.3 (s, 1H), 6.4–7.4 (M, 20H), 7.8 (s, 1H), 8.0 (d, J=7.5, 1H), 8.5 (s, 1H), 9.0 (br s, 4×OH).

Example 50

Preparation of N-[Nα-(3-Nitrocinnamoyl)-Nδ-methyltrityl-L-glutaminyl]dopamine (Compound No. 50)

This compound was prepared from N-[Nα-(9-fluorenylmethoxycarbonyl)-Nδ-methyltrityl-L-glutaminyl]dopamine (628 mg, 0.8 mmol, example 48, step A) as described for example 48 (step B) using 3-nitrocinnamic acid (240 mg, 1.2 mmol) instead of caffeic acid. The crude material was purified by flash chromatography using successively 15%, 20% and 35% EtOAc/CH₂Cl₂/1% AcOH as the eluent. The title compound was obtained as a yellow powder (247 mg, 42%).

¹H NMR (DMSO-d₆): 1.8 (m, 2H), 2.2 (s, 3H), 2.3 (t, J=7.6, 2H), 2.5 (t, J=6.7, 2H), 3.2 (d, J=6.6, 2H), 4.3 (q, J=5.8, 1H), 6.4–8.3 (m, 23H), 7.7 (t, J=7.6, 1H), 8.0 (s, 1H), 8.6 and 8.7 (2×s, 2×OH).

Example 51

Preparation of N-(Nα-Caffeoyl-Nδ-butoxycarbonyl-L-ornithyl)dopamine (Compound No. 51)

Step A. Preparation of N-[Nα-(9-Fluorenylmethoxycarbonyl)-N-butoxycarbonyl-L-ornithyl]dopamine The title compound was prepared from Nα-(9-fluorenylmethoxycarbonyl)-Nδ-tert-butoxycarbonyl-L-ornithine (4.0 g, 8.8 mmol) following the indications of general procedure F using dopamine hydrochloride (2.5 g, 13.0 mmol). The final product was obtained as white crystals (4.0 g, 77%) after purification by flash chromatography using initially 20% and then 45% EtOAc/CH₂Cl₂ containing 1% AcOH as the eluent.

¹H NMR (DMSO-d₆): 1.4–1.6 (m, 13H), 2.5 (t, J=6.5, 2H), 3.0 (d, J=5.0, 2H), 3.2 (m, 2H), 3.9 (s, 1H), 4.2 (d, J=6.0, 1H), 4.3 (d, J=6.4, 2H), 6.4–7.7 (M, 11H), 7.8 (s, 1H), 7.9 (t, J=7.5, 2H), 8.6–8.7 (2×s, 2×OH).

Step B. Preparation of N-(Nα-Caffeoyl-Nδ-butoxycarbonyl-L-ornithyl)dopamine

N-[Nα-(9-fluorenylmethoxycarbonyl)-Nδ-butoxycarbonyl-L-ornithyl]dopamine (1.0 g, 1.75 mmol)

was deprotected following the indications of general procedure G. The free amino groups thus obtained were coupled with caffeic acid (472 mg, 2.6 mmol) following the general procedure D. The crude material was purified by flash chromatography using a solvent gradient from 30% to 90% EtOAc/CH$_2$Cl$_2$/1% AcOH. The desired product was obtained as white crystals (370 mg, 40%).

$^1$H NMR (DMSO-d$_6$): 1.4–1.6 (m, 13H), 2.5 (t, J=6.9, 2H), 3.1–3.3 (m, 4H), 3.9 (t, J=4.8, 1H), 6.3 and 7.2 (2d, J=16.0, 2H), 6.4–6.9 (M, 7H), 7.8 (s, 1H), 7.9 (t, J=5.0, 1H), 9.5 (br s, 4×OH).

Example 52

Preparation of N-[Nα-(4-Hydroxybenzoyl)-Nτ-trityl-L-histidinyl]dopamine (Compound No. 52)

The title compound was prepared from N-[Nα-(9-fluorenylmethoxycarbonyl)-Nτ-trityl-L-histidinyl]dopamine (500 mg, 0.7 mmol, example 13, step A) as described for example 13 (step B) using 4-hydroxybenzoic acid (137 mg, 1.0 mmol) instead of caffeic acid. The crude material was purified by flash chromatography using a solvent gradient from 50% to 99% EtOAc/CH$_2$Cl$_2$/1% AcOH and 5% MeOH/EtOAc/1% AcOH. The title compound was obtained as a white powder (130 mg, 30%).

LC-MS: 653 (M$^+$+H); >95% pure.

Example 53

Preparation of N-[Nα-(3,4-Dihydroxybenzoyl)-L-seryl]dopamine (Compound No. 53)

The title compound was prepared by hydrolysis of the tert-butyl protective group of N-[Nα-(3,4-dihydroxybenzoyl)-O-tert-butyl-L-seryl]dopamine prepared in example 47 (121 mg, 0.3 mmol) using the indications of general procedure C. Purification by flash chromatography using a solvent gradient from 50% to 80% EtOAc/CH$_2$Cl$_2$/1% AcOH and 5% MeOH/CH$_2$Cl$_2$/1% AcOH, yielded the desired product as a white solid (75 mg, 75%).

$^1$H NMR (DMSO-d$_6$): 2.52 (m, 2H); 3.19 (m, 2H); 3.69 (d, J=6.1, 2H); 4.49 (s, 2H); 4.64 (q, J=5.6, J=6.4, 1H); 6.42 (d, J=7.6, 1H); 6.57 (s, 1H); 6.60 (d, J=8.2, 1H); 6.77 (d, J=8.3, 1H); 7.23 (d, J=7.2, 1H); 7.25 (s, 1H); 7.29–7.37 (m, 5H); 8.01 (d, J=7.9, 1H); 8.02 (t, J=5.4, 1H); 8.62 (br s, 1H); 8.72 (br s, 1H); 9.12 (br s, 1H); 9.47 (br s, 1H).

Example 54

Preparation of N-[Nα-(3,4,5-Trihydrozybenzoyl)-Nδ-butoxycarbonyl-L-ornithyl]dopamine (Compound No. 54)

N-[Nα-(9-fluorenylmethoxycarbonyl)-Nδ-butoxycarbonyl-L-ornithyl]dopamine (1.2 g, 2.0 mmol, example 51, step A) was deprotected following the indications of general procedure G. The free amino groups thus obtained were coupled with 3,4,5-trihydroxybenzoic acid (527 mg, 3.1 mmol) following the general procedure D. The crude material was purified by flash chromatography using a solvent gradient from 40% to 80% EtOAc/CH$_2$Cl$_2$/1% AcOH and 5% MeOH/EtOAc/1% AcOH. The desired product was obtained as white crystals (426 mg, 40%).

$^1$H NMR (DMSO-d$_6$): 1.4–1.6 (m, 13H), 2.5 (d, J=6.4, 2H), 3.0–3.3 (m, 4H), 3.6 (d, J=5.0, 1H), 6.4–7.0 (m, 6H), 7.6 (s, 1H), 7.9 (t, J=6.0, 1H), 10.0 (br s, 5×OH).

Specific Examples for the Preparation of Derivatives of General Formula III'

Example 55

Preparation of Nα,Nε-di-(3,5-Dihydroxynaphthyl-2-carbonyl)-L-L-lye Benzyl Ester (Compound No. 55)

Step A. Preparation of Nα,Nε-di-(tert-butoxycarbonyl)-L-lysine Benzyl Ester

Commercially available Nα,Nε-di-(tert-butoxycarbonyl)-L-lysine dicyclohexylamine salt (2.0 g, 3.8 mmol) was reacted with benzyl bromide following the indications of general procedure B (b). The crude material was purified by flash chromatography with 100% hexane and 30% EtOAc/hexane to yield 2.0 g (79%) of the desired material.

LC-MS: 437 (M$^+$+H); >96% pure.

Step B. Preparation of Nα,Nε-di-(3,5-Dihydroxynaphthyl-2-carbonyl)-L-lysine Benzyl Ester The title compound was prepared from Nα,Nε-di-(tert-butoxycarbonyl)-L-lysine benzyl ester (1.56 g, 3.6 mmol, step A above) using the indications of general procedure C for the deprotection of the Boc groups. The compound thus obtained was coupled with 3,5-dihydroxy-2-naphthoic acid (2.2 g, 11.0 mmol) following the indications of general procedure D. The reaction mixture was stirred for 8 h at 60° C. The product was purified by flash chromatography using successively 5%, 10% and 15% EtOAc/CH$_2$Cl$_2$ to give 1.24 g (57%) of the desired material.

LC-MS: 609 (M$^+$+H); >85% pure.

Example 56

Preparation of Nα,Nε-di-(3,5-Dihydroxynaphthyl-2-carbonyl)-L-lysine hydroxylamide (Compound No. 56)

Step A. Preparation of Nα,Nε-di-(3,5-Dihydroxynaphthyl-2-carbonyl)-L-lysine (Compound No. 65)

The product obtained in example 55, Nα,Nε-di-(3,5-dihydroxynaphthyl-2-carbonyl)-L-lysine benzyl ester (1.13 g, 1.86 mmol), was hydrogenolysed following the conditions described in general procedure E. The crude material was obtained by filtration and evaporation of the reaction mixture to give 959 mg, 99% of the acid. This product was used without further purification in the next step.

$^1$H NMR (DMSO-d$_6$): 1.4–1.7 (m, 4H), 1.9 (m, 2H), 3.4 (d, J=2.6, 2H), 4.5 (d, J=2.6, 1H), 6.7–8.6 (m, 10H), 9.0 (s, 1H), 9.2 (d, J=3.5, 1H), 9.8–12.0 (4×s, 4×OH), 12.6 (br s, 10H).

Step B. Preparation of Nα,Nε-di-(3,5-Dihydroxynaphthyl-2-carbonyl)-L-lysine Hydroxylamide The compound obtained in step A of this example (373 mg, 0.72 mmol) was treated with O-benzylhydroxylamine hydrochloride (230 mg, 1.4 mmol) following the conditions described in general procedure F. The intermediate, Nα,Nε-di-(3,5-dihydroxynaphthyl-2-carbonyl)-L-lysine O-benzylhydroxylamide was deprotected by catalytic hydrogenation as described in general procedure E to yield 10% (40 mg) of the amide.

$^1$H NMR (DMSO-d$_6$): 1.2 (s, 2H), 1.3–1.5 (m, 2H), 1.6 (s, 2H), 1.8 (s, 2H), 4.5 (d, J=5.0, 1H), 6.8–8.5 (m, 10H, 8.9–9.1 (m, 3H), 10.0 (br s, 2×OH), 10.3 (s, OH), 11.6 and 12.0 (2×br s, 2×OH).

Example 57

Preparation of N-[Nα-(3,5-Dihydroxynaphthyl-2-carbonyl)-L-tyrosyl]dopamine (Compound No. 57)

The title compound was prepared from the product obtained in example 4, step A (1.16 g, 2.8 mmol) according to the indications of general procedures C and D. In general procedure D, 3,5-dihydroxy-2-naphthaoic acid (858 mg, 4.2 mmol) was used for the coupling reaction. The crude material was purified by flash chromatography using initially 20% then 30% EtOAc/CH$_2$Cl$_2$ as the eluent. The final product was obtained as yellow crystals (560 mg, 40%).

$^1$H NMR (DMSO-d$_6$): 2.5 (t, J=3.8, 2H), 2.8–3.3 (m, 2H), 3.4 (s, 2H), 4.7 (q, J=4.0, 1H), 6.4–7.5 and 8.4 (m, 12H), 8.2 (t, J=2.6, 1H), 9.0 (d, J=3.0, 1H), 8.6–11.5 (5×s, 5×OH).

Example 58

Preparation of N-[Nα-(4,8-Dihydroxyquinoline-2-carbonyl)-L-tyrosyl]dopamine (Compound No. 58)

The synthesis of this product was performed as described above for the synthesis of N-[Nα-(3,5-dihydroxynaphthyl-2-carbonyl)-L-tyrosyl]dopamine (example 57). In this case, 4,8-dihydroxyquinoline-2-carboxylic acid (673 mg, 3.3 mmol) was used instead of 3,5-dihydroxy-2-naphthaoic acid. The crude material was purified by flash chromatography eluting with 30% EtOAc/CHCl$_3$ and 5, 10% MeOH/CHCl$_3$ to yield 661 mg, 60% of the desired material.

$^1$H NMR (DMSO-d$_6$): 2.5 (t, J=3.5, 2H), 3.0 (m, 2H), 3.2 (q, J=3.4, 2H), 4.6 (s, 1H), 6.4–7.4 (m, 11H), 7.6 (d, J=4.2, 1H), 8.2 (s, 1H), 8.5–10.2 (5×br s, 5×OH).

Example 59

Preparation of N-[Nα-(3,5-Dihydroxynaphthyl-2-carbonyl)-L-tryptophanyl]dopamine (Compound No. 59)

Step A. Preparation of N-[Nα-(tert-Butoxycarbonyl)-L-tryptophanyl]dopamine

The title compound was prepared from N-(tert-butoxycarbonyl)-L-tryptophan (204 mg, 0.65 mmol) by coupling it with dopamine hydrochloride according to general procedure F. Purification by flash chromatography eluting with 2.5% MeOH/EtOAc provided the title compound as a syrup (215 mg, 75%).

$^1$H NMR (DMSO-d$_6$): 1.31 (s, 9H), 2.46 (t, J=7.4, 2H), 3.02 (m, 2H), 3.14 (m, 1H), 3.22 (s, 1H), 4.15 (m, 1H), 6.43 (d, J=7.6, 1H), 6.58 (s, 1H), 6.62 (d, J=7.5, 1H), 6.66 (d, J=8.1, 1H), 6.97 (t, J=7.5, 1H), 7.05 (t, J=7.3, 1H), 7.10 (s, 1H), 7.31 (d, J=7.7, 1H), 7.58 (d, J=7.7, 1H), 7.86 (t, J=4.7, 1H), 8.62 (s, 1H), 8.71 (s, 1H), 10.77 (s, 1H).

Step B. Preparation of N-[Nα-(3,5-Dihydroxynaphthyl-2-carbonyl)-L-tryptophanyl]dopamine The title compound was prepared from the product obtained in step A of this example (841 mg, 1.9 mmol) by removing the Boc group following the indications of general procedure C. The resulting unblocked derivative was then coupled with 3,5-dihydroxy-2-naphthaoic acid (587 mg, 2.9 mmol) according to the indications of general example D. Purification by flash chromatography using initially 20% then 30% EtOAc/CH$_2$Cl$_2$ afforded product (350 mg, 35%) as a yellow powder.

$^1$H NMR (DMSO-d$_6$): 2.5 (s, 2H), 3.1 (m, 2H), 3.4 (s, 2H), 4.8 (d, J=2.0,1 H), 6.3–7.5 (m, 13H), 8.2 (s, 1H), 9.2 (d, J=3.4, 1H), 8.7–11.5 (4×s, 4×OH), 10.8 (s, 1H).

Example 60

Preparation of N-[Nα-(3,5-Dihydroxynaphthyl-2-carbonyl)-L-3,4-dihydroxyphenylalanyl]dopamine (Compound No. 60)

The title compound was prepared by cleaving the Boc protective group (general procedure C) of the product prepared in step A of example 15 (687 mg, 1.6 mmol) and coupling it with 3,5-dihydroxy-2-naphthaoic acid (485 mg, 2.4 mmol) as described in general procedure D. Purification by flash chromatography using 30% EtOAc/CH$_2$Cl$_2$/1% AcOH and 10% MeOH/CH$_2$Cl$_2$/1% AcOH, yielded the desired product as a yellow solid (412 mg, 50%).

$^1$H NMR (DMSO-d$_6$): 2.5 (s, 2H), 2.7–3.0 (m, 2H), 3.2 (m, 2H), 4.6 (s, 1H), 6.3–8.2 (m, 11H), 8.4 (s, 1H), 9.0 (d, J=3.0, 1H), 9.8 (br s, 6H).

Example 61

Preparation of N-[Nα-(3,5-Dihydroxynaphthyl-2-carbonyl)-L-asparagyl]dopamine (Compound No. 61)

Step A. Preparation of Nα-(tert-Butoxycarbonyl)-L-asparagine Benzyl Ester

Commercially available Nα-(tert-butoxycarbonyl)-L-asparagine (2.5 g, 11.0 mmol) was benzylated according to general procedure B (b). The reaction was stirred at room temperature for 4 h. The crude material was purified by flash chromatography using 100% hexane and, successively 10% and 30% EtOAc/hexane to yield the desired benzyl ester 1.86 g, 54%.

$^1$H NMR (DMSO-d$_6$): 1.3 (s, 9H), 2.5–3.0 (ABX, J=5.0, 17.6, 2H), 4.4 (q, J=5.7, 1H), 4.5 (q, J=10.7, 2H), 7.2–7.3 (m, 7H), 7.6 (d, J=8.0, 1H).

Step B. Preparation of Nα-(3,5-Dihydroxynaphthyl-2-carbonyl)-L-asparagine Benzyl Ester The title compound was prepared by cleaving the Boc protective group (general procedure C) of the product prepared in step A of this example (1.0 g, 3.3 mmol) and coupling it with 3,5-dihydroxy-2-naphthaoic acid (1.0 mg, 5.0 mmol) as described in general procedure D. The crude material (806 mg, 2.5 mmol) was used without purification in step C.

Step C. Preparation of N-[Nα-(3,5-Dihydroxynaphthyl-2-carbonyl)-L-asparagyl]dopamine This compound was synthesized from Nα-(3,5-dihydroxynaphthyl-2-carbonyl)-L-asparagine benzyl ester (step B, above) by a two step sequence. The benzyl ester was cleaved using general procedure E and the resulting acid was coupled with dopamine hydrochloride (959 mg, 5.0 mmol) following the indications of general procedure F. The crude material was purified by flash chromatography using initially 50% then 90% EtOAc/CH$_2$Cl$_2$/1% AcOH and 10% MeOH/EtOAc/1% AcOH, to yield 150 mg, 17% of the title compound.

$^1$H NMR (DMSO-d$_6$): 2.4–2.8 (m, 4H), 3.2 (s, 2H), 4.8 (s, 1H), 6.4–7.5 (m, 10H), 8.0–8.4 (2s, 2H), 8.6–11.5 (br s, 4×OH).

Example 62

Preparation of N-[Nα-(4,8-Dihydroxyquinoline-2-carbonyl)-Oγ-ted-butyl-L-aspartyl]dopamine (Compound No. 62)

Step A. Preparation of N-[Nα-(Benzyloxycarbonyl)-Oγ-tert-butyl-L-aspartyl]dopamine Commercially available Nα-(benzyloxycarbonyl)-Oγ-tert-butyl-L-aspartic acid (2.5 g, 7.7 mmol) was coupled to dopamine hydrochloride (2.3 g, 12.0 mmol) following the indications of general example F. Purification by flash chromatography using initially 20% then 30% EtOAc/CH$_2$Cl$_2$ gave 3.2 g (91%) of the desired compound.

$^1$H NMR (DMSO-d$_6$): 1.3 (s, 9H), 2.3–2.7 (m, 4H), 3.2 (s, 2H), 4.3 (d, J=2.6, 1H), 4.9–5.2 (2d, J=6.3, 6.3, 2H), 6.3–7.4 (m, 8H), 7.5 (d, J=4.0, 1H), 7.9 (s, 1H), 8.6 and 8.7 (2×s, 2×OH).

Step B. Preparation of N-[Nα-(4,8-Dihydroxyquinoline-2-carbonyl)-Oγ-tert-butyl-L-aspartyl]dopamine The product obtained in step A of this example (1.0 g, 2.5 mmol) was hydrogenolysed according to the indications of general procedure E. The product thus obtained was then coupled with 4,8-dihydroxyquinoline-2-carboxylic acid (754 mg, 3.7 mmol) according to the indications of general procedure D. The reaction mixture was heated at 60° C. for 4 h. The crude product was purified by flash chromatography using a solvent gradient from 20% to 50% EtOAc/CH₂Cl₂/ 1% AcOH to give the desired product (500 mg, 45%) as a yellow powder.

¹H NMR (DMSO-d₆): 1.3 (s, 9H), 2.5 (t, J=5.4, 2H), 2.6–2.9 (dd, J=4.4, 5.0, 2H), 3.2 (m, 2H), 4.9 (d, J=3.3, 1H), 6.3–7.7 (m, 7H), 8.7 (br s, 3H), 9.7 (d, J=4.0, 1H), 10.0 (s, 1H), 11.7 (br s, 1H).

Example 63

Preparation of N-[Nα-(4,8-Dihydroxyquinoline-2-carbonyl)-L-aspartyl]dopamine (Compound No. 63)

The title compound was prepared by hydrolysis of the tert-butyl protective group of N-[Nα-(4,8-dihydroxyquinoline-2-carbonyl)-Oγ-tert-butyl-L-aspartyl] dopamine prepared in example 62, step B (121 mg, 2.4 mmol) using the indications of general procedure C in the presence of triisopropylsilane (187 mg, 1.2 mmol). Purification by flash chromatography using 50% EtOAc/CH₂Cl₂/ 1% AcOH yielded the desired product as a yellow powder (61 mg, 57%).

¹H NMR (DMSO-d₆): 2.5 (t, J=3.5, 2H), 2.7–2.9 (2q, J=2.5, 3.9, 2H), 3.2 (m, 2H), 4.9 (d, J=3.3, 1H), 6.4–7.7 (m, 7H), 8.0 (s, 1H), 9.6 (d, J=3.9, 1H), 10.0–12.0 (br s, 5×OH).

Example 64

Preparation of N-[Nα-(4,8-Dihydroxyquinoline-2-carbonyl)-Nγ-trityl-L-asparagyl]dopamine (Compound No. 64)

The title compound was prepared from N-[Nα-(9-fluorenylmethoxycarbonyl)-Nγ-trityl-L-asparagyl] dopamine (1.34 g, 1.8 mmol, example 7, step A) as described for example 7 (step B) using 4,8-dihydroxyquinoline-2-carboxylic acid (564 mg, 2.75 mmol) instead of caffeic acid. The crude material was purified by flash chromatography using a solvent gradient from 30% to 60% EtOAc/CH₂Cl₂ containing 1% AcOH. The title compound was obtained as yellow crystals (663 mg, 52%).

¹H NMR (DMSO-d₆): 2.5 (m, 2H), 2.6–2.9 (m, 2H), 3.2 (m, 2H), 4.8 (m, 1H), 6.4–7.4 (m, 22H), 7.6 (d, J=7.9, 1H), 8.1 (s, 1H), 8.5 (s, 1H), 8.7, 9.8, 9.9 and 11.9 (4×br s, 4×OH).

Example 65

Preparation of Nα,Nε-di-(3,5-Dihydroxynaphthyl-2-carbonyl)-L-lysine (Compound No. 65)

The preparation of this compound was already described in example 56, step A (vide infra).

Example 66

Preparation of N-[Nα,Nε-di-(3,5-Dihydroxynaphthyl-2-carbonyl)-L-lysyl]dopamine (Compound No. 66)

Nα,Nε-di-(3,5-dihydroxynaphthyl-2-carbonyl)-L-lysine (451 mg, 0.87 mmol, product of example 65) was coupled with dopamine hydrochloride (330 mg, 1.7 mmol) following the indications of general procedure F. The crude material was purified by flash chromatography using first 30% then 70% EtOAc/CH₂Cl₂. The product was obtained as yellow crystals (171 mg, 30%).

¹H NMR (DMSO-d₆): 1.4 (m, 2H), 1.6 (d, J=4.4, 2H), 1.8 (m, 2H), 2.5 (t, J=7.2, 2H), 3.1–3.3 (m, 2H), 3.3 (d, J=5.9, 2H), 4.6 (q, J=6.0, 1H), 6.4–8.7 (m, 13H), 7.4 and 7.5 (2×s, 2×OH) 8.2 (s, 1H), 9.0 (s, 1H), 9.1 (d, J=7.4, 1H), 9.9, 10.0, 11.5 and 11.9 (4×s, 4×OH).

Example 67

Preparation of N-[Nα-(4,8-Dihydroxyquinoline-2-carbonyl)-L-asparagyl]dopamine (Compound No. 67)

The title compound was prepared by hydrolysis of the trityl protective group of N-[Nα-(4,8-dihydroxyquinoline-2-carbonyl)-Nγ-trityl-L-asparagyl]dopamine prepared in example 64 (220 mg, 0.3 mmol) using the indications of general procedure C. Purification by flash chromatography using 70% EtOAc/CH₂Cl₂/1% AcOH and 10% MeOH/ CH₂Cl₂/1% AcOH, yielded the desired product as a yellow solid (116 mg, 81%).

¹H NMR (DMSO-d₆): 2.5 (s, 2H), 2.6–2.8 (m, 2H), 3.2 (m, 2H), 4.8 (m, 1H), 6.4–7.4 (m, 7H), 7.6 (d, J=6.9, 1H), 8.0 (s, 1H), 9.5 (s, 2H), 10.0 (br s, 4×OH).

Example 68

Preparation of N-[Nα-(4,8-Dihydroxyquinoline-2-carbonyl)-L-tyrosyl]-3,4-dihydroxybenzylamine (Compound No. 68)

Step A. Preparation of N-[Nα-(tert-Butoxycarbonyl)-L-tyrosyl]-3,4-dihydroxybenzylamine Commercially available Nα-(tert-butoxycarbonyl)-L-tyrosine (1.5 g, 5.34 mmol) was coupled with 3,4-dihydroxybenzylamine hydrobromide (1.76 g, 8.0 mmol) as described in general procedure F. The crude material was purified by flash chromatography using initially 30% then 60% EtOAc/CH₂Cl₂ containing 1% AcOH. The product was obtained as white powder (1.9 g, 88%).

¹H NMR (DMSO-d₆): 1.3 (s, 9H), 2.5–2.8 (m, 2H), 4.1 (t, J=4.5, 2H), 6.4–7.0 (m, 7H), 8.2 (s, 1H), 8.7 (br s, 2H), 9.0 (s, 1H).

Step B. Preparation of N-[Nα-(4,8-Dihydroxyquinoline-2-carbonyl)-L-tyrosyl]-3,4-dihydroxybenzylamine The product obtained in step A of this example (400 mg, 1.0 mmol) was deprotected according to the indications of general procedure C. The product thus obtained was then coupled with 4,8-dihydroxyquinoline-2-carboxylic acid (310 mg, 1.5 mmol) according to the indications of general procedure D. The reaction mixture was heated at 60° C. for 4 h. The crude product was purified by flash chromatography using successively 50% then 60% EtOAc/CH₂Cl₂/1% AcOH and 99% EtOAc/1% AcOH to give the desired product (228 mg, 47%) as yellow crystals.

¹H NMR (DMSO-d₆): 2.8–3.1 (m, 2H), 4.1 (s, 2H), 4.7 (s, 2H), 6.4–7.4 (m, 11H), 7.5 (d, J=7.0, 1H), 8.4 (s, OH), 8.7 (br s, 2×OH), 9.2–10.0 (br s, 3×OH).

Example 69

Preparation of N-[Nα-(4,8-Dihydroxyquinoline-2-carbonyl)-Nδ-methyltrityl-L-glutaminyl]-3,4-dihydroxybenzylamine (Compound No. 69)

The title compound was prepared from N-[Nα-(9-fluorenylmethoxycarbonyl)-Nδ-methyltrityl-L-glutaminyl]-3,4-dihydroxybenzylamine (1.0 g, 1.4 mmol, example 26, step A) as described for example 26 using 4,8-dihydroxyquinoline-2-carboxylic acid (435 mg, 2.1 mmol) instead of 4-hydroxy-3-nitrobenzoic acid. The crude material was purified by flash chromatography using a solvent gradient from 30% to 60% EtOAc/CH₂Cl₂/1% AcOH. The title compound was obtained as yellow crystals (100 mg, 10%).

¹H NMR (DMSO-d₆): 1.8–2.1 (m, 2H), 2.2 (s, 3H), 2.4 (m, 2H), 4.1 (d, J=3.9, 2H), 4.5 (s, 1H), 6.5–7.6 (m, 21H), 8.2 (s, 1H), 8.5 (s, 1H), 8.5 and 8.7 (2×br s, 2×OH), 9.5 (d, J=5.3, 1H), 10.0 and 11.8 (2×br s, 2×OH).

Example 70

Preparation of N-[Nα-(4,8-Dihydroxyquinoline-2-carbonyl)-Nτ-trityl-L-histidinyl]-3,4-dihydroxybenzylamine (Compound No. 70)

N-[Nα-(9-fluorenylmethoxycarbonyl)-Nτ-trityl-L-histidinyl]-3,4-dihydroxybenzylamine (689 mg, 0.93 mmol, example 22) was deprotected according to the indications of general procedure G. The crude intermediate was coupled with 4,8-dihydroxyquinoline-2-carboxylic acid (286 mg, 1.4 mmol) according to procedure D. The crude product was purified by flash chromatography using a solvent gradient from 30% to 100% EtOAc/CH₂Cl₂ containing 1% AcOH and 5% MeOH/EtOAc/CH₂Cl₂ to give 374 mg (57%) of a yellow powder.

¹H NMR (DMSO-d₆): 2.9–3.2 (m, 2H), 4.1 (s, 2H), 4.8 (m, 1H), 6.5–7.5 (m, 25H), 8.4 (s, 1H), 8.7–11.7 (br s, 4×OH).

Example 71

Preparation of N-[Nα-(4,8-Dihydroxyquinoline-2-carbonyl)-Nτ-methyltrityl-L-histidinyl]dopamine (Compound No. 71)

The title compound was prepared from N-[Nα-(9-fluorenylmethoxycarbonyl)-Nτ-methyltrityl-L-histidinyl] dopamine (265 mg, 0.34 mmol, example 28, step A) as described for example 28 (step B) using 4,8-dihydroxyquinoline-2-carboxylic acid (106 mg, 0.52 mmol) instead of dihydrocaffeic acid. The crude material was purified by flash chromatography using a solvent gradient from 40% to 90% EtOAc/CH₂Cl₂/1% AcOH and 5% MeOH/EtOAc/1% AcOH. The title compound was obtained as a yellow powder (25 mg, 10%).

LC-MS: 734 (M⁺+H); >90% pure.

Example 72

Preparation of N-[Nα-(4,8-Dihydroxyquinoline-2-carbonyl)-O-tert-butyl-L-seryl]dopamine (Compound No. 72)

The title compound was prepared from N-[Nα-(9-fluorenylmethoxycarbonyl)-O-tert-butyl-L-seryl]dopamine (676 mg, 1.3 mmol, example 42, step A) as described for example 42 (step B) using 4,8-dihydroxyquinoline-2-carboxylic acid (402 mg, 1.96 mmol) instead of caffeic acid. The crude material was purified by flash chromatography using successively 30%, 40% and 70% EtOAc/CH₂Cl₂/1% AcOH as the eluent. The title compound was obtained as a yellow powder (130 mg, 21%).

¹H NMR (DMSO-d₆): 1.2 (s, 9H), 2.5 (t, J=7.2, 2H), 3.1–3.2 (m, 2H), 3.5–3.7 (ABX, J=7.8, 15.0, 2H), 4.6 (d, J=7.2, 1H), 6.4–7.6 (M, 7H), 8.0 (s, 1H), 8.8 (br s, 2×OH), 9.4 (d, J=5.0, 1H), 10.0 and 11.5 (2×br s, 2×OH).

Specific Examples for the Preparation of Derivatives of General Formula IV'

Example 73

Preparation of N₁-[Nα-(4,8-Dihydroxyquinoline-2-carbonyl)-L-tyrosyl]-N₂-(2-hydroxybenzoyl)-hydrazine (Compound No. 73)

Step A. Preparation of N₁-[Nα-(tert-Butoxycarbonyl)-L-tyrosyl]-N₂-(2-hydroxybenzoyl)-hydrazine The title compound was prepared from Nα-(tert-butoxycarbonyl)-L-tyrosine (2.5 g, 8.9 mmol) by coupling it with salicylic hydrazide (2.7 g, 13.3 mmol) following the indications of general procedure F. The crude material was purified by flash chromatography using successively 10%, 15% and 20% EtOAc/CH₂Cl₂ as the eluent to yield 2.2 g (60%) of the desired product as a white powder.

¹H NMR (DMSO-d₆): 1.3 (s, 9H), 2.6–3.0 (2d, J=5.2, 6.4, 2H), 4.2 (br s, 1H), 6.5–7.5 (m, 8H), 7.9 (d, J=3.3, 1H), 9.0 (s, 1H), 10.4 (s, 1H), 10.5–12.0 (2×s, 2×OH).

Step B. Preparation of N₁-[Nα-(4,8-Dihydroxyquinoline-2-carbonyl)-L-tyrosyl]-N₂-(2-hydroxybenzoyl)-hydrazine The product obtained in step A of this example (379 mg, 0.9 mmol) was deprotected according to the indications of general procedure C. The product thus obtained was then coupled with 4,8-dihydroxyquinoline-2-carboxylic acid (281 mg, 1.4 mmol) according to the indications of general procedure D. The reaction mixture was heated at 60° C. for 4 h. The crude product was purified by flash chromatography using successively 60%, 80% and 90% EtOAc/CH₂Cl₂ followed by 5% MeOH/CH₂Cl₂ to give 275 mg (40%) of the final product as yellow crystals.

¹H NMR (DMSO-d₆): 3.2 (2d, J=5.0, 5.7, 2H), 4.9 (s, 1H), 6.5–7.5 (m, 12H), 7.6 (d, J=4.0, 1H), 7.9 (d, J=3.9, 1H), 9.0–12.0 (4×br s, 4×OH), 10.6 (s, 1H).

Example 74

Preparation of N₁-(Nα-Caffeoyl-L-tyrosyl)-N₂-(2-hydroxybenzoyl)-hydrazine (Compound No. 74)

N₁-[Nα-(tert-butoxycarbonyl)-L-tyrosyl]-N₂-(2-hydroxybenzoyl)-hydrazine (349 mg, 0.84 mmol) prepared in example 73, step A was deprotected following the indications of general procedure C and coupled with caffeic acid (230 mg, 1.3 mmol) using general procedure D. The final product was purified by flash chromatography eluting with 40% EtOAc/CH₂Cl₂ then successively 5% and 10% MeOH/CH₂Cl₂ to yield 100 mg, 25% of the title compound.

LC-MS: 478 (M⁺+H); >80% pure.

Example 75

Preparation of N₁-(Nα-Caffeoyl-L-tryptophanyl)-N₂-(2-hydroxybenzoyl)-hydrazine (Compound No. 75)

Step A. Preparation of N₁-[Nα-(tert-Butoxycarbonyl)-L-tryptophanyl]-N₂-(2-hydroxybenzoyl)-hydrazine The title compound was prepared from commercially available Nα-(tert-butoxycarbonyl)-L-tryptophan (2.5 g, 8.2 mmol) by coupling it with salicylic hydrazide (2.5 g, 16.4 mmol) following the indications of general procedure F. The crude material was purified by flash chromatography using successively 5%, 10% and 20% EtOAc/CH₂Cl₂ as the eluent to yield 2.7 g (75%) of the desired product as a white powder.

¹H NMR (DMSO-d₆): 1.3 (s, 9H), 2.9–3.2 (tt, 5.0, 6.8, 2H), 4.4 (s, 1H), 6.9–8.0 (m, 10H), 10.4 (s, 1H), 10.7 (br s, 1H), 10.8 (s, 1H), 12.0 (br s, 1H).

Step B. Preparation of N₁-(Nα-Caffeoyl-L-tryptophanyl)-N₂-(2-hydroxybenzoyl)-hydrazine The product obtained in step A of this example (353 mg, 0.8 mmol) was deprotected according to the indications of general procedure C. The product thus obtained was then coupled with caffeic acid (218 mg, 1.2 mmol) according to the indications of general procedure D. The reaction mixture was heated at 60° C. for 4 h. The crude product was purified by flash chromatography using successively 20%, 30% and 40% EtOAc/CH$_2$Cl$_2$/1% AcOH to give 117 mg (30%) of the final product as yellow crystals.

$^1$H NMR (DMSO-d$_6$): 3.0 (m, 2H), 4.8 (s, 1H), 6.3–7.9 (m, 14H), 8.3 (d, J=3.6, 1H), 9.2–12.0 (3×br s, 3×OH), 10.6 (s, 1H), 10.7 (br s, 1H), 10.8 (s, 1H).

Example 76

Preparation of N$_1$-(Nα-Caffeoyl-L-3,4-dihydroxyphenylalanyl)-N$_2$-(2-hydroxybenzoyl)-hydrazine (Compound No. 76)

Step A. Preparation of Nα-tert-Butoxycarbonyl-L-3,4-dihydroxyphenylalanine

The protection of L-3,4-dihydroxyphenylalanine (L-Dopa, 3.0 g, 15.2 mmol) was performed according to the indications of general procedure A using di-tert-butyl-dicarbonate (3.7 g, 17.0 mmol). The crude material was purified by flash chromatography using successively 10%, 30% and 40% EtOAc/CH$_2$Cl$_2$/1% AcOH to give 3.8 g, 84% of the desired compound as a white solid. The product was used for the next step without characterization.

Step B. Preparation of N$_1$-(Nα-tert-Butoxycarbonyl-L-3,4-dihydroxyphenylalanyl)-N$_2$-(2-hydroxybenzoyl)-hydrazine The title compound was prepared from Nα-tert-butoxycarbonyl-L-3,4-dihydroxyphenylalanine obtained in step A of this example (1.2 g, 3.94 mmol) by coupling it with salicylic hydrazide (901 mg, 5.9 mmol) following the indications of general procedure F. The crude material was purified by flash chromatography eluting first with 10% then 30% EtOAc/CH$_2$Cl$_2$ containing 1% AcOH to yield 0.9 g (53%) of the desired product as a white powder.

$^1$H NMR (DMSO-d$_6$): 1.3 (s, 9H), 2.6–3.0 (m, 2H), 6.6–8.0 (m, 8H), 9.2 (s, 1H), 10.4 (s, 1H), 10.7–12.0 (br s, 3×OH).

Step C. Preparation of N$_1$-(Nα-Caffeoyl-L-3,4-dihydroxyphenylalanyl)-N$_2$-(2-hydroxybenzoyl)-hydrazine The product obtained in step B of this example (581 mg, 1.35 mmol) was deprotected according to the indications of general procedure C. The product thus obtained was then coupled with caffeic acid (364 mg, 2.0 mmol) according to the indications of general procedure D. The reaction mixture was heated at 60° C. for 4 h. The crude product was purified by flash chromatography using successively 30%, 40% and 60% EtOAc/CH$_2$Cl$_2$/1% AcOH to give 224 mg (37%) of the final compound as yellow crystals.

LC-MS: 494 (M$^+$+H); >90% pure.

Example 77

Preparation of N$_1$-[Nα-(4,8-Dihydroxyquinoline-2-carbonyl)-L-tryptophanyl]-N$_2$-(2-hydroxybenzoyl)-hydrazine (Compound No. 77)

N$_1$-[Nα-(tert-Butoxycarbonyl)-L-tryptycarbonyl)-L-tryptophanyl]-//-6V$_2$-(2-hydroxybenzoyl)-hydrazine (1 mmol) prepared in example 75, step A was deprotected following the indications of general procedure C and coupled with 4,8-dihydroxyquinoline-2-carboxylic acid (885 mg, 4.3 mmol) using general procedure D. The final product was purified by flash chromatography using successively 30%, 40% and 50% EtOAc/CH$_2$Cl$_2$ to yield 528 mg, 35% of the title compound.

LC-MS: 526 (M$^+$+H); >95% pure.

Example 78

Preparation of N$_1$-[Nα-(4,8-Dihydroxyquinoline-2-carbonyl)-L-glutamyl]-N$_2$/Nδ-di-(2-hydroxybenzoyl)-dihydrazine (Compound No. 78)

Step A. Preparation of N$_1$-[Nα-(tert-Butoxycarbonyl)-L-glutamyl]-N$_2$,Nδ-di-(2-hydroxybenzoyl)-dihydrazine Commercially available Nα-(tert-butoxycarbonyl)-Oδ-benzyloxycarbonyl-L-glutamic acid (1.0 g, 2.96 mmol) was hydrogenolysed and coupled to salicylic hydrazide (1.35 g, 8.9 mmol) following the indications of general procedures E and F. Purification by flash chromatography using first 30% then 60% EtOAc/CH$_2$Cl$_2$ gave 1.0 g (68%) of the desired compound.

LC-MS: 516 (M$^+$+H); >98% pure.

Step B. Preparation of N$_1$-[Nα-(4,8-Dihydroxyquinoline-2-carbonyl)-L-glutamyl]-N$_2$,Nδ-di-(2-hydroxybenzoyl)-dihydrazine N$_1$-[Nα-(tert-butoxycarbonyl)-L-glutamyl]-N$_2$,Nδ-di-(2-hydroxybenzoyl)-dihydrazine (324 mg, 0.53 mmol) prepared in step A of this example was deprotected and coupled with 4,8-dihydroxyquinoline-2-carboxylic acid (165 mg, 0.8 mmol) using general procedures C and D. The final product was purified by flash chromatography using initially 60% then 80% EtOAc/CH$_2$Cl$_2$ and 5% MeOH/CH$_2$Cl$_2$ to yield 133 mg, 35% of the title compound.

$^1$H NMR (DMSO-d$_6$): 2.2–2.3 (m, 2H), 2.4 (d, J=2.3, 2H), 4.6 (s, 1H), 6.8–7.7 (m, 12H), 7.9 (d, J=4.0, 1H), 10.0 (br s, 4H), 10.5–11.3 (br s, 4×OH).

Example 79

Preparation of N$_1$-[Nα-tert-Butoxycarbonyl-Nτ-(2,4-dinitrophenyl)-L-histidinyl]-N$_2$-(2-hydroxybenzoyl)-hydrazine (Compound No. 79)

Commercially available Nα-tert-butoxycarbonyl-Nτ-(2,4-dinitrophenyl)-L-histidine (3.5 g, 7.3 mmol) was coupled with salycilic hydrazide (1.7 g, 11.0 mmol) as described in general procedure F. The crude material was purified by flash chromatography using a solvent gradient from 30% to 80% EtOAc/CH$_2$Cl$_2$/1% AcOH and 2.5% MeOH/EtOAc/1% AcOH. The product was obtained as white crystals (2.7 g, 60%).

$^1$H NMR (DMSO-d$_6$): 1.3 (s, 9H), 2.9 (m, 2H), 4.4 (d, J=4.6, 1H), 6.9–8.0 (m, 9H), 8.6 (d, J=8.3, 1H), 8.9 (s, OH), 10.3 and 10.6 (2×br s, 2×OH).

Example 80

Preparation of N$_1$-[Nα-Caffeoyl-Nτ-(2,4-dinitrophenyl)-L-histidinyl]-N$_2$-(2-hydroxybenzoyl)-hydrazine (Compound No. 80)

The product obtained in example 79, N$_1$-[Nα-tert-butoxycarbonyl-Nτ-(2,4-dinitrophenyl)-L-histidinyl]-N$_2$-(2-hydroxybenzoyl)-hydrazine (545 mg, 0.98 mmol), was deprotected and coupled with caffeic acid (265 mg, 1.5 mmol) using general procedures C and D. The final product was purified by flash chromatography using initially 50% then 90% EtOAc/CH$_2$Cl$_2$/1% AcOH followed by 5% MeOH/EtOAc/1% AcOH as the eluent to yield 103 mg, 17% of the title compound.

LC-MS: 618 (M$^+$+H); >90% pure.

Example 81

Preparation of N$_1$-[Nα-(3-(3'-thiophenyl)acryloyl)-Nτ-(2,4-dinitrophenyl)-L-histidinyl]-N$_2$-(2-hydroxybenzoyl)-hydrazine (Compound No. 81)

The product obtained in example 79, N$_1$-[Nα-tert-butoxycarbonyl-Nτ-(2,4-dinitrophenyl)-L-histidinyl]-N$_2$-(2-hydroxybenzoyl)-hydrazine (368 mg, 0.7 mmol), was deprotected and coupled with 3-(3'-thiophenyl)acrylic acid (153 mg, 1.0 mmol) using general procedures C and D. The final product was purified by flash chromatography using initially 20% and 99% EtOAc/CH$_2$Cl$_2$/1% AcOH followed by 5% MeOH/EtOAc/1% AcOH as the eluent to yield 141 mg, 36% of the title compound.

$^1$H NMR (DMSO-d$_6$): 2.8–3.2 (ABX, J=7.4, 15.0, 2H), 4.8 (s, 1H), 6.5–9.0 (m, 15H), 10.5 (s, 1H), 11.5 (br s, 2H).

Specific Examples for the Preparation of Derivatives of General Formula I'

Example 82

Preparation of N-(Nα-Caffeoyl-Nδ-trityl-L-glutaminyl)-2,5-dimethoxyaniline (Compound No. 82)

Step A. Preparation of N-[Nα-(9-Fluorenylmethoxycarbonyl)-Nδ-trityl-L-glutaminyl]-2,5-dimethoxyaniline Commercially available Nα-(9-fluorenylmethoxycarbonyl)-Nδ-trityl-L-glutamine (4.0 g, 6.55 mmol) was coupled with 2,5-dimethoxyaniline (1.5 g, 9.8 mmol) as described in general procedure F. The crude material was purified by flash chromatography eluting with 20% EtOAc/CH$_2$Cl$_2$. The product was obtained as white powder (4.4 g, 90%).

$^1$H NMR (DMSO-d$_6$): 1.8–2.1 (m, 2H), 2.4 (s, 2H), 3.68 and 3.68 (2×s, 6H), 6.6–7.9 (m, 27H), 8.6 (s, 1H), 9.0 (s, 1H).

Step B. Preparation of N-(Nα-Caffeoyl-Nδ-trityl-L-glutaminyl)-2,5-dimethoxyaniline The product obtained in step A of this example (539 mg, 0.72 mmol) was deprotected according to the indications of general procedure G. The product thus obtained was then coupled with caffeic acid (196 mg, 1.1 mmol) according to the indications of general procedure D. The reaction mixture was heated at 60° C. for 4 h. The crude product was purified by flash chromatography using successively 15%, 25% and 30% EtOAc/CH$_2$Cl$_2$/1% AcOH to give the desired product (230 mg, 46%) as yellow crystals.

$^1$H NMR (DMSO-d$_6$): 1.8–2.1 (m, 2H), 2.4 (t, J=7.2, 2H), 3.6 (s, 3H), 3.7 (s, 3H), 4.6 (d, J=6.0, 1H), 6.5 and 7.4 (2d, J=15.8, 2H), 6.6–8.0 (M, 21H), 8.4 (d, J=7.3, 1H), 8.7 (s, 1H), 9.2 (s, 1H), 9.4 (br s, 2×OH).

Example 83

Preparation of N-[Nα-(3,4-Dihydroxybenzoyl)-Nδ-trityl-L-glutaminyl]-2,5-dimethoxyaniline (Compound No. 83)

The title compound was prepared from N-[Nα-(9-fluorenylmethoxycarbonyl)-Nδ-trityl-L-glutaminyl]-2,5-dimethoxyaniline (531 mg, 0.7 mmol, example 82, step A) as described for example 82 (step B) using 3,4-dihydroxybenzoic acid (164 mg, 1.1 mmol) instead of caffeic acid. The crude material was purified by flash chromatography using first 10% then 30% EtOAc/CH$_2$Cl$_2$ containing 1% AcOH. The title compound was obtained as yellow crystals (164 mg, 35%).

$^1$H NMR (DMSO-d$_6$): 1.9–2.2 (m, 2H), 2.4 (t, J=7.4, 2H), 3.3 (s, 2H), 3.6 (s, 3H), 3.7 (s, 3H), 4.6 (s, 1H), 6.6–7.8 (M, 19H), 8.5 (d, J=7.0, 1H), 8.7 (s, 1H), 9.0 (s, 1H), 9.5 (s, 2×OH).

Example 84

Preparation of N-[Nα-(Indole-2-carbonyl)-Nδ-trityl-L-glutaminyl]-2,5-dimethoxyaniline (Compound No. 84)

The title compound was prepared from N-[Nα-(9-fluorenylmethoxycarbonyl)-Nδ-trityl-L-glutaminyl]-2,5-dimethoxyaniline (620 mg, 0.83 mmol, example 82, step A) as described for example 82 (step B) using indole-2-carboxylic acid (201 mg, 1.25 mmol) instead of caffeic acid. The crude material was purified by flash chromatography using initially 10% then 20% EtOAc/CH$_2$Cl$_2$. The title compound was obtained as white crystals (200 mg, 36%).

$^1$H NMR (DMSO-d$_6$): 1.9–2.2 (m, 2H), 2.5 (t, J=7.7, 2H), 3.6 (s, 3H), 3.7 (s, 3H), 6.6–7.9 (M, 24H), 8.7 (s, 1H), 8.8 (d, J=7.3, 1H), 9.1 (s, 1H), 11.6 (s, 1H).

Example 85

Preparation of N-[Nα-(4,8-Dihydroxyquinoline-2-carbonyl)-Nδ-trityl-L-glutaminyl]-2,5-dimethoxyaniline (Compound No. 85)

The title compound was prepared from N-[Nα-(9-fluorenylmethoxycarbonyl)-Nδ-trityl-L-glutaminyl]-2,5-dimethoxyaniline (703 mg, 0.94 mmol, example 82, step A) as described for example 82 (step B) using 4,8-dihydroxyquinoline-2-carboxylic acid (291 mg, 1.42 mmol) instead of caffeic acid. The crude material was purified by flash chromatography using initially 20% then 50% EtOAc/CH$_2$Cl$_2$. The title compound was obtained as white crystals (150 mg, 22%).

$^1$H NMR (DMSO-d$_6$): 2.0–2.3 (m, 2H), 2.5 (t, J=7.3, 2H), 3.6 (s, 6H), 4.8 (d, J=5.0, 1H), 6.6–7.8 (M, 22H), 8.7 (s, 1H), 9.2 (s, 1H), 9.8 (d, J=7.9, 1H), 10.0 (s, 1H), 11.8 (s, 1H).

Example 86

Preparation of N-[Nα-(3-(3'-Indole)acryloyl)-Nτ-trityl-L-histidinyl]dopamine (Compound No. 86)

The title compound was prepared from N-[Nα-(9-fluorenylmethoxycarbonyl)-Nτ-trityl-L-histidinyl]dopamine (805 mg, 1.07 mmol, example 13, step A) as described for example 13 (step B) using trans-3-indole acrylic acid (300 mg, 1.6 mmol) instead of caffeic acid. The crude material was purified by flash chromatography using a solvent gradient from 50% to 70% EtOAc/CH$_2$Cl$_2$/1% AcOH and 5% MeOH/CH$_2$Cl$_2$/1% AcOH as the eluent. The title compound was obtained as a yellow powder (262 mg, 35%).

$^1$H NMR (DMSO-d$_6$): 2.5 (t, J=8.7, 2H), 2.7–3.0 (ABX, J=14.3, 2H), 3.2 (t, J=5.7, 2H), 4.6 (d, J=5.4, 1H), 6.4–7.4 (M, 25H), 7.0–7.5 (2d, J=16.0, 2H), 7.9 (d, J=7.8, 1H), 8.0 (s, 1H), 8.8 (br s, 2×OH), 11.5 (s, 1H).

Example 87

Preparation of N-[Nα-(2-Thiopheneacetyl)-O-tert-butyl-L-seryl]d.U]dop.Une (Compound No. 87)

The title compound was prepared from N-[Nα-(9-fluorenylmethoxycarbonyl)-O-tert-butyl-L-seryl]dopamine (577 mg, 1.1 mmol, example 42, step A) as described for example 42 (step B) using 2-thiopheneacetic acid (242 mg, 1.7 mmol) instead of caffeic acid. The crude material was purified by flash chromatography using successively 20%, 30% and 50% EtOAc/CH$_2$Cl$_2$/1% AcOH as the eluent. The title compound was obtained as a white powder (120 mg, 26%).

$^1$H NMR (DMSO-d$_6$): 1.1 (s, 9H), 2.5 (s, 1H), 3.2 (m, 4H), 3.4 (s, 2H), 4.3 (d, J=4.3, 1H), 6.4–7.3 (M, 6H), 7.9 (s, 1H), 8.0 (d, J=6.9, 1H), 8.6 and 8.7 (2×s, 2×OH).

Example 88

Preparation of N-[Nα-(Pyrrole-2-carbonyl)-Nδ-trityl-L-glutaminyl]-2,5-dimethoxyaniline (Compound No. 88)

The title compound was prepared from N-[Nα-(9-fluorenylmethoxycarbonyl)-Nδ-trityl-L-glutaminyl]-2,5- dimethoxyaniline (988 mg, 1.33 mmol, example 82, step A) as described for example 82 (step B) using pyrrole-2-carboxylic acid (222 mg, 2.0 mmol) instead of caffeic acid. The crude material was purified by flash chromatography using successively 10%, 15% and 20% EtOAc/CH$_2$Cl$_2$. The title compound was obtained as white crystals (497 mg, 61%).

$^1$H NMR (DMSO-d$_6$): 1.9–2.2 (m, 2H), 2.5 (s, 2H), 3.6 (s, 3H), 3.7 (s, 3H), 4.5 (d, J=5.0, 1H), 6.1–7.8 (M, 21H), 8.3 (d, J=7.4, 1H), 8.7 (s, 1H), 9.1 (s, 1H), 11.5 (s, 1H).

Example 89

Preparation of N-[Nα-(N'-(4-Fluorobenzyl)indole-2-carbonyl)-Oδ-tert-butyl-L-glutamyl]benzylamine (Compound No. 89)

Step A. Preparation of N-(4-Fluorobenzyl)indole-2-carboxylic Acid

Indole-2-methyl Carboxylate

The title compound was prepared in a three step sequence starting from indole-2-carboxylic acid. Initially, indole-2-carboxylic acid (4.0 g, 24.8 mmol) dissolved into methanol (50 mL) was stirred in the presence of sulfuric acid (1 mL) for 8 h. Then, the methanol was evaporated and the residue treated with a saturated NaHCO$_3$ solution. The resulting mixture was extracted with EtOAc (3×50 mL) and evaporated in vacuo. The crude material, indole-2-methyl carboxylate, was used without purification in the next step.

LC-MS: 176 (M$^+$+H); >96% pure.

N-(4-Fluorobenzyl)indole-2-methyl Carboxylate

Indole-2-methyl carboxylate (4.7 g, 27 mmol) dissolved in dry DMF (50 mL) was treated with NaH (1.62 g, 40 mmol) for 1 h, under argon. Then, 4-fluorobenzyl bromide (6.63 g, 35 mmol) was added and the reaction mixture stirred at 23° C. for 16 h. The mixture was diluted with water and the organic layer was extracted with ethyl acetate. The combined organmbined organic phaseUwashed with brine and dried over magnesium sulfate. The solids were filtered off and solvent was evaporated under vacuum yielding a residue that was purified by silica gel chromatography using successively 5%, 10% and 20% EtOAc/hexane. The title compound was obtained as a yellow oil (7.2 g, 95%).

$^1$H NMR (CDCl$_3$): 3.8 (s, 3H), 5.8 (s, 2H), 7.0–7.7 (m, 9H).

N-(4-Fluorobenzyl)indole-2-carboxylic Acid

This compound was obtained by saponification of the corresponding ester. Therefore, N-(4-fluorobenzyl)indole-2-methyl carboxylate (4.0 g, 14 mmol) dissolved in methanol (50 mL) was treated with an aqueous solution of potassium hydroxide (1.7 g, 42 mmol). The reaction mixture was stirred at 70° C. for 2 h after which time HCl (1M) was added to pH 4.0. Then, the methanol was evaporated and the residue extracted with EtOAc (3×50 mL). The crude material was purified by flash chromatography eluting with 10% EtOAc/hexane to give 2.85 g (75%) of the product as white crystals.

$^1$H NMR (CDCl$_3$): 5.8 (s, 2H), 7.0–7.7 (m, 9H), 13.0 (br s, OH).

Step B. Preparation of N-[Nα-(9-Fluorenylmethoxycarbonyl)-Oδ-tert-butyl-L-glutamyl]benzylamine Commercially available Nα-(9-fluorenylmethoxycarbonyl)-Oδ-tert-butyl-L-glutamic acid (3.0 g, 7.0 mmol) was coupled with benzylamine (1.0 g, 10.0 mmol) as described in general procedure F. The crude material was purified by flash chromatography eluting with 100% CH$_2$Cl$_2$ followed by 20% and then 30% EtOAc/CH$_2$Cl$_2$. The product was obtained as white powder (3.4 g, 96%).

$^1$H NMR (DMSO-d$_6$): 1.4 (s, 9H), 1.9 (m, 2H), 2.2 (t, J=7.6, 2H), 4.0 (q, J=5.4, 1H), 4.3 (m, 5H), 7.2–7.9 (m, 14H), 8.4 (s, 1H).

Step C. Preparation of N-[Nα-(N'-(4-Fluorobenzyl)indole-2-carbonyl)-Oδ-tert-butyl-L-glutamyl]benzylamine The product obtained in step B of this example (571 mg, 1.1 mmol) was deprotected according to the indications of general procedure G. The product thus obtained was then coupled with N-(4-fluorobenzyl)indole-2-carboxylic acid (448 mg, 1.7 mmol, step A of this example) according to the indications of general procedure D. The reaction mixture was heated at 60° C. for 4 h. The crude product was purified by flash chromatography using successively 10%, 15% and 40% EtOAc/hexane to give the desired product (270 mg, 45%) as white crystals.

$^1$H NMR (DMSO-d$_6$): 1.4 (s, 9H), 1.9 (m, 2H), 2.3 (s, 2H), 4.3 (d, J=5.3, 2H), 4.5 (d, J=3.8, 1H), 5.8 (AB, J=13.6, 2H), 7.0–7.7 (m, 14H), 8.4 (s, 1H), 8.6 (d, J=7.6, 1H).

Example 90

Preparation of N-(Nα-Caffeoyl-Nδ-methyltrityl-L-glutaminyl)thiazole-2-amine (Compound No. 90)

Step A. Preparation of N-[Nα-(9-Fluorenylmethoxycarbonyl)-Nδ-methyltrityl-L-glutaminyl)thiazole-2-amine Commercially available Nα-(9-fluorenylmethoxycarbonyl)-Nδ-methyltrityl-L-glutamine (4.0 g, 6.4 mmol) was coupled with 2-aminothiazole (961 mg, 9.6 mmol) as described in general procedure F. The crude material was purified by flash chromatography eluting with 40% EtOAc/CH$_2$Cl$_2$. The product was obtained as white powder (2.7 g, 60%).

$^1$H NMR (DMSO-d$_6$): 1.9 (m, 2H), 2.2 (m, 3H), 2.4 (m, 2H), 4.2 (m, 4H), 7.1–7.5 (m, 24H), 7.7 (d, J=6.0, 1H), 8.0 (d, J=7.2, 1H), 12.2 (br s, 1H).

Step B. Preparation of N-(Nα-Caffeoyl-Nδ-trityl-L-glutaminyl)thiazole-2-amine

The product obtained in step A of this example (998 mg, 1.4 mmol) was deprotected according to the indications of general procedure G. The product thus obtained was then coupled with caffeic acid (382 mg, 2.0 mmol) according to the indications of general procedure D. The reaction mixture was heated at 60° C. for 4 h. The crude product was purified by flash chromatography using successively 10%, 25% and 30% EtOAc/CH$_2$Cl$_2$/1% AcOH to give the desired product (274 mg, 30%) as yellow crystals.

$^1$H NMR (DMSO-d$_6$): 1.9 (m, 2H), 2.2 (s, 3H), 2.5 (m, 2H), 4.5 (s, 1 H), 6.4 and 7.0 (2d, J=16.0, 2H), 6.7–7.7 (m, 18H), 8.0 (s, 1 H), 8.3 (d, J=6.5, 1H), 8.6 (s, 1H), 9.1 and 9.4 (2×br s, 2×OH), 12.2 (br s, 1H).

Example 91

Preparation of N-(Nα-(Pyrrole-2-carbonyl)-L-glutaminyl]-2,5dimethoxyaniline (Compound No. 91)

The product of example 88, N-[Nα-(pyrrole-2-carbonyl)-Nδ-trityl-L-glutaminyl]-2,5-dimethoxyaniline (427 mg, 0.7 mmol), was deprotected using the indications of general procedure C. The resulting crude material was purified by flash chromatography using successively 50%, 70% and 100% EtOAc/CH$_2$Cl$_2$ followed by 5% MeOH/EtOAc to yield 120 mg (46%) of the desired product as white crystals.

$^1$H NMR (DMSO-d$_6$): 2.0 (m, 2H), 2.3 (s, 2H), 3.6 (s, 3H), 3.7 (s, 3H), 4.5 (d, J=2.2, 1H), 6.1–7.0 (m, 6H), 7.3 (s, 1H), 7.8 (s, 1H), 8.4 (d, J=6.6, 1H), 9.1 (s, 1H), 11.5 (s, 1H).

Example 92

Preparation of N-[Nα-(N'-(4-Fluorobenzyl)indole-2-carbonyl)-Nδ-methyltrityl-L-glutaminyl]-2,5-dimethoxyaniline (Compound No. 92)

Step A. Preparation of N-[Nα-(9-Fluorenylmethoxycarbonyl)-Nδ-methyltrityl-L-glutaminyl]-2,5-dimethoxyaniline Commercially available Nα-(9-fluorenylmethoxycarbonyl)-Nδ-methyltrityl-L-glutamine (4.0 g, 6.55 mmol) was coupled with 2,5-dimethoxyaniline (1.5 g, 9.8 mmol) as described in general procedure F. The crude material was purified by flash chromatography eluting with 20% EtOAc/CH$_2$Cl$_2$. The product was obtained as white powder (4.4 g, 90%).

LC-MS: 760 (M$^+$+H); >96% pure.

Step B. Preparation of N-[Nα-(N'-(4-Fluorobenzyl)indole-2-carbonyl)-Nδ-methyltrityl-L-glutaminyl]-2,5-dimethoxyaniline The product obtained in step A of this example (480 mg, 0.6 mmol) was deprotected according to the indications of general procedure G. The product thus obtained was then coupled with N-(4-fluorobenzyl)indole-2-carboxylic acid (260 mg, 0.9 mmol, example 89 (step A)) according to the indications of general procedure D. The reaction mixture was heated at 60° C. for 4 h. The crude product was purified by flash chromatography using 20% EtOAc/hexane and successively 5% then 20% EtOAc/CH$_2$Cl$_2$ to give the desired product (200 mg, 40%) as yellow crystals.

$^1$H NMR (DMSO-d$_6$): 1.9–2.2 (m, 5H), 2.5 (m, 2H), 3.6 (s, 3H), 3.7 (s, 3H), 4.6 (d, J=3.8, 1H), 5.8 (q, J=11.0, 2H), 6.6–7.9 (m, 26H), 8.7 (s, 1H), 9.0 (d, J=7.0, 1H), 9.2 (s, 1H).

Example 93

Preparation of N-[Nα-(N'-(4-Fluorobenzyl)pyrrole-2-carbonyl)-O-tert-butyl-L-seryl]dopamine (Compound No. 93)

Step A. Preparation of N-(4-Fluorobenzyl)pyrrole-2-carboxylic Acid

N-(4-Fluorobenzyl)pyrrole-2-(4-fluorobenzyl) carboxylate

Commercially available pyrrole-2-carboxylic acid (1.0 g, 9.0 mmol) was benzylated according to the indications of general procedure B (a). The crude material was purified by flash chromatography using successively 100% hexane and 5% EtOAc/hexane as the eluent. The final product was obtained as an oil (2.7 g, 96%).

LC-MS: 314 (M$^+$+H); >97% pure.

N-(4-Fluorobenzyl)pyrrole-2-carboxylic Acid

This compound was prepared by saponification of N-(4-fluorobenzyl)pyrrole-2-(4-fluorobenzyl)carboxylate following the indications of example 89, step A for the saponification of N-(4-fluorobenzyl)indole-2-methyl carboxylate. Upon acidification, the product crystallized and was purified by filtration to give 1.6 g (89%) of the acid.

LC-MS: 206 (M$^+$+H); >90% pure.

Step B. Preparation of N-[Nα-(N'-(4-Fluorobenzyl)pyrrole-2-carbonyl)-O-tert-butyl-L-seryl]dopamine The title compound was prepared from N-[Nα-(9-fluorenylmethoxycarbonyl)-O-tert-butyl-L-seryl]dopamine (429 mg, 0.8 mmol, example 42, step A) as described for example 42 (step B) using N-(4-fluorobenzyl)pyrrole-2-carboxylic acid (168 mg, 1.2 mmol, step A of this example) instead of caffeic acid. The crude material was purified by flash chromatography using successively 10%, 20% and 45% EtOAc/CH$_2$Cl$_2$ as the eluent. The title compound was obtained as a white powder (164 mg, 40%).

$^1$H NMR (DMSO-d$_6$): 1.1 (s, 9H), 2.5 (s, 2H), 3.2 (m, 2H), 3.5 (m, 2H), 4.4 (d, J=4.8, 1H), 5.5 (AB, J=12.3, 2H), 6.2–7.2 (m, 10H), 7.7 (d, J=7.5, 1H), 7.9 (s, 1H), 8.6 and 8.7 (2×s, 2×OH).

Example 94

Preparation of N-[Nα-(N'-(4-Fluorobenzyl)indole-2-carbonyl)-L-glutamyl]benzylamine (Compound No. 94)

The product of example 89, N-[Nα-(N'-(4-fluorobenzyl)indole-2-carbonyl)-Oδ-tert-butyl-L-glutamyl]benzylamine (125 mg, 0.23 mmol), was deprotected using the indications of general procedure C. The resulting crude material was purified by flash chromatography using successively 30% EtOAc/hexane, 20% EtOAc/CH$_2$Cl$_2$ and 20% EtOAc/CH$_2$Cl$_2$/1% AcOH to yield 100 mg (80%) of the desired product as a yellow powder.

$^1$H NMR (DMSO-d$_6$): 2.0 (m, 2H), 2.3 (s, 2H), 4.3 (d, J=4.5, 2H), 4.4 (q, J=4.9, 1H), 5.8 (q, J=2.2, 2H), 7.0–7.7 (m, 14H), 8.4 (t, J=5.4, 1H), 8.6 (d, J=7.5, 1H), 12.1 (br s, OH).

Example 95

Preparation of N-[Nα-(N'-(4-Fluorobenzyl)indole-2-carbonyl)-O-tert-butyl-L-seryl]dopamine (Compound No. 95)

The title compound was prepared from N-[Nα-(9-fluorenylmethoxycarbonyl)-O-tert-butyl-L-seryl]dopamine (633 mg, 1.2 mmol, example 42, step A) as described for example 42 (step B) using N-(4-fluorobenzyl)indole-2-carboxylic acid (493 mg, 1.8 mmol, example 89 (step A)) instead of caffeic acid. The crude material was purified by flash chromatography using successively 10%, 20% and 30% EtOAc/CH$_2$Cl$_2$ as the eluent. The title compound was obtained as a yellow powder (270 mg, 40%).

$^1$H NMR (DMSO-d$_6$): 1.1 (s, 9H), 2.5 (t, J=7.5, 2H), 3.2 (m, 2H), 3.6 (m, 2H), 4.5 (q, J=6.6, 1H), 5.8 (q, J=7.0, 2H), 6.4–7.7 (m, 12H), 8.0 (t, J=5.3, 1H), 8.4 (d, J=7.9, 1H), 8.6 and 8.7 (2×s, 2×OH).

Example 96

Preparation of N-[Nα-(N'-(4-Fluorobenzyl)indole-2-carbonyl)-L-seryl]dopamine (Compound No. 96)

The product of example 95, N-[Nα-(N'-(4-fluorobenzyl)indole-2-carbonyl)-O-tert-butyl-L-seryl]dopamine (120 mg, 0.22 mmol), was deprotected using the indications of general procedure C. The resulting crude material was purified by flash chromatography using successively 30%, 60% and 80% EtOAc/CH$_2$Cl$_2$ to yield 40 mg (37%) of the desired product as yellow crystals.

$^1$H NMR (DMSO-d$_6$): 2.5 (d, J=8.2, 2H), 3.2 (m, 2H), 3.7 (s, 2H), 4.4 (d, J=5.6, 1H), 4.9 (br s, OH), 5.8 (AB, J=9.0, 2H), 6.4–7.7 (m, 12H), 7.9 (s, 1H), 8.3 (d, J=7.6, 1H), 8.6 and 8.7 (2×s, 2×OH).

Example 97

Preparation of N-[Nα-(3,4-di-(4-Fluorobenzyloxy)benzoyl)-O-tert-butyl-L-seryl]dopamine (Compound No. 97)

Step A. Preparation of 3,4-di-(4-Fluorobenzyloxy)benzoic Acid

The title compound was prepared from commercially available 3,4-dihydroxybenzoic acid (3.0 g, 19.5 mmol) fom 5Ummol) following 5Usequence of reaction used to prepare N-(4-fluorobenzyl)indole-2-carboxylic acid described in example 89 step A. The crude material was filtered to yield 6.6 g, 92% of the desired material as a white solid.

LC-MS: 371 (M$^+$+H); >96% pure.

Step B. Preparation of N-[Nα-(3,4-di-(4-Fluorobenzyloxy) benzoyl)-O-tert-butyl-L-seryl]dopamine The title compound was prepared from N-[Nα-(9-fluorenylmethoxycarbonyl)-O-tert-butyl-L-seryl]dopamine (610 mg, 1.2 mmol, example 42, step A) as described for example 42 (step B) using 3,4-di-(4-fluorobenzyloxy) benzoic acid (653 mg, 1.8 mmol, step A of this example) instead of caffeic acid. The crude material was purified by flash chromatography using successively 15%, 35% and 50% EtOAc/CH$_2$Cl$_2$ as the eluent. The title compound was obtained as a yellow powder (207 mg, 27%).

$^1$H NMR (DMSO-d$_6$): 1.1 (s, 9H), 2.5 (t, J=7.3, 2H), 3.2 (m, 2H), 3.6 (m, 2H), 4.5 (q, J=6.7, 1H), 5.1 (AB, J=13.9, 4H), 6.4–7.6 (m, 14H), 7.9 (t, J=5.0, 1H), 8.1 (d, J=7.8, 1H), 8.6 and 8.7 (2×s, 2×OH).

Example 98

Preparation of N-[Nα-(3,4-di-(4-Fluorobenzyloxy) caffeoyl)-glycyl]-2-(2'-thiophenyl)ethylamine (Compound No. 98)

Step A. Preparation of N-[3,4-di-(4-Fluorobenzyloxy) caffeoyl]-glycine

Commercially available glycine tert-butyl ester (3.0 g, 23 mmol) was coupled with caffeic acid (6.2 g, 34.5 mmol) following the conditions of general procedure D. The intermediate thus obtained was benzylated and deprotected following the indications of general procedures B (a) and C. The crude material was purified by flash chromatography using successively 10%, 20% and 30% EtOAc/CH$_2$Cl$_2$ to yield 2.3 g, 60% of the desired material as a yellowish oil.

LC-MS: 454 (M$^+$+H); >90% pure.

Step B. Preparation of N-[Nα-(3,4-di-(4-Fluorobenzyloxy) caffeoyl)-L-glycyl]-2-(2'-thiophenyl)ethylamine The product obtained in step A of this example (227 mg, 0.5 mmol) was coupled with 2-thiopheneethylamine (96 mg, 0.75 mmol) as described in general procedure F. Flash chromatography of the crude using successively 10%, 40% and 70% EtOAc/CH$_2$Cl$_2$ as the eluent gave 112 mg (40%) of the desired material as a yellow powder.

LC-MS: 563 (M$^+$+H); >90% pure.

Example 99

Preparation of N-[Nα-(3,4-di-(4-Fluorobenzyloxy) benzoyl)-Oδ-tert-butyl-L-glutamyl]benzylamine (Compound No. 99)

The title compound was prepared from N-[Nα-(9-fluorenylmethoxycarbonyl)-Oδ-tert-butyl-L-glutamyl] benzylamine (600 mg, 1.2 mmol, example 89, step A) as described for example 89 (step B) using 3,4-di-(4-fluorobenzyl)benzoic acid (647 mg, 1.75 mmol) instead of N-(4-fluorobenzyl)indole-2-carboxylic acid. The crude material was purified by flash chromatography using successively 15%, 20% and 35% EtOAc/CH$_2$Cl$_2$ as the eluent. The title compound was obtained as a yellow powder (134 mg, 14%).

$^1$H NMR (DMSO-d$_6$): 1.3 (s, 9H), 2.0 (m, 2H), 2.2 (m, 2H), 4.2 (m, 2H), 4.4 (d, J=4.4, 1H), 5.1 (AB, J=10.2, 4H), 7.1–7.6 (m, 16H), 8.3 (d, J=7.3, 1H), 8.4 (d, J=4.8, 1H).

Example 100

Preparation of N-[Nα-(3,4-di-(4-Fluorobenzyloxy) caffeoyl)-L-glycyl)dopamine (Compound No. 100)

N-[3,4-di-(4-fluorobenzyloxy)caffeoyl]-glycine (661 mg, 1.5 mmol, example 98 (step A)) was coupled with dopamine hydrochloride (417 mg, 2.2 mmol) as described in general procedure F. Flash chromatography of the crude using successively 40%, 60% and 90% EtOAc/CH$_2$Cl$_2$ as the eluent gave 334 mg (39%) of the desired material as a yellow powder.

LC-MS: 589 (M$^+$+H); >90% pure.

Example 101

Preparation of N-[Nα-(N'-(4-Fluorobenzyl)pyrrole-2-carbonyl)-Oδ-tert-butyl-L-glutamyl]-2-(2'-thiophenyl)ethylamine (Compound No. 101)

Step A. Preparation of N-[Nα-(9-Fluorenylmethoxycarbonyl)-Oδ-tert-butyl-L-glutamyl]-2-(2'-thiophenyl)ethylamine Commercially available Nα-(9-fluorenylmethoxycarbonyl)-Oδ-tert-butyl-L-glutamic acid (4.0 g, 5 9.4 mmol) was coupled with 2-thiopheneethylamine (1.8 g, 14.0 mmol) as described in general procedure F. The crude material was purified by flash chromatography using successively 10% and 40% EtOAc/hexane followed by 20% EtOAc/CH$_2$Cl$_2$ as the eluent. The product was obtained as white powder (4.2 g, 83%).

$^1$H NMR (DMSO-d$_6$): 1.3 (s, 9H), 1.8 (m, 2H), 2.2 (t, J=6.6, 2H), 2.9 (t, J=6.0, 2H), 3.3 (m, 2H), 3.9 (d, J=4.9, 1H), 4.1 (m, 3H), 6.8–7.9 (m, 11H), 7.5 (d, J=7.4, 1H), 8.0 (s, 1H),

Step B. Preparation of N-[Nα-(N'-(4-Fluorobenzyl)pyrrole-2-carbonyl)-Oδ-tert-butyl-L-glutamyl]-2-(2'-thiophenyl) ethylamine The product obtained in step A of this example (647 mg, 1.2 mmol) was deprotected according to the indications of general procedure G. The product thus obtained was then coupled with N-(4-fluorobenzyl)pyrrole-2-carboxylic acid (448 mg, 1.7 mmol, example 93 (step A)) according to the indications of general procedure D. The reaction mixture was heated at 60° C. for 4 h. The crude product was purified by flash chromatography using successively 10%, 35% and 60% EtOAc/hexane to give the desired product (450 mg, 72%) as white crystals.

$^1$H NMR (DMSO-d$_6$): 1.3 (s, 9H), 1.9 (m, 2H), 2.2 (t, J=7.5, 2H), 2.9 (t, J=6.9, 2H), 3.3 (m, 2H), 4.3 (q, J=5.3, 1H), 5.5 (AB, J=14.7, 2H), 6.1–7.3 (m, 10H), 8.0 (m, 2H).

Example 102

Preparation of N-[Nα-(N'-(4-Fluorobenzyl)indole-2-carbonyl)-Oδ-tert-butyl-L-glutamyl]-2-(2'-thiophenyl)ethylamine (Compound No. 102)

The title compound was prepared from N-[Nα-(9-fluorenylmethoxycarbonyl)-Oδ-tert-butyl-L-glutamyl]-2-(2'-thiophenyl)ethylamine (754 mg, 1.4 mmol, example 101, step A) as described for example 101 (step B) using N-(4-fluorobenzyl)indole-2-carboxylic acid (570 mg, 2.1 mmol, example 89 (step A)) instead of N-(4-fluorobenzyl)pyrrole-2-carboxylic acid. The crude material was purified by flash chromatography using successively 10%, 20% and 30% EtOAc/hexane as the eluent. The title compound was obtained as white crystals (655 mg, 82%).

$^1$H NMR (DMSO-d$_6$): 1.3 (s, 9H), 1.9 (m, 2H), 2.2 (t, J=8.0, 2H), 2.9 (t, J=6.8, 2H), 3.3 (m, 2H), 4.4 (q, J=5.2, 1H), 5.8 (AB, J=15.4, 2H), 6.8–7.7 (m, 12H), 8.0 ((t, J=4.9, 1H), 8.5 (d, J=8.4, 1H).

Example 103

Preparation of N-[Nα-(N'-(4-Fluorobenzyl)pyrrole-2-carbonyl)-L-glutamyl]-2-(2'-thiophenyl) ethylamine (Compound No. 103)

N-[Nα-(N'-(4-Fluorobenzyl)pyrrole-2-carbonyl)-Oδ-tert-butyl-L-glutamyl]-2-(2'-thiophenyl)ethylamine obtained in example 101 (180 mg, 0.35 mmol) was deprotected according to the indications of general procedure C. The crude material was purified by flash chromatography eluting successively with 30% and 80% EtOAc/CH$_2$Cl$_2$ to yield 40 mg (25%) of the title compound as white crystals.

$^1$H NMR (DMSO-d$_6$): 1.9 (m, 2H), 2.2 (t, J=6.9, 2H), 2.9 (t, J=6.8, 2H), 3.3 (m, 2H), 4.3 (d, J=5.3, 1H), 5.5 (AB, J=14.6, 2H), 6.1–7.3 (m, 10H), 8.0 (m, 2H), 12.1 (br s, OH).

Example 104

Preparation of N-[Nα-(N'-(4-Fluorobenzyl)indole-2-carbonyl)-L-glutamyl]-2-(2'-thiophenyl)ethylamine (Compound No. 104)

N-[Nα-(N'-(4-fluorobenzyl)indole-2-carbonyl)-Oδ-tert-butyl-L-glutamyl]-2-(2'-thiophenyl)ethylamine obtained in example 102 (465 mg, 0.83 mmol) was deprotected according to the indications of general procedure C. The crude material was purified by flash chromatography eluting with 30% EtOAc/CH$_2$Cl$_2$ to yield 300 mg (65%) of the title compound as white crystals.

$^1$H NMR (DMSO-d$_6$): 2.0 (m, 2H), 2.3 (t, J=7.5, 2H), 2.9 (t, J=6.8, 2H), 3.3 (m, 2), 4.4 (q, J=4.7, 1H), 5.8 (AB, J=15.7, 2H), 6.9–7.7 (m, 12H), 8.1 (t, J=4.6, 1H), 8.6 (d, J=8.0, 1H), 12.2 (br s, OH).

Example 105

Preparation of N-[Nα-(4,8-Dihydroxyquinoline-2-carbonyl)-Oδ-tert-butyl-L-glutamyl]-2-(2'-thiophenyl)ethylamine (Compound No. 105)

The title compound was prepared from N-[Nα-(9-fluorenylmethoxycarbonyl)-Oδ-tert-butyl-L-glutamyl]-2-(2'-thiophenyl)ethylamine (711 mg, 1.3 mmol, example 101, step A) as described for example 101 (step B) using 4,8-dihydroxyquinoline-2-carboxylic acid (410 mg, 2.0 mmol) instead of N-(4-fluorobenzyl)pyrrole-2-carboxylic acid. The crude material was purified by flash chromatography using successively 15%, 30% and 60% EtOAc/CH$_2$Cl$_2$. The title compound was obtained as yellow crystals (244 mg, 37%).

$^1$H NMR (DMSO-d$_6$): 1.3 (s, 9H), 1.9–2.1 (m, 2H), 2.3 (m, 2H), 2.9 (t, J=7.0, 2H), 3.2–3.4 (m, 2H), 4.5 (d, J=5.4, 1H), 6.8–7.5 (m, 7H), 8.1 (s, 1H), 9.5 (d, J=8.3, 1H), 10.0 (s, OH), 11.7 (s, OH).

Example 106

Preparation of N-[Nα-(4,8-Dihydroxyquinoline-2-carbonyl)-L-glutamyl]-2-(2'-thiophenyl)ethylamine (Compound No. 106)

N-[Nα-(4,8-dihydroxyquinoline-2-carbonyl)-Oδ-tert-butyl-L-glutamyl]-Ul-2'-thiophenyl)ethylamine thiophenyl) ethylamine obtained in example 105 (160 mg, 0.32 mmol) was deprotected according to the indications of general procedure C. The crude material was purified by flash chromatography eluting with EtOAc to yield 100 mg (70%) of the title compound as yellow crystals.

$^1$H NMR (DMSO-d$_6$): 1.9–2.1 (m, 2H), 2.3 (m, 2H), 2.9 (t, J=6.6, 2H), 3.2–3.4 (m, 2H), 4.5 (d, J=5.4, 1H), 6.9–7.6 (m, 7H), 8.2 (s, 1H), 9.4 (d, J=6.4, 1H), 10.1 and 11.9 (2×br s, 2×OH), 13.5 (br s, OH).

Example 107

Preparation of N-[Nα-(5-Fluoro-2-hydroxybenzoyl)-Oδ-tert-butyl-L-glutamyl]-2-(2'-thiophenyl)ethylamine (Compound No. 107)

The title compound was prepared from N-[Nα-(9-fluorenylmethoxycarbonyl)-Oδ-tert-butyl-L-glutamyl]-2-(2'-thiophenyl)ethylamine (733 mg, 1.4 mmol, example 101, step A) as described for example 101 (step B) using 5-fluoro-2-hydroxybenzoic acid (321 mg, 2.0 mmol) instead of N-(4-fluorobenzyl)pyrrole-2-carboxylic acid. The crude material was purified by flash chromatography using successively 5%, 10% and 20% EtOAc/hexane as the eluent. The title compound was obtained as white crystals (400 mg, 65%).

$^1$H NMR (DMSO-d$_6$): 1.4 (s, 9H), 1.9–2.1 (m, 2H), 2.3 (t, J=7.4, 2H), 2.9 (t, J=6.5, 2H), 3.3 (m, 2H), 4.5 (d, J=5.0, 1H), 6.7–7.3 (m, 6H), 8.1 (s, 1H), 8.3 (t, J=4.6, 1H), 11.4 (s, OH).

Example 108

Preparation of N-[Nα-(5-Fluoro-2-hydroxybenzoyl)-L-glutamyl]-2-(2'-thiophenyl)ethylamine (Compound No. 108)

N-[Nα-(5-fluoro-2-hydroxybenzoyl)-Oδ-tert-butyl-L-glutamyl]-2-(2'-thiophenyl)ethylamine obtained in example 107 (200 mg, 0.4 mmol) was deprotected according to the indications of general procedure C. The crude material was purified by flash chromatography eluting with 30% EtOAc/CH$_2$Cl$_2$ and 100% EtOAc to yield 87 mg (50%) of the title compound as yellow crystals.

$^1$H NMR (DMSO-d$_6$): 1.9–2.1 (m, 2H), 2.3 (t, J=7.4, 2H), 2.9 (t, J=6.5, 2H), 3.3 (m, 2H), 4.5 (d, J=5.0, 1H), 6.7–7.3 (m, 6H), 8.1 (s, 1H), 8.3 (t, J=4.6, 1H), 11.4 (s, OH).

Example 109

N-[Nα-(N'-(4-Fluorobenzyl)indole-2-carbonyl)-Nδ-trityl-L-glutaminyl]-3-hydroxy-4-methoxyaniline (Compound No. 109)

Step A. Preparation of N-[Nα-(9-Fluorenylmethoxycarbonyl)-Nδ-trityl-L-glutaminyl]-3-hydroxy-4-methoxyaniline Commercially available Nα-(9-fluorenylmethoxycarbonyl)-Nδ-trityl-L-glutamine (4.0 g, 7.2 mmol) was coupled with 3-hydroxy-4-methoxyaniline (1.0 g, 7.2 mmol) as described in general procedure F. The crude material was purified by flash chromatography eluting with 100% CH$_2$Cl$_2$ and 30% EtOAc/CH$_2$Cl$_2$. The product was obtained as white powder (4.0 g, 88%).

LC-MS: 732 (M$^+$+H); >95% pure.

Step B. Preparation of N-[Nα-(N'-(4-Fluorobenzyl)indole-2-carbonyl)-Nδ-trityl-L-glutaminyl]-3-hydroxy-4-methoxyaniline The product obtained in step A of this example (590 mg, 0.8 mmol) was deprotected according to the indications of general procedure G. The product thus obtained was then coupled with N-(4-fluorobenzyl)indole-2-carboxylic acid (323 mg, 1.2 mmol, example 89 (step A)) according to the indications of general procedure D. The reaction mixture was heated at 60° C. for 4 h. The crude product was purified by flash chromatography using successively 5% and 10% EtOAc/CH$_2$Cl$_2$ to give the desired product (400 mg, 65%) as white crystals.

$^1$H NMR (DMSO-d$_6$): 1.9–2.1 (m, 2H), 2.5 (m, 2H), 3.7 (s, 3H), 4.4 (m, 1H), 5.8 (s, 2H), 6.8–7.6 (m, 27H), 8.6 (s, 1H), 8.7 (d, J=7.0, 1H), 9.0 (s, 1H), 9.7 (s, OH).

Example 110

N-[Nα-(N'-(4-Fluorobenzyl)indole-2-carbonyl)-L-glutaminyl]-3-hydroxy-4-methoxyaniline (Compound No. 110)

The product of example 109, N-[Nα-(N'-(4-fluorobenzyl)indole-2-carbonyl)-Nδ-trityl-L-glutaminyl]-3-hydroxy-4- methoxyaniline (160 mg, 0.2 mmol), was deprotected using the indications of general procedure C. The resulting crude material was purified by flash chromatography using successively 30% and 50% EtOAc/CH$_2$Cl$_2$ followed by 100% EtOAc to yield 60 mg (55%) of the desired product as white crystals.

$^1$H NMR (DMSO-d$_6$): 1.9–2.1 (m, 2H), 2.3 (m, 2H), 3.7 (s, 3H), 4.4 (q, J=6.0, 1H), 5.7 (AB, J=2.0, 2H), 6.8–7.7 (m, 14H), 8.8 (d, J=7.0, 1H), 9.0 (s, 1H), 9.8 (s, OH).

Example 111

Preparation of N-[Nα-(3,4-di-(4-Fluorobenzyloxy) benzoyl)-Nδ-trityl-L-glutaminyl]-3-hydroxy-4-methoxyaniline (Compound No. 111)

The title compound was prepared from N-[Nα-(9-fluorenylmethoxycarbonyl)-Nδ-trityl-L-glutaminyl]-3-hydroxy-4-methoxyaniline (642 mg, 0.9 mmol, example 109, step A) as described for example 109 (step B) using 3,4-di-(4-fluorobenzyloxy)benzoic acid (485 mg, 1.3 mmol) instead of N-(4-fluorobenzyl)indole-2-carboxylic acid. The crude material was purified by flash chromatography using successively 5%, 10% and 30% EtOAc/CH$_2$Cl$_2$ as the eluent. The title compound was obtained as white crystals (260 mg, 34%).

$^1$H NMR (DMSO-d$_6$): 1.9–2.1 (m, 2H), 2.5 (m, 2H), 3.7 (s, 3H), 4.5 (d, J=5.9, 1H), 5.1 (s, 2H), 5.2 (s, 2H), 6.8–7.6 (m, 29H), 8.5 (d, J=6.7, 1H), 8.7 (s, 1H), 9.0 (s, 1H), 9.8 (s, OH)

Example 112

Preparation of N-[Nα-(3,4-di-(4-Fluorobenzyloxy) caffeoyl)-Nδ-trityl-L-glutaminyl]-3-hydroxy-4-methoxyaniline (Compound No. 112)

The title compound was prepared from N-[Nα-(9-fluorenylmethoxycarbonyl)-Nδ-trityl-L-glutaminyl]-3-hydroxy-4-methoxyaniline (565 mg, 0.8 mmol, example 109, step A) as described for example 109 (step B) using 3,4-di-(4-fluorobenzyloxy)caffeic acid (459 mg, 1.2 mmol) instead of N-(4-fluorobenzyl)indole-2-carboxylic acid. The crude material was purified by flash chromatography using successively 15%, 20% and 30% EtOAc/CH$_2$Cl$_2$ as the eluent. The title compound was obtained as white crystals (250 mg, 37%).

$^1$H NMR (DMSO-d$_6$): 1.9–2.1 (m, 2H), 2.3 (m, 2H), 3.7 (s, 3H), 4.5 (d, J=5.2, 1H), 5.0 (s, 4H), 6.6 and 7.4 (2d, J=15.7, 2H), 6.8–7.5 (m, 29H), 8.2 (d, J=6.8, 1H), 8.6 (s, 1H), 9.0 (s, 1H), 9.8 (s, OH).

Example 113

Preparation of N-[Nα-(5-Fluoroindole-2-carbonyl)-Nδ-trityl-L-glutaminyl]-3-hydroxy-4-methoxyaniline (Compound No. 113)

The title compound was prepared from N-[Nα-(9-fluorenylmethoxycarbonyl)-Nδ-trityl-L-glutaminyl]-3-hydroxy-4-methoxyaniline (605 mg, 0.8 mmol, example 109, step A) as described for example 109 (step B) using 5-fluoroindole-2-carboxylic acid (222 mg, 1.24 mmol) instead of N-(4-fluorobenzyl)indole-2-carboxylic acid. The crude material was purified by flash chromatography using 10, 20 and 40% EtOAc/CH$_2$Cl$_2$ as the eluent. The title compound was obtained as yellow crystals (400 mg, 72%).

$^1$H NMR (DMSO-d$_6$): 1.9–2.1 (m, 2H), 2.5 (m, 2H), 3.7 (s, 3H), 4.5 (d, J=5.5, 1H), 6.8–7.5 (m, 22H), 8.6 (d, J=7.0, 1H), 8.7 (s, 1H), 9.0 (s, 1H), 9.8 (s, 1H), 11.7 (s, OH).

As mentioned above, the activities for compounds illustrated in the examples are set forth in Tables 1 to 4 below. For the purposes of Table 1 to 4 the HIV-1 integrase inhibition assay was based on a known procedure (Hazuda, D. J. et al., Nucleic Acids Res. 22 1121–1122 (1994)).

TABLE 1

For table 1 (below) the compounds are of the following structure

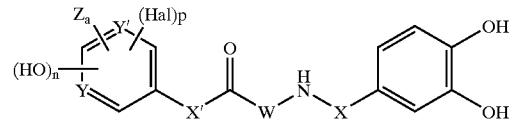

| Example No. | Ar—X'—C=O [Basic Group] | W [Residue of] | X | Y/Y' | Za | (Hal)p p | n | IC$_{50}$ (nM) | D, L, DL |
|---|---|---|---|---|---|---|---|---|---|
| 1 | 3,4-Dihydroxybenzoyl | Oγ—C$_6$H$_{11}$—Asp | CH$_2$CH$_2$ | C/C | H | — | 2 | 34000 | L |
| 2 | 3-Amino-4-hydroxybenzoyl | Nτ-trityl-His | CH$_2$CH$_2$ | C/C | 3-NH$_2$ | — | 1 | >5000 | D |
| 3 | 3,4-dihydroxybenzoyl | Nε(3,4-dihydroxybenzoyl)-Lys | Single Bond | C/C | H | — | 2 | 14000 | L |
| 4 | 2,4-Dihydroxypyrimidine-5 C=O | Tyr | CH$_2$CH$_2$ | N/N | H | — | 2 | >10000 | L |
| 5 | Caffeoyl | Nε-caffeoyl-Lys | CH$_2$CH$_2$ | C/C | H | — | 2 | 510 | L |
| 6 | Caffeoyl | Nε-caffeoyl-Lys benzyl ester | Single Bond | C/C | H | — | 2 | 2700 | L |
| 7 | Caffeoyl | Nγ-trityl-Asn | CH$_2$CH$_2$ | C/C | H | — | 2 | 5000 | L |
| 8 | 3,4-Dihydroxybenzoyl | Nγ-trityl-Asn | CH$_2$CH$_2$ | C/C | H | — | 2 | 5000 | L |
| 9 | 3,4-Dihydroxybenzoyl | O-benzyl-Thr | CH$_2$CH$_2$ | C/C | H | — | 2 | >5000 | L |
| 10 | Caffeoyl | O-benzyl-Thr | CH$_2$CH$_2$ | C/C | H | — | 2 | 5000 | L |
| 11 | Caffeoyl | Nδ-caffeoyl-Orn | CH$_2$CH$_2$ | C/C | H | — | 2 | 870 | L |
| 12 | Caffeoyl | S-trityl-Cys | CH$_2$CH$_2$ | C/C | H | — | 2 | 472 | L |

TABLE 1-continued

For table 1 (below) the compounds are of the following structure

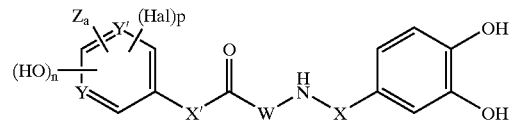

| Example No. | Ar—X'—C=O [Basic Group] | W [Residue of] | X | Y/Y' | Za | (Hal)p p | n | IC$_{50}$ (nM) | D, L, DL |
|---|---|---|---|---|---|---|---|---|---|
| 13 | Caffeoyl | Nτ-trityl-His | CH$_2$CH$_2$ | C/C | H | — | 2 | 369 | L |
| 14 | 3,4-Dihydroxybenzoyl | Nτ-trityl-His | CH$_2$CH$_2$ | C/C | H | — | 2 | 65 | L |
| 15 | 4-Hydroxy-3-nitrobenzoyl | 3,4-Dihydroxy-Phe | CH$_2$CH$_2$ | C/C | 3-NO$_2$ | — | 1 | 433 | L |
| 16 | 3,4-Dihydroxybenzoyl | Nτ-trityl-His | CH$_2$CH$_2$ | C/C | H | — | 2 | 155 | D |
| 17 | 4-Hydroxy-3-nitrobenzoyl | Nτ-trityl-His | CH$_2$CH$_2$ | C/C | 3-NO$_2$ | — | 1 | 1600 | L |
| 18 | 4-Hydroxy-3-nitrobenzoyl | Nτ-trityl His | CH$_2$CH$_2$ | C/C | 3-NO$_2$ | — | 1 | 562 | D |
| 19 | Caffeoyl | Nτ-diNO$_2$phenyl-His | CH$_2$CH$_2$ | C/C | H | — | 2 | 560 | L |
| 20 | 4-Amino-3-hydroxybenzoyl | 3,4-Dihydroxy-Phe | Single Bond | C/C | 4-NH$_2$ | — | 1 | >5000 | L |
| 21 | 3,4-Dihydroxybenzoyl | Nτ-diNO$_2$phenyl-His | CH$_2$CH$_2$ | C/C | H | — | 2 | 151 | L |
| 22 | Fmoc | Nτ-trityl-His | CH$_2$ | C/C | H | — | 0 | 5000 | L |
| 23 | 3,4-Dihydroxybenzoyl | Nτ-diNO$_2$phenyl-His | CH$_2$ | C/C | H | — | 2 | 262 | L |
| 24 | t-Boc | Nτ-diNO$_2$phenyl-His | CH$_2$ | C/C | H | — | 0 | >5000 | L |
| 25 | 3,4-Dihydroxybenzoyl | Nτ-trityl-His | CH$_2$ | C/C | H | — | 2 | >1000 | L |
| 26 | 4-Hydroxy-3-nitrobenzoyl | Nδ-methyltrityl-Gln | CH$_2$ | C/C | 3-NO$_2$ | — | 1 | 533 | L |
| 27 | Dihydrocaffeoyl | Nτ-trityl-His | CH$_2$CH$_2$ | C/C | H | — | 2 | >5000 | L |
| 28 | Dihydrocaffeoyl | Nτ-methyltrityl-His | CH$_2$CH$_2$ | C/C | H | — | 2 | 713 | L |
| 29 | 3,4-Dihydroxybenzyol | Nτ-trityl-His | Single Bond | C/C | H | — | 2 | 1600 | L |
| 30 | 3-Hydroxy-4-nitrobenzoyl | 3,4-Dihyroxy-Phe | Single Bond | C/C | 4-NO$_2$ | — | 1 | 2800 | L |
| 31 | Caffeoyl | Nτ-trityl-His | CH$_2$ | C/C | H | — | 2 | 364 | L |
| 32 | 3,4-Dihydroxybenzoyl | Nδ-methyltrityl-Gln | CH$_2$ | C/C | H | — | 2 | 256 | L |
| 33 | Caffeoyl | Nδ-methyltrityl-Gln | CH$_2$ | C/C | H | — | 2 | 155 | L |
| 34 | 4-Hydroxy-3-nitrobenzoyl | O-benzyl-Ser | CH$_2$CH$_2$ | C/C | 3-NO$_2$ | — | 1 | 1800 | L |
| 35 | 3-Nitrocinnamoyl | Nτ-trityl-His | CH$_2$CH$_2$ | C/C | 3-NO$_2$ | — | 0 | 1200 | L |
| 36 | 4-Hydroxy-3-nitrobenzoyl | Nτ-methyltrityl-His | CH$_2$CH$_2$ | C/C | 3-NO$_2$ | — | 1 | 575 | L |
| 37 | 2,4,6-Trihydroxybenzoyl | Nε-C$_6$H$_5$CH$_2$OCO-Lys | CH$_2$CH$_2$ | C/C | H | — | 3 | 1600 | L |
| 38 | 2-Fluoro-6-hydroxybenzoyl | S-trityl-Cys | CH$_2$CH$_2$ | C/C | H | F | 1 | 1400 | L |
| 39 | 3,4,5-Trihydroxybenzoyl | Nτ-trityl-His | CH$_2$CH$_2$ | C/C | H | — | 3 | 222 | L |
| 40 | Caffeoyl | Nτ-benzyl-His | CH$_2$CH$_2$ | C/C | H | — | 2 | 836 | L |
| 41 | 4-Nitrocinnamoyl | Nτ-trityl-His | CH$_2$2 | C/C | 4-NO$_2$ | — | 0 | 1140 | L |
| 42 | Caffeoyl | O-t-butyl-Ser | CH$_2$CH$_2$ | C/C | H | — | 2 | 442 | L |
| 43 | 3,4,5-Trihydroxybenzoyl | O-t-butyl-Ser | CH$_2$CH$_2$ | C/C | H | — | 3 | 152 | L |
| 44 | 2,5-Dimethoxycinnamoyl | O-t-butyl-Ser | CH$_2$CH$_2$ | C/C | H | — |  | >10000 | L |
| 45 | 3,4,5-Trihydroxybenzoyl | Ser | CH$_2$CH$_2$ | C/C | H | — | 3 | 446 | L |
| 46 | 2,5-Dimethoxycinnamoyl | Ser | CH$_2$CH$_2$ | C/C | H | — | 2 | >10000 | L |
| 47 | 3,4-Dihydroxybenzoyl | O-t-butyl-Ser | CH$_2$CH$_2$ | C/C | H | — | 2 | >10000 | L |
| 48 | Caffeoyl | Nδ-methyltrityl-Gln | CH$_2$CH$_2$ | C/C | H | — | 2 | 1150 | DL |
| 49 | 3,4-Dihydroxybenzoyl | Nδ-methyltrityl-Gln | CH$_2$CH$_2$ | C/C | H | — | 2 | 1296 | L |
| 50 | 3-Nitrocinnamoyl | Nδ-methyltrityl-Gln | CH$_2$CH$_2$ | C/C | 3-NO$_2$ | — |  | 3950 | L |
| 51 | Caffeoyl | Nδ-Boc-Orn | CH$_2$CH$_2$ | C/C | H | — | 2 | >10000 | L |
| 52 | 4-Hydroxybenzoyl | Nτ-trityl-His | CH$_2$CH$_2$ | C/C | H | — | 1 | 3300 | L |
| 53 | 3,4-Dihydroxybenzoyl | Ser | CH$_2$CH$_2$ | C/C | H | — | 2 | >10000 | L |
| 54 | 3,4,5-Trihydroxybenzoyl | Nδ-Boc-Orn | CH$_2$CH$_2$ | C/C | H | — | 3 | 374 | L |

TABLE 2

For table 2 the compounds are of the following structure.

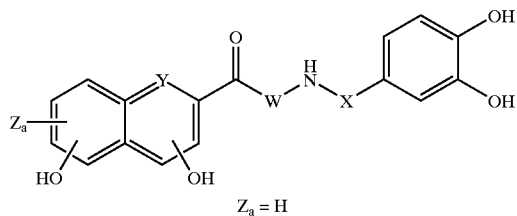

$Z_a$ = H

| Example No. | Ar [Basic Group] | W [Residue of] | X | Y | IC$_{50}$ (nM) | D, L, DL |
|---|---|---|---|---|---|---|
| 55 | 3,5-Dihydroxynaphthyl | Nε-(3,5-dihydroxynaphthyl)-Lys benzyl ester | Single Bond | C | >5000 | L |
| 56 | 3,5-Dihydroxynaphthyl | Nε-(3,5-dihydroxynaphthyl)-Lys hydroxylamide | Single Bond | C | 5300 | L |
| 57 | 3,5-Dihydroxynaphthyl | Tyr | CH$_2$CH$_2$ | C | 1100 | L |
| 58 | 4,8-Dihydroxyquinolyl | Tyr | CH$_2$CH$_2$ | N | 1200 | L |
| 59 | 3,5-Dihydroxynaphthyl | Trp | CH$_2$CH$_2$ | C | 620 | L |
| 60 | 3,5-Dihydroxynaphthyl | 3,4-Dihydroxy-Phe | CH$_2$CH$_2$ | C | 1800 | L |
| 61 | 3,5-Dihydroxynaphthyl | Asn | CH$_2$CH$_2$ | C | >5000 | L |
| 62 | 4,8-Dihydroxyquinolyl | Asp Oγ-t-butyl ester | CH$_2$CH$_2$ | N | >5000 | L |
| 63 | 4,8-Dihydroxyquinolyl | Asp | CH$_2$CH$_2$ | N | 5000 | L |
| 64 | 4,8-Dihydroxyquinolyl | Nγ-trityl-Asn | CH$_2$CH$_2$ | N | 7100 | L |
| 65 | 3,5-Dihydroxynaphthyl | Nε-(3,5-dihydroxynaphthyl)-Lys | Single Bond | C | >5000 | L |
| 66 | 3,5-Dihydroxynaphthyl | Nε-(3,5-dihydroxynaphthyl)-Lys | CH$_2$CH$_2$ | C | >5000 | L |
| 67 | 4,8-Dihydroxyquinolyl | Asn | CH$_2$CH$_2$ | N | >5000 | L |
| 68 | 4,8-Dihydroxyquinolyl | Tyr | CH$_2$ | N | >5000 | L |
| 69 | 4,8-Dihydroxyquinolyl | Nδ-methyltrityl-Gln | CH$_2$ | N | 346 | L |
| 70 | 4,8-Dihydroxyquinolyl | Nτ-trityl-His | CH$_2$ | N | 403 | L |
| 71 | 4,8-Dihydroxyquinolyl | Nτ-methyltrityl-His | CH$_2$CH$_2$ | N | 607 | L |
| 72 | 4,8-Dihydroxyquinolyl | O-t-butyl-Ser | CH$_2$CH$_2$ | N | >10000 | L |

TABLE 3

For table 3 the compounds are of the following structure

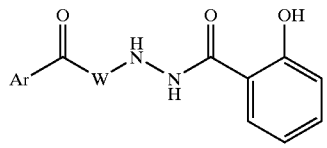

| Example No. | Ar—X'—C=O [Basic Group] | W [Residue of] | IC$_{50}$(nM) | D, L, DL |
|---|---|---|---|---|
| 73 | 4,8-Dihydroxyquinolyl-2-C=O | Tyr | 2200 | L |
| 74 | Caffeoyl | Tyr | 820 | L |
| 75 | Caffeoyl | Trp | 1200 | L |
| 76 | Caffeoyl | 3,4-Dihydroxy-Phe | 383 | |
| 77 | 4,8-Dihydroxyquinolyl-2-C=O | Trp | 4700 | L |
| 78 | 4,8-Dihydroxyquinolyl-2-C=O | Nδ-2-OHBz-Glu | >9700 | L |
| 79 | Boc* | Nτ-diNO$_2$phenyl-His | >4000 | L |
| 80 | Caffeoyl | Nτ-diNO$_2$phenyl-His | 251 | L |
| 81 | 3-(3'-thiophenyl)acryloyl | Nτ-diNO$_2$phenyl-His | >10000 | L |

*intermediate for example numbers 80 and 81

TABLE 4

For table 4 the compounds are of the following structure

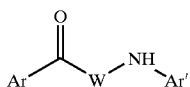

| Example No. | Ar—C=O [Basic Group] | W [Residue of] | Ar'NH— [Residue of] | IC$_{50}$(nM) | D, L, DL |
|---|---|---|---|---|---|
| 82 | Caffeoyl | Nδ-trityl-Gln | 2,5-Dimethoxyaniline | 2550 | L |
| 83 | 3,4-Dithydroxybenzoyl | Nδ-trityl-Gln | 2,5-Dimethoxyaniline | 2250 | L |
| 84 | Indolyl-2-carbonyl | Nδ-trityl-Gln | 2,5-Dimethoxyaniline | 4100 | L |
| 85 | 4,8-Dithydroxyquinolyl-2-carbonyl | Nδ-trityl-Gln | 2,5-Dimethoxyaniline | 2600 | L |
| 86 | 3-(3'-Indolyl)acryloyl | Nτ-trityl-His | Dopamine | 2000 | L |
| 87 | 2-Thiopheneacetyl | O-t-butyl-Ser | Dopamine | >10000 | L |
| 88 | Pyrrole-2-carbonyl | Nδ-trityl-Gln | 2,5-Dimethyoxyaniline | >10000 | L |
| 89 | N-(4-fluorobenzyl)indole-2-carbonyl | Oδ-t-butyl-Glu | Benzylamine | >10000 | L |
| 90 | Caffeoyl | Nδ-methyltrityl-Gln | Thiazole-2-amine | 834 | L |
| 91 | Pyrrole-2-carbonyl | Gln | 2,5-Dimethoxyaniline | >10000 | L |
| 92 | N-(4-fluorobenzyl)indole-2-carbonyl | Nδ-methyltrityl-Gln | 2,5-Dimethoxyaniline | N/A | L |
| 93 | N-(4-fluorobenzyl)pyrrole-2-carbonyl | O-t-butyl-Ser | Dopamine | >10000 | L |
| 94 | N-(4-fluorobenzyl)indole-2-carbonyl | Glu | Benzylamine | 9250 | L |
| 95 | N-(4-fluorobenzyl)indole-2-carbonyl | O-t-butyl-Ser | Dopamine | 7000 | L |
| 96 | N-(4-fluorobenzyl)indole-2-carbonyl | Ser | Dopamine | >10000 | L |
| 97 | 3,4-Di-(4-fluorobenzyloxy)benzoyl | O-t-butyl-Ser | Dopamine | 2900 | L |
| 98 | 3,4-Di-(4-fluorobenzyloxy)caffeoyl | Gly | 2-(2'-Thiophenyl)ethyamine | >10000 | |
| 99 | 3,4-Di-(4-fluorobenzyloxy)benzoyl | Oδ-t-butyl-Glu | Benzylamine | >10000 | L |
| 100 | 3,4-Di-(4-fluorobenzyloxy)caffeoyl | Gly | Dopamine | 2600 | |
| 101 | N-(4-fluorobenzyl)pyrrole-2-carbonyl | Oδ-t-butyl-Glu | 2-(2'-Thiophenyl)ethyamine | >10000 | L |
| 102 | N-(4-fluorobenzyl)indole-2-carbonyl | Oδ-t-butyl-Glu | 2-(2'-Thiophenyl)ethyamine | >10000 | L |
| 103 | N-(4-fluorobenzyl)pyrrole-2-carbonyl | Glu | 2-(2'-Thiophenyl)ethyamine | >10000 | L |
| 104 | N-(4-fluorobenzyl)indole-2-carbonyl | Glu | 2-(2'-Thiophenyl)ethyamine | >10000 | L |
| 105 | 4,8-Dihydroxyquinolyl-2-carbonyl | Oδ-t-butyl-Glu | 2-(2'-Thiophenyl)ethyamine | >10000 | L |
| 106 | 4,8-Dihydroxyquinolyl-2-carbonyl | Glu | 2-(2'-Thiophenyl)ethyamine | >10000 | L |
| 107 | 5-Fluoro-2-hydroxybenzoyl | Oδ-t-butyl-Glu | 2-(2'-Thiophenyl)ethyamine | >10000 | L |
| 108 | 5-Fluoro-2-hydroxybenzoyl | Glu | 2-(2'-Thiophenyl)ethyamine | >10000 | L |
| 109 | N-(4-fluorobenzyl)indole-2-carbonyl | Nδ-trityl-Gln | 3-Hydroxy-4-methoxyaniline | 5300 | L |

TABLE 4-continued

For table 4 the compounds are of the following structure

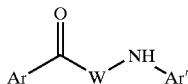

| Example No. | Ar—C=O [Basic Group] | W [Residue of] | Ar'NH— [Residue of] | IC$_{50}$(nM) | D, L, DL |
|---|---|---|---|---|---|
| 110 | N-(4-fluorobenzyl)indole-2-carbonyl | Gln | 3-Hydroxy-4-methoxyaniline | N/A | L |
| 111 | 3,4-Di-(4-fluorobenzyloxy)benzoyl | Nδ-trityl-Gln | 3-Hydroxy-4-methoxyaniline | 6100 | L |
| 112 | 3,4-Di-(4-fluorobenzyloxy)caffeoyl | Nδ-trityl-Gln | 3-Hydroxy-4-methoxyaniline | 2000 | L |
| 113 | 5-Fluoroindole 2-carbonyl | Nδ-trityl-Gln | 3-Hydroxy-4-methoxyaniline | 6500 | L |

We claim:
1. An hydroxyphenyl compound of formula Ia

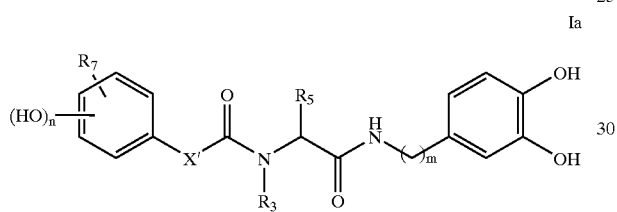

and when a compound of formula Ia comprises a carboxylic acid group pharmaceutically acceptable salts thereof and when a compound of formula Ia comprises an amino group pharmaceutically acceptable ammonium salts thereof, wherein $R_3$ represents H or —CH$_3$, $R_5$ is selected from the group consisting of H, $C_1$ to $C_8$ alkyl (straight or branched), HO$_2$C—($C_1$ to $C_8$)alkyl (straight or branched)—, $C_6H_5CH_2$—, CH$_3$SCH$_2$CH$_2$—, H$_2$NC(O)—($C_1$ to $C_8$)alkyl (straight or branched)—, HO($C_1$ to $C_8$)alkyl (straight or branched)—, HSCH$_2$—, H$_2$N—($C_1$ to $C_8$)alkyl (straight or branched),

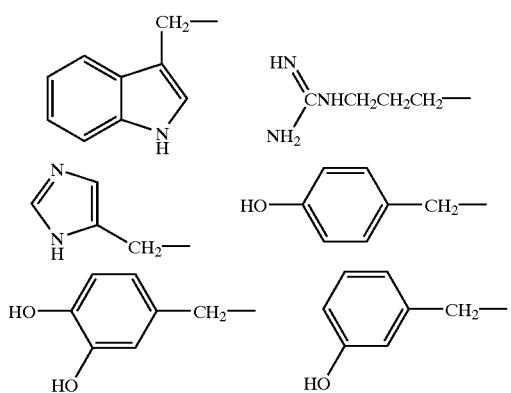

$R_{20}O_2C$—($C_1$ to $C_8$)alkyl (straight or branched)—,
$R_{20}HNC(O)$—($C_1$ to $C_8$)alkyl (straight or branched)—,
$R_{20}HN$—($C_1$ to $C_8$)alkyl (straight or branched),
$R_{20}O$—($C_1$ to $C_8$)alkyl (straight or branched)—,
$R_{20}SCH_2$—

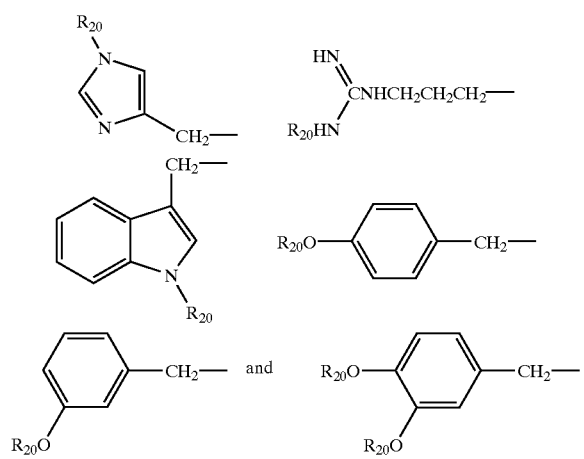

$R_{20}$ is a predetermined protecting group substituent $R_7$ is selected from the group consisting of —NO$_2$, —NH$_2$, alkyl-O—, cycloalkyl-O—, aryl-O—, benzyloxy, —SH, alkyl-S—, aryl-S—, alkyl-CONH—, aryl-CONH, wherein alkyl signifies an unsubstituted straight or branched alkyl group with 1 to 8 carbon atoms, cycloalkyl signifies an unsubstituted radical with 3 to 8 carbon atoms and aryl signifies an unsubstituted phenyl group, an unsubstituted benzyl group or a phenyl or benzyl group substituted by one or more of the same or different substituents selected from the group consisting of —OH, —OCH$_3$, —SH, —SCH$_3$, —NO$_2$, —NH$_2$, —F, —Cl, and —Br, X' represents a single bond, a saturated straight or branched hydrocarbon group of 1 to 4 carbon atoms or a straight or branched hydrocarbon group of 2 to 4 carbon atoms comprising a carbon to carbon double bond, n is 1, 2 or 3 and m is 1 or 2.

2. An hydroxyphenyl compound of formula Ia as defined in claim 1 wherein n is 1 or 2.

3. An hydroxyphenyl compound of formula Ia as defined in claim 2 wherein $R_7$ is NO$_2$— or NH$_2$—.

4. An hydroxyphenyl compound of formula Ia as defined in claim 3 wherein X' is selected from the group consisting of a single bond, —CH=CH—, —CH$_2$— and —CH$_2$CH$_2$—.

5. An hydroxyphenyl compound of formula Ia as defined in claim 4 wherein R$_5$ is selected from the group consisting of H, CH$_3$—, (CH$_3$)$_2$CH—, (CH$_3$)$_2$CHCH$_2$—, C$_6$H$_5$CH$_2$—, CH$_3$CH$_2$CH(CH$_3$)—, CH$_3$SCH$_2$CH$_2$—, HO$_2$CCH$_2$—, H$_2$NC(O)CH$_2$—, HO$_2$CCH$_2$—, H$_2$NC(O)CH$_2$CH$_2$—, H$_2$NCH$_2$CH$_2$CH$_2$—, H$_2$NCH$_2$CH$_2$CH$_2$CH$_2$—, H$_2$NCH$_2$CH$_2$CH$_2$CH$_2$CH$_2$—, HOCH$_2$—, CH$_3$CH(OH)—, HSCH$_2$—,

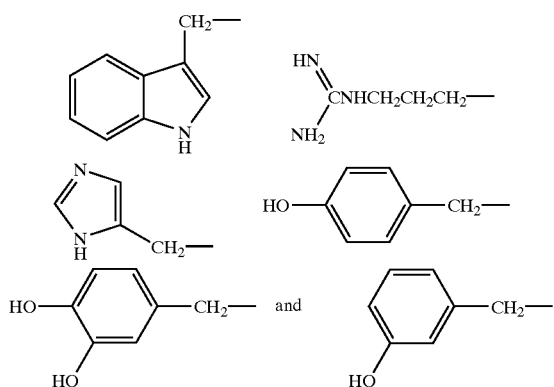

6. An hydroxyphenyl compound of formula Ia as defined in claim 4 wherein R$_5$ is selected from the group consisting of R$_{20}$O$_2$CCH$_2$—, R$_{20}$HNC(O)CH$_2$—, R$_{20}$O$_2$CCH$_2$CH$_2$—, R$_{20}$HNC(O)CH$_2$CH$_2$—, R$_{20}$HNCH$_2$CH$_2$CH$_2$—, R$_{20}$HNCH$_2$CH$_2$CH$_2$CH$_2$—, R$_{20}$HNCH$_2$CH$_2$CH$_2$CH$_2$CH$_2$—, R$_{20}$OCH$_2$—, CH$_3$CH(OR$_{20}$)—, R$_{20}$SCH$_2$—

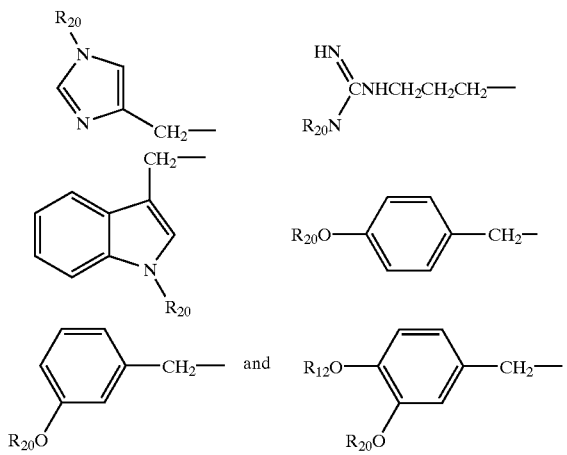

wherein R$_{20}$ is selected from the group consisting of tert-butoxycarbonyl, 9-fluorenylmethoxycarbonyl, benzyl, benzyloxycarbonyl, tert-butyl, cyclohexyl, 2,4-dinitrophenyl, trityl, methyltrityl, p-Br-benzyl, p-Cl-benzyl, 2,6-dichlorobenzyl, 2,6-fluorobenzyl, p-cyanobenzyl, p-phenylbenzyl, 4-methoxybenzyl, 3,4-dimethoxybenzyl, o-nitrobenzyl, p-nitrobenzyl, 4-methylbenzyl, trifluoromethylbenzyl, p-acylamino-benzyl, the acyl moiety thereof containing 1 to 8 carbon atoms in addition to the carbon atom of the carbonyl group, p-azidobenzyl, 4-azido-3-chlorobenzyl, p-(methylsulfinyl)benzyl, 4,4'-dimethoxybenzhydryl, 2-bromobenzyloxycarbonyl, 2-chlorobenzyloxycarbonyl, straight or branched C$_1$–C$_8$-alkyl, C$_3$–C$_8$-cycloalkyl, xanthyl, 4-methoxytrityl, di-(4-methoxy)trityl, and tri-(4-methoxy)trityl.

7. An hydroxyphenyl compound of formula Ia as defined in claim 5 wherein R$_3$ is H.

8. An hydroxyphenyl compound as defined in claim 6 wherein R$_{20}$ is selected from the group consisting of tert-butoxycarbonyl, 9-fluorenylmethoxycarbonyl, benzyl, benzyloxycarbonyl, tert-butyl, cyclohexyl, 2,4-dinitrophenyl, trityl, methyltrityl.

9. An hydroxyphenyl compound of formula Ia as defined in claim 8 wherein R$_3$ is H.

10. An hydroxyphenyl compound of formula Ia as defined in claim 7, wherein m is 2.

11. An hydroxyphenyl compound of formula Ia as defined in claim 9, wherein m is 2.

12. An hydroxyphenyl compound of formula Ig

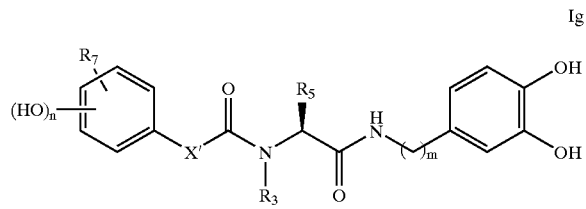

and when a compound of formula Ig comprises a carboxylic acid group pharmaceutically acceptable salts thereof and when a compound of formula Ig comprises an amino group pharmaceutically acceptable ammonium salts thereof, wherein n, m, X', R$_3$, R$_5$ and R$_7$ are as defined in claim 1.

13. An hydroxyphenyl compound of formula Ig as defined in claim 12, wherein n is 1 or 2.

14. An hydroxyphenyl compound of formula Ig as defined in claim 13, wherein R$_7$ is NO$_2$— or NH$_2$—.

15. An hydroxyphenyl compound of formula Ig as defined in claim 14, wherein X' is selected from the group consisting of a single bond, —CH=CH—, —CH$_2$— and —CH$_2$CH$_2$—.

16. An hydroxyphenyl compound of formula Ig as defined in claim 15 wherein R$_5$ is as defined in claim 5.

17. An hydroxyphenyl compound of formula Ig as defined in claim 15 wherein R$_5$ is as defined in claim 6.

18. An hydroxyphenyl compound of formula Ig as defined in claim 16 wherein R$_3$ is H.

19. An hydroxyphenyl compound as defined in claim 17 wherein R$_{20}$ is selected from the group consisting of tert-butoxycarbonyl, 9-fluorenylmethoxycarbonyl, benzyl, benzyloxycarbonyl, tert-butyl, cyclohexyl, 2,4-dinitrophenyl, trityl, methyltrityl.

20. An hydroxyphenyl compound of formula Ig as defined in claim 19 wherein R$_3$ is H.

21. An hydroxyphenyl compound of formula Ig as defined in claim 18, wherein m is 2.

22. An hydroxyphenyl compound of formula Ig as defined in claim 20, wherein m is 2.

23. A dopamine derivative of formula
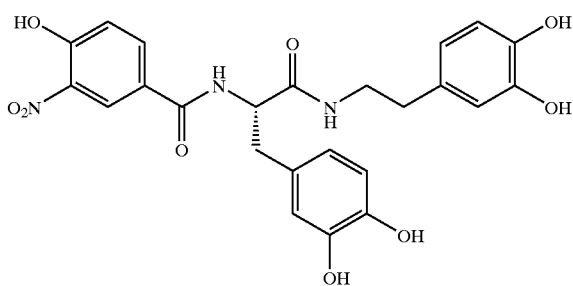
24. A benzylamine derivative of formula
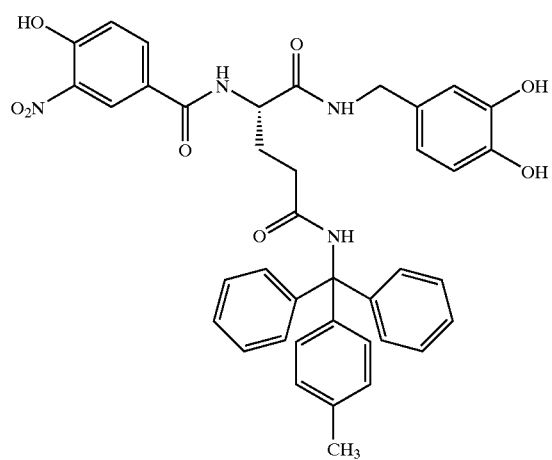
25. A dopamine derivative of formula
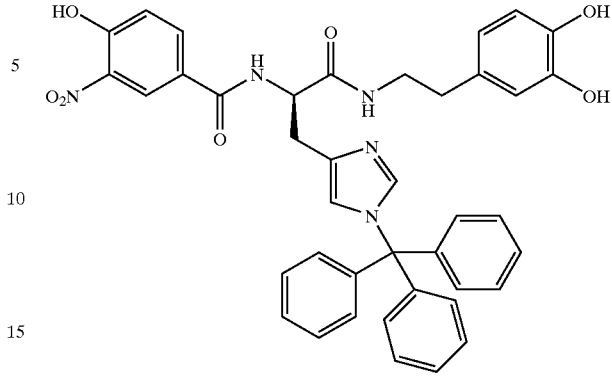
26. A dopamine derivative of formula
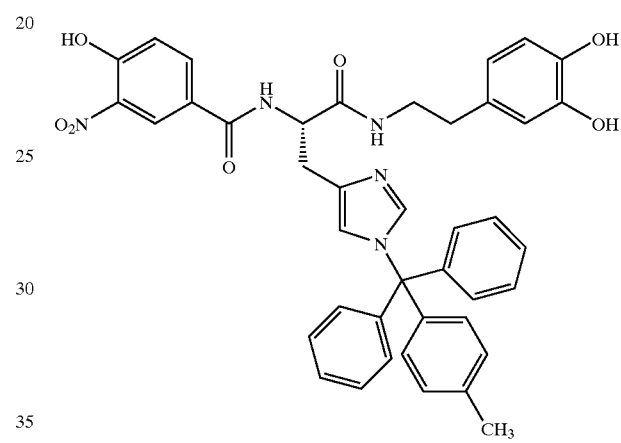
* * * * *